(12) United States Patent
Brown et al.

(10) Patent No.: US 9,096,500 B2
(45) Date of Patent: Aug. 4, 2015

(54) ACYL SULFONAMIDE COMPOUNDS

(75) Inventors: Alan Daniel Brown, Sandwich (GB);
David James Rawson, Sandwich (GB);
Robert Ian Storer, Sandwich (GB);
Nigel Alan Swain, Sandwich (GB)

(73) Assignee: Pfizer Limited, Sandwich (GB)

( * ) Notice: Subject to any disclaimer, the term of this patent is extended or adjusted under 35 U.S.C. 154(b) by 139 days.

(21) Appl. No.: 13/808,639

(22) PCT Filed: Jul. 4, 2011

(86) PCT No.: PCT/IB2011/052940
§ 371 (c)(1),
(2), (4) Date: Jan. 7, 2013

(87) PCT Pub. No.: WO2012/007868
PCT Pub. Date: Jan. 19, 2012

(65) Prior Publication Data
US 2013/0109701 A1    May 2, 2013

Related U.S. Application Data

(60) Provisional application No. 61/363,371, filed on Jul. 12, 2010, provisional application No. 61/484,838, filed on May 11, 2011.

(51) Int. Cl.
| | | |
|---|---|---|
| C07C 311/04 | (2006.01) |
| A61K 31/18 | (2006.01) |
| C07C 311/51 | (2006.01) |
| C07D 231/12 | (2006.01) |
| A61K 31/277 | (2006.01) |
| A61K 31/415 | (2006.01) |
| A61K 31/4245 | (2006.01) |
| A61K 31/451 | (2006.01) |
| A61K 31/495 | (2006.01) |
| A61K 31/50 | (2006.01) |
| A61K 45/06 | (2006.01) |
| C07D 211/22 | (2006.01) |
| C07D 237/08 | (2006.01) |
| C07D 241/04 | (2006.01) |
| C07D 271/06 | (2006.01) |

(52) U.S. Cl.
CPC ............ *C07C 311/04* (2013.01); *A61K 31/18* (2013.01); *A61K 31/277* (2013.01); *A61K 31/415* (2013.01); *A61K 31/4245* (2013.01); *A61K 31/451* (2013.01); *A61K 31/495* (2013.01); *A61K 31/50* (2013.01); *A61K 45/06* (2013.01); *C07C 311/51* (2013.01); *C07D 211/22* (2013.01); *C07D 231/12* (2013.01); *C07D 237/08* (2013.01); *C07D 241/04* (2013.01); *C07D 271/06* (2013.01)

(58) Field of Classification Search
None
See application file for complete search history.

(56) References Cited

U.S. PATENT DOCUMENTS

| | | | |
|---|---|---|---|
| 4,744,818 A | 5/1988 | Heiba et al. |
| 5,543,279 A | 8/1996 | Matsuda et al. |
| 5,565,429 A | 10/1996 | Vincent et al. |
| 5,851,745 A | 12/1998 | Takeuchi |
| 6,251,827 B1 | 6/2001 | Ziemer et al. |
| 6,348,474 B1 | 2/2002 | Kayakiri et al. |
| 6,376,512 B1 | 4/2002 | Jayyosi et al. |
| 6,555,584 B1 | 4/2003 | Ikawa et al. |
| 7,772,285 B2 | 8/2010 | Chaki et al. |
| 8,314,240 B2 | 11/2012 | Kubota et al. |
| 2002/0086887 A1 | 7/2002 | Augeri et al. |
| 2008/0027096 A1* | 1/2008 | Garg et al. .................... 514/311 |
| 2008/0188467 A1 | 8/2008 | Wong et al. |
| 2010/0179137 A1 | 7/2010 | Kamikubo et al. |
| 2012/0010182 A1 | 1/2012 | Brown et al. |
| 2012/0010183 A1 | 1/2012 | Bell et al. |
| 2012/0010207 A1 | 1/2012 | Bell et al. |
| 2013/0109667 A1 | 5/2013 | Markworth et al. |
| 2013/0109696 A1 | 5/2013 | Greener et al. |
| 2013/0109708 A1 | 5/2013 | Brown et al. |
| 2013/0116285 A1 | 5/2013 | Bell et al. |

FOREIGN PATENT DOCUMENTS

| | | |
|---|---|---|
| EP | 0003416 | 8/1979 |
| EP | 0023100 | 1/1981 |
| EP | 0029742 | 6/1981 |
| EP | 0194599 | 9/1986 |
| EP | 0281103 | 9/1988 |
| EP | 0325245 | 7/1989 |
| EP | 0399732 | 11/1990 |
| EP | 0412848 | 2/1991 |
| EP | 0453210 | 10/1991 |
| EP | 0570006 | 11/1993 |
| EP | 0684521 | 11/1995 |
| EP | 0753508 | 1/1997 |
| GB | 2266527 | 11/1993 |
| WO | 8801133 | 2/1988 |
| WO | 8904303 | 5/1989 |

(Continued)

OTHER PUBLICATIONS

"Molecular Mechanisms of Cancer Pain" by Mantyh et al., Nature Rev. 2, 201-09 (2002).*
Silverman, Richard B. The Organic Chemistry of Drug Design and Drug Action. 2nd Ed., 2004, pp. 29-32, Elsevier, Burlington, MA.
Naganawa et al., "Further optimization of sulfonamide analogs as EP1 receptor antagonists: Synthesis and evaluation of bioisosteres for the carboxylic acid group", Bioorganic & Medicinal Chemistry, vol. 14(21), pp. 7121-7137 (2006).

(Continued)

*Primary Examiner* — Theodore R West
(74) *Attorney, Agent, or Firm* — J. Michael Dixon

(57) ABSTRACT

The invention relates to sulfonamide derivatives, to their use in medicine, to compositions containing them, to processes for their preparation and to intermediates used in such processes. More particularly the invention relates to a new sulfonamide Nav1.7 inhibitors of formula (I): or a pharmaceutically acceptable salt thereof, wherein X, $Ar^1$, $R^1$, $R^2$, $R^3$, $R^4$ and $R^5$ are as defined in the description. Nav 1.7 inhibitors are potentially useful in the treatment of a wide range of disorders, particularly pain.

13 Claims, No Drawings

(56) References Cited

FOREIGN PATENT DOCUMENTS

| WO | 8904304 | 5/1989 |
| WO | 8904305 | 5/1989 |
| WO | 8912628 | 12/1989 |
| WO | 9104964 | 4/1991 |
| WO | 9300332 | 1/1993 |
| WO | 9413636 | 6/1994 |
| WO | 9421590 | 9/1994 |
| WO | 9604905 | 2/1996 |
| WO | 9609818 | 4/1996 |
| WO | 9920275 | 4/1999 |
| WO | 9947508 | 9/1999 |
| WO | 0039077 | 7/2000 |
| WO | 0064876 | 11/2000 |
| WO | 0066120 | 11/2000 |
| WO | 0136365 | 5/2001 |
| WO | 0166098 | 9/2001 |
| WO | 0224636 | 3/2002 |
| WO | 2004018386 | 3/2004 |
| WO | 2005013914 A2 | 2/2005 |
| WO | 2005080346 | 9/2005 |
| WO | 2005094810 | 10/2005 |
| WO | 2006015158 | 2/2006 |
| WO | 2006045514 | 5/2006 |
| WO | 2006121097 | 11/2006 |
| WO | 2007072782 A1 | 6/2007 |
| WO | 2008025539 | 3/2008 |
| WO | 2008092231 | 8/2008 |
| WO | 2008118758 | 10/2008 |
| WO | 2009012242 | 1/2009 |
| WO | 2009049181 | 4/2009 |
| WO | 2009064250 | 5/2009 |
| WO | 2009064251 | 5/2009 |
| WO | 2009067541 | 5/2009 |
| WO | 2009067621 | 5/2009 |
| WO | 2009080835 | 7/2009 |
| WO | 2010079443 | 7/2010 |

OTHER PUBLICATIONS

Pinkerton et al., "Allosteric potentiators of the metabotropic glutamate receptor 2 (mGlu2). Part 3: Identification and biological activity of indanone containing mGlu2 receptor potentiators", Bioorganic & Medicinal Chemistry Letters, vol. 15(6), pp. 1565-1571 (2005).

Ng et al., "Design, Synthesis, and Biological Activity of Novel Factor Xa Inhibitors: 4-Aryloxy Substituents of 2,6-Diphenoxypyridines", Bioorganic & Medicinal Chemistry, vol. 10(3), pp. 657-666 (2002).

Zakarya et al., "Substituent effects on the toxicity for a series of herbicides", Romanian Chemical Quarterly Reviews, vol. 7(2), pp. 127-137 (1999).

Hamill et al., "Development of [11C]L-159,884: A Radiolabelled, Nonpeptide Angiotensin II Antagonist that is Useful for Angiotensin II, AT1 Receptor Imaging", Applied Radiation and Isotopes, vol. 47(2), pp. 211-218 (1996).

Matassa et al., "Synthesis and in Vitro LTD4 Antagonist Activity of Bicyclic and Monocyclic Cyclopentylurethane and Cyclopentylacetamide N-Arylsulfonyl Amides", Journal of Medicinal Chemistry, vol. 33(9), pp. 2621-2629 (1990).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", Journal of Medicinal Chemistry, vol. 33(1), pp. 240-245 (1990).

Brown et al., "Hydroxyacetophenone-Derived Antagonists of the Peptidoleukotriens", Journal of Medicinal Chemistry, vol. 32(4), pp. 807-826 (1989).

Dubois et al., "Dihydrochalcone Sweeteners. A Study of the Atypical Temporal Phenomena", Journal of Medicinal Chemistry, vol. 24(4), pp. 408-428 (1981).

* cited by examiner

ACYL SULFONAMIDE COMPOUNDS

CROSS REFERENCE

This application is the National Stage Application of International Patent Application No. PCT/IB2011/052940, filed Jul. 4, 2011, which claims priority to U.S. Provisional Patent Application No. 61/484,838, filed on May 11, 2011 and U.S. Provisional Patent Application No. 61/363,371, filed on Jul. 12, 2010.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha sub-units. Names for this family include SCNx, SCNAx, and $Na_vx.x$. The VGSC family has been phylogenetically divided into two subfamilies $Na_v1.x$ (all but SCN6A) and $Na_v2.x$ (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The $Na_v1.7$ (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that $Na_v1.7$ may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, $Na_v1.7$ protein has been shown to accumulate in neuromas, particularly painful neuromas (Kretschmer et al., *Acta. Neurochir. (Wien)*, 144(8): 803-10 (2002)). Gain of function mutations of $Na_v1.7$, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.;* 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.;* 71(4): 311-9 (2007), Ahmad et al, *Hum Mol. Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new $Na_v1.7$ inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound of formula (I)

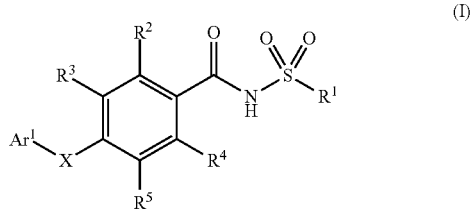

or a pharmaceutically acceptable salt thereof, wherein

X is —OCH$_2$— or —CH$_2$O—;

Ar$^1$ is (i) naphthyl; or (ii) naphthyl or phenyl each of which is independently substituted by one to three Y;

Y is F; Cl; CN; (C$_1$-C$_8$)alkyl, optionally substituted by (C$_3$-C$_8$)cycloalkyl or one to three F; (C$_3$-C$_8$)cycloalkyl, optionally substituted by one to three F; NR$^7$R$^8$; (C$_1$-C$_8$)alkyloxy, optionally independently substituted by one to three R$^9$; (C$_3$-C$_8$)cycloalkyloxy; phenyl, optionally independently substituted by one to three R$^{10}$; Het$^1$ or Het$^2$; wherein (C$_3$-C$_8$)cycloalkyloxy may be optionally fused to a phenyl ring or may be independently substituted by one to three R$^{10}$;

R$^1$ is (C$_1$-C$_6$)alkyl or (C$_3$-C$_8$)cycloalkyl, each of which is optionally substituted by one to three F;

R$^2$, R$^3$, R$^4$ are independently H, F, Cl or —OCH$_3$;

R$^5$ is H, CN, F, Cl or R$^6$;

R$^6$ is a group selected from (C$_1$-C$_6$)alkyl and (C$_1$-C$_6$)alkyloxy, wherein each group is optionally substituted, valency permitting, by one to five F;

R$^7$ and R$^8$ are independently H; (C$_1$-C$_8$)alkyl, optionally independently substituted by one to three R$^{11}$; (C$_3$-C$_8$)cycloalkyl; or 'C-linked' Het$^1$; wherein (C$_3$-C$_8$)cycloalkyl may be optionally fused to a phenyl ring or may be independently substituted by one to three R$^{10}$; or R$^7$ and R$^8$, taken together with the nitrogen atom to which they are attached, form a saturated, bridged, 7 to 9-membered ring;

R$^9$ is F; (C$_1$-C$_6$)alkyloxy; (C$_3$-C$_8$)cycloalkyl, optionally substituted by one to three F; Het$^1$; or phenyl, optionally independently substituted by one to three R$^6$;

R$^{10}$ is F, Cl or R$^6$;

R$^{11}$ is F; (C$_1$-C$_6$)alkyloxy; (C$_3$-C$_8$)cycloalkyl, optionally substituted by one to three F; 'C-linked' Het$^1$; or phenyl, optionally independently substituted by one to three R$^6$;

Het$^1$ is a 3- to 8-membered saturated monoheterocycloalkyl comprising one or two ring members selected from —NR$^{12}$— and —O—, said monoheterocycloalkyl being optionally substituted on a ring carbon atom by one to three substituents independently selected from F, (C$_1$-C$_6$)alkyl, (C$_1$-C$_4$)alkyloxy(C$_0$-C$_4$)alkylene and (C$_3$-C$_8$)cycloalkyl;

Het$^2$ is a 5- or 6-membered heteroaryl comprising one to three nitrogen atoms, said heteroaryl being optionally substituted by one to three substituents selected from F, Cl, CN and R$^6$; and R$^{12}$ is H, (C$_1$-C$_6$)alkyl or (C$_3$-C$_8$)cycloalkyl, wherein (C$_1$-C$_6$)alkyl and (C$_3$-C$_8$)cycloalkyl are optionally substituted by one to three F; or, when Het$^1$ is 'N-linked', is absent.

Described below are a number of embodiments (E) of this first aspect of the invention, where for convenience E1 is identical thereto.

E1 A compound of formula (I) as defined above or a pharmaceutically acceptable salt thereof.

E2 A compound according to E1 wherein X is —OCH$_2$—.

E3 A compound according to E1 wherein X is —CH$_2$O—.

E4 A compound according to any of E1 to E3 wherein Ar$^1$ is phenyl independently substituted by one to three Y.

E5 A compound according to any of E1 to E4 wherein Ar$^1$ is phenyl independently substituted by one or two Y.

E6 A compound according to any of E1 to E5 wherein Ar$^1$ is phenyl meta-substituted by Y, para-substituted by Y, or meta- and para-substituted by independent Y.

E7 A compound according to any of E1 to E6 wherein Y is F; Cl; CN; (C$_1$-C$_8$)alkyl, optionally substituted by (C$_3$-C$_8$)cycloalkyl or one to three F; (C$_3$-C$_8$)cycloalkyl, optionally substituted by one to three F; (C$_1$-C$_6$)alkyloxy, optionally substituted by one to three F; or (C$_3$-C$_8$)cycloalkyloxy.

E8 A compound according to any of E1 to E7 wherein Y is F; Cl; CN; (C$_1$-C$_4$)alkyl, optionally substituted by (C$_3$-C$_6$)cycloalkyl or one to three F; (C$_3$-C$_6$)cycloalkyl, optionally substituted by one to three F; (C$_1$-C$_6$)alkyloxy, optionally substituted by one to three F; or (C$_3$-C$_6$)cycloalkyloxy.

E9 A compound according to any of E1 to E8 wherein R$^1$ is (C$_1$-C$_4$)alkyl or (C$_3$-C$_6$)cycloalkyl.

E10 A compound according to any of E1 to E9 wherein R$^1$ is (C$_1$-C$_3$)alkyl or (C$_3$-C$_4$)cycloalkyl.

E11 A compound according to any of E1 to E10 wherein R$^1$ is methyl or cyclopropyl, E12 A compound according to any of E1 to E11 wherein R$^2$, R$^3$ and R$^4$ are independently H, F or Cl.

E13 A compound according to any of E1 to E12 wherein R$^2$, R$^3$ and R$^4$ are independently H or F.

E14 A compound according to any of E1 to E13 wherein R$^2$ is F; and R$^3$ and R$^4$ are independently H or F.

E15 A compound according to any of E1 to E14 wherein R$^5$ is H; CN; F; Cl; (C$_1$-C$_4$)alkyl, optionally substituted by one to three F; or (C$_1$-C$_4$)alkyloxy, optionally substituted by one to three F.

E16 A compound according to any of E1 to E15 wherein R$^5$ is H, CN, F, Cl, CH$_3$, C$_2$H$_5$, CF$_3$, —OCH$_3$, —OC$_2$H$_5$ or —OCF$_3$.

E16 A compound according to any of E1 to E15 wherein R$^5$ is F or Cl.

Alkyl, alkylene, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkylene include methylene, 1,1-ethylene, 1,2-ethylene, 1,1-propylene, 1,2-propylene, 1,3-propylene and 2,2-propylene.

Examples of cycloalkyl include cyclopropyl, cyclobutyl, cyclopentyl, cyclohexyl, cycloheptyl and cyclooctyl.

Halo means fluoro, chloro, bromo or iodo.

The term 'C-linked' used in the definitions of formula (I) means that the group in question is joined via a ring carbon. The term 'N-linked' used in the definitions of formula (I) means that the group in question is joined via a ring nitrogen.

Specific examples of 5- or 6-membered heteroaryl used in the definitions of formula (I) include pyrrolyl, pyrazolyl, imidazoyl, thiazolyl, isothiazolyl, thiadiazolyl, pyridyl, pyridazinyl, pyrimidinyl and pyrazinyl. Except as expressly defined above, when such heteroaryls are substituted, the substituent may be located on a ring carbon (in all cases) or a ring nitrogen with appropriate valency (if the substituent is joined through a carbon atom).

Specific examples of Het$^1$ include oxiranyl, aziridinyl, oxetanyl, azetidinyl, tetrahydrofuranyl, pyrrolidinyl, tetrahydropyranyl, piperidinyl, morpholinyl, piperazinyl, azepanyl, oxepanyl, oxazepanyl and diazepinyl.

Hereinafter, all references to compounds of the invention include compounds of formula (I) or pharmaceutically acceptable salts, solvates, or multi-component complexes thereof, or pharmaceutically acceptable solvates or multi-component complexes of pharmaceutically acceptable salts of compounds of formula (I), as discussed in more detail below.

Preferred compounds of the invention are compounds of formula (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of formula (I) or pharmaceutically acceptable salts thereof may exist in both unsolvated and solvated forms. The term 'solvate' is used herein to describe a molecular complex comprising a compound of formula (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of formula (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3$$^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of formula (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl)phosphate prodrugs. Further examples of replacement groups in accordance with the foregoing examples and examples of other prodrug types may be found in the aforementioned references.

Also included within the scope of the invention are metabolites of compounds of formula (I), that is, compounds formed in vivo upon administration of the drug. Some examples of metabolites in accordance with the invention include, where the compound of formula (I) contains a phenyl (Ph) moiety, a phenol derivative thereof (-Ph>-PhOH);

Compounds of the invention containing one or more asymmetric carbon atoms can exist as two or more stereoisomers. Included within the scope of the invention are all stereoisomers of the compounds of the invention and mixtures of one or more thereof.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of formula (I). The invention includes all polymorphs of the aforementioned species and crystal habits thereof.

When preparing a compound of formula (I) in accordance with the invention, a person skilled in the art may routinely select the form of intermediate which provides the best combination of features for this purpose. Such features include the melting point, solubility, processability and yield of the intermediate form and the resulting ease with which the product may be purified on isolation.

The compounds of the invention may be prepared by any method known in the art for the preparation of compounds of analogous structure. In particular, the compounds of the invention can be prepared by the procedures described by reference to the Schemes that follow, or by the specific methods described in the Examples, or by similar processes to either.

The skilled person will appreciate that the experimental conditions set forth in the schemes that follow are illustrative for cross coupling reactions, such as trialkylstannane, dihydroxyborane, dialkoxyborane or halozinc.

Where ratios of solvents are given, the ratios are by volume.

According to a first process, compounds of formula (I) wherein X is —CH$_2$O— may be prepared by the process illustrated in Scheme 1.

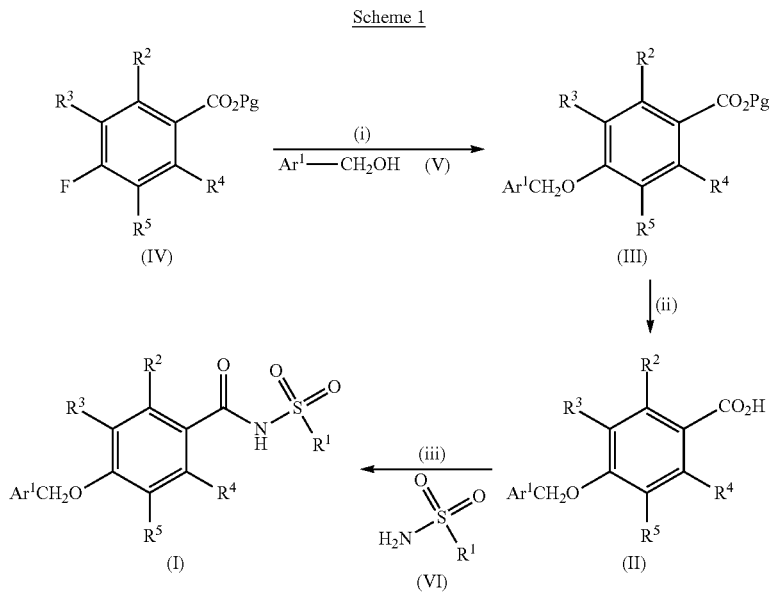

Scheme 1 of suitable conditions for effecting the transformations shown, and that it may be necessary or desirable to vary the precise conditions employed for the preparation of compounds of formula (I). It will be further appreciated that it may be necessary or desirable to carry out the transformations in a different order from that described in the schemes, or to modify one or more of the transformations, to provide the desired compound of the invention.

In addition, the skilled person will appreciate that it may be necessary or desirable at any stage in the synthesis of compounds of the invention to protect one or more sensitive groups, so as to prevent undesirable side reactions. In particular, it may be necessary or desirable to protect amino or carboxylic acid groups. The protecting groups used in the preparation of the compounds of the invention may be used in conventional manner. See, for example, those described in 'Greene's Protective Groups in Organic Synthesis' by Theodora W Greene and Peter G M Wuts, third edition, (John Wiley and Sons, 1999), in particular chapters 7 ("Protection for the Amino Group") and 5 ("Protection for the Carboxyl Group"), incorporated herein by reference, which also describes methods for the removal of such groups.

In the following general methods, X, R$^1$, R$^2$, R$^3$, R$^4$, R$^5$ and Ar$^1$ are as previously defined for a compound of the formula (I) unless otherwise stated. Pg is a suitable carboxylic acid ester protecting group, such as tert butyl, methyl, ethyl, or tolyl. Lg is a suitable leaving group, such as halo (e.g. Br) or a sulphonate (e.g. mesylate). W is —CO$_2$Pg or halo. M is an optionally substituted/ligated metal or boron group suitable Compounds of formula (I) can be prepared from compounds of formula (II) according to reaction step (iii) by activation of the acid group with reagents such as oxalyl chloride, propanephosphonic acid cyclic anhydride, carbonyl di-imidazole (CM), a uronium based peptide coupling agent or a carbodiimide reagent, followed by displacement with a sulphonamide of formula (VI) in the presence of a nucleophilic base, such as 4-dimethylaminopyridine. Typical conditions comprise N,N-dimethylaminopropyl-N'-ethylcarbodiimide and 4-dimethylaminopyridine in dichloromethane.

Compounds of formula (II) can be prepared by hydrolysis of the ester functional group in compounds of formula (III) by either acidic or basic methods according to step (ii). Preferred conditions are lithium hydroxide in THF/water at 60° C.

Compounds of formula (III) can be made from compounds of formula (IV) by a nucleophilic aromatic substitution reaction (SNAr) using an alcohol of formula (V) and base, according to step (i). Suitable conditions include, potassium carbonate in DMF or DMSO, sodium hydride in NMP or DMF, sodium hydroxide or potassium hydroxide in 1,4-dioxane and water or DMSO or potassium tert-butoxide in THF, between room temperature and 150° C. Preferred conditions comprise 1 equivalent of potassium tert-butoxide in THF/DMSO at 80° C. for 16 hours.

According to a second process, compounds of formula (I) wherein X is —CH$_2$O— may be prepared by the process illustrated in Scheme 2.

Scheme 2

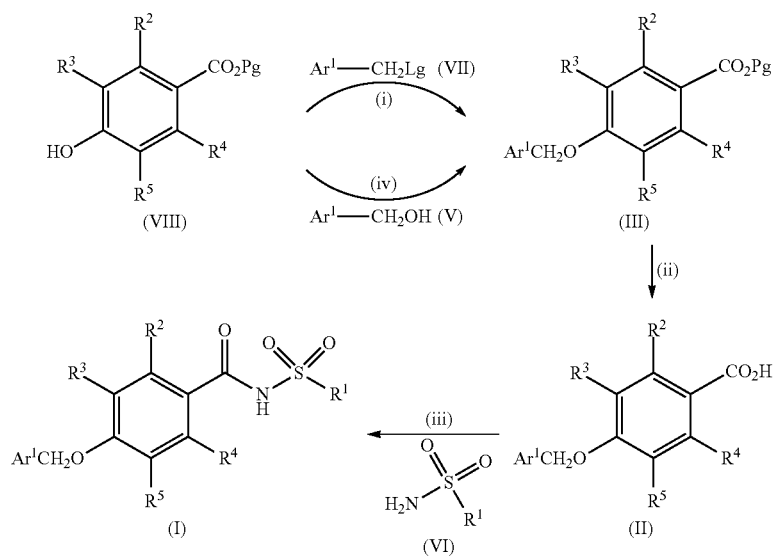

Compounds of formula (I) can be prepared from compounds of formulae (II) and (VI) according to reaction step (iii) under conditions described in Scheme 1 step (iii). Typical conditions comprise N,N-dimethylaminopropyl-N'-ethylcarbodiimide and 4-dimethylaminopyridine in dichloromethane.

Compounds of formula (II) can be prepared by hydrolysis of the ester functional group in compounds of formula (III) under conditions described in Scheme 1 step (ii). Preferred conditions are lithium hydroxide in tetrahydrofuran/water at 60° C.

Compounds of formula (III) can be made from compounds of formula (VIII) according to step (i) by a nucleophilic displacement (SN2) reaction with compounds of formula (VII) in the presence of a base. Suitable conditions include potassium carbonate in DMF or DMSO, sodium hydride in NMP or DMF, sodium hydroxide or potassium hydroxide in 1,4-dioxane and water or DMSO or potassium tert-butoxide in tetrahydrofuran at from room temperature to 150° C. Preferred conditions comprise sodium hydride in tetrahydrofuran at room temperature for 48 hours.

Compounds of formula (III) can also be made from compounds of formula (VIII) according to step (iv) by a Mitsunobu reaction with compounds of formula (V) in the presence of a phosphine and an azodicarboxylate. Suitable conditions include triphenylphosphine, such as polymer supported triphenylphosphine, and TMAD in DCM at from room temperature to 30° C. Preferred conditions comprise polymer supported triphenylphosphine and TMAD in DCM at 30° C. for 16 hours.

According to a third process, compounds of formula (I) wherein X is —OCH$_2$— may be prepared by the process illustrated in Scheme 3.

Compounds of formula (I) can be prepared from compounds of formulae (II) and (VI) according to reaction step (iv) under conditions described in Scheme 1 step (iii). Preferred conditions comprise N,N-dimethylaminopropyl-N'-ethylcarbodiimide and 4-dimethylaminopyridine in dichloromethane.

Compounds of formula (I) can also be prepared from compounds of formula (X, W=halo) according to reaction step (V) by carboamidation of the halide group using a carbonylation source. Conveniently the reaction is effected using a carbonyl source such as molybdenumhexacarbonyl or carbon monoxide, a palladium catalyst such as trans-bis(acetato)bis[o-(di-o-tolylphosphino)benzyl]dipalladium (II) or palladium (II) acetate, a phosphine ligand such as tri-tert-butylphosphonium tetrafluoroborate, a base such at triethylamine or 1,8-diazabicyclo[5.4.0]undec-7-ene and at 50-150° C. under pressure, or in a microwave for 10 minutes to 24 hours in a solvent such as tetrahydrofuran, NMP or 1,4-dioxane. Preferred conditions are molybdenumhexacarbonyl, trans-bis(acetato)bis[o-(di-o-tolylphosphino)benzyl]dipalladium(II), tri-tert-butylphosphonium tetrafluoroborate and 1,8-diazabicyclo[5.4.0]undec-7-ene in 1,4-dioxan in a microwave at 140° C. for 15 minutes.

Scheme 3

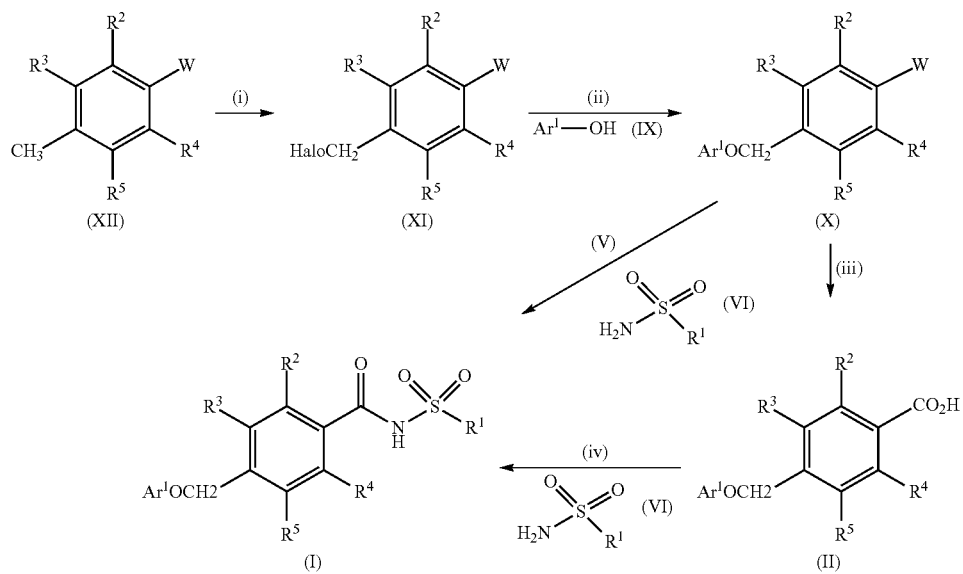

Compounds of formula (II) can be prepared from compounds of formula (X, W=—CO₂Pg) according to step (iii) under conditions described in Scheme 1 step (ii). Preferred conditions are lithium hydroxide in tetrahydrofuran/water at 55° C. for 6 hours.

Compounds of formula (X) can be prepared from compounds of formula (XI) according to step (ii) by nucleophilic displacement of the halogen group by an alcohol of formula (IX). Conveniently the reaction is carried out in the presence of an auxiliary base such as triethylamine, diisopropylethylamine, potassium or sodium carbonate, sodium or potassium hydroxide in a variety of solvents such as NMP, 1,4-dioxane, acetone, DMSO or DMF from room temperature to 150° C. Preferred conditions are potassium carbonate in DMF at 60° C.

Compounds of formula (XI) can be prepared by halogenation of the methyl group in compounds of formula (XII) according to step (i) using a halogenating reagent. Conveniently halogenation is effected using a reagent such as N-bromosuccinimide, N-iodosuccinimide, bromine, iodine, sodium bromate, often with an initiator such as dibenzoyl peroxide or azobisisobutyronitrile in a variety of solvents such as carbon tetrachloride, 1,2-dichloroethane, chloroform, dichloromethane, ethyl acetate, acetic acid and water. Preferred conditions are N-bromosuccinimide and dibenzoyl peroxide in carbon tetrachloride at reflux.

According to a fourth process, compounds of formula (I) wherein X is —OCH₂— may be prepared by the process illustrated in Scheme 4.

Scheme 4

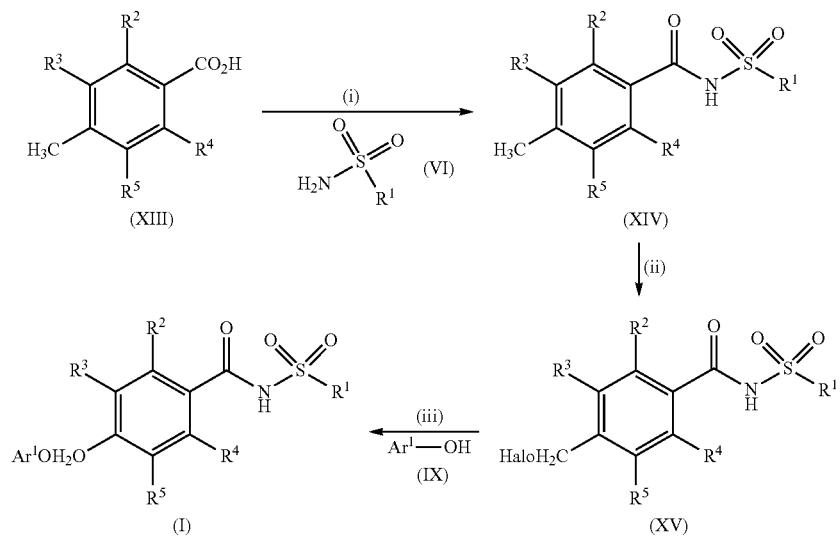

Compounds of formula (I) can be prepared from compounds of formula (XV) (wherein halo is I or Br) according to step (iii) by displacement of halo by an alcohol of formula (IX) under conditions described above in Scheme 3 step (ii). Preferred conditions are potassium carbonate in DMSO at room temperature.

Compounds of formula (XV) can be prepared by halogenation of the methyl group in compounds of formula compound (XIV) according to step (ii) under conditions described above in Scheme 3 step (i). Preferred conditions are N-bromosuccinimide in the presence of azobisisobutyronitrile in 1,2-dichloroethane at reflux.

Compounds of formula (XIV) can be made from compounds of formulae (XIII) and (VI) according to reaction step (i) under conditions described in Scheme 1 step (iii).

Preferred conditions comprise propanephosphonic acid cyclic anhydride and diisopropylethylamine in tetrahydrofuran.

Compounds of formulae (IV), (V), (VI), (VII), (VIII), (IX), (XII) and (XIII) are either commercially available, known from the literature, easily prepared by methods well known to those skilled in the art, or can be made according to preparations described herein.

All new processes for preparing compounds of formula (I), and corresponding new intermediates employed in such processes, form further aspects of the present invention.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™ Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 µg to 100 mg of the compound of formula (I). The overall daily dose will typically be in the range 1 µg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia-Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders;
erythermalgia; and
orofacial pain, including dental pain, otic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of formula (I), or a pharmaceutically acceptable salt thereof, as defined above, may be administered in combination with one or more agents selected from:
an alternative Nav1.7 channel modulator, such as another compound of the present invention or a compound disclosed in WO 2009/012242;
an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);
an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;
a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene-1-carboxamide);
an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5\text{-HT}_{1B/1D}$ agonist such as eletriptan, sumatriptan, naratriptan, zolmitriptan or rizatriptan;

a $5\text{-HT}_{2A}$ receptor antagonist such as R(+)-alpha-(2,3-dimethoxy-phenyl)-1-[2-(4-fluorophenylethyl)]-4-piperidinemethanol (MDL-100907);

a $5\text{-HT}_3$ antagonist, such as ondansetron;

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-Nyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;
a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;
an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl] thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino) ethyl]phenyl]thiophene-2-carboxamidine, or guanidinoethyldisulfide;
an acetylcholinesterase inhibitor such as donepezil;
a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;
a microsomal prostaglandin E synthase type 1 (mPGES-1) inhibitor;
a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870; and
a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3, 5-trimethyl-6-(3-pyridylmethyl),1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl) acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

In the non-limiting Examples and Preparations that are set out later in the description, and in the aforementioned Schemes, the following the abbreviations, definitions and analytical procedures may be referred to:

AcOH is acetic acid,
$Cs_2CO_3$ is caesium carbonate;
$Cu(acac)_2$ is copper (II) acetylacetonate;
CuI is copper (I) iodide;
$Cu(OAc)_2$ is copper (II) acetate;
DAD is diode array detector;
DCM is dichloromethane; methylene chloride;
DIPEA is N-ethyldiisopropylamine, N,N-diisopropylethylamine;
DMAP is 4-dimethylaminopyridine;
DMF is N,N-dimethylformamide;
DMSO is dimethyl sulphoxide;
EDCl is 1-(3-dimethylaminopropyl)-3-ethylcarbodiimide hydrochloride;
EDTA is ethylenediaminetetraacetic acid;
ELSD is evaporative light scattering detection;
$Et_2O$ is diethyl ether;
EtOAc is ethyl acetate;
EtOH is ethanol;
HATU is 2-(1H-7-azabenzotriazol-1-yl)-1,1,3,3-tetramethyluronium hexafluorophosphate;
HCl is hydrochloric acid;
IPA is isopropanol;
$Ir_2(OMe)_2COD_2$ is bis(1,5-cyclooctadiene)di-μ-methoxydiiridium (I);

K$_2$CO$_3$ is potassium carbonate;
KHSO$_4$ is potassium hydrogen sulphate;
KOAc is potassium acetate;
KOH is potassium hydroxide;
K$_3$PO$_4$ is potassium phosphate tribasic;
LCMS is liquid chromatography mass spectrometry (Rt=retention time)
LiOH is lithium hydroxide;
MeOH is methanol;
MgSO$_4$ is magnesium sulphate;
NaH is sodium hydride;
NaHCO$_3$ is sodium hydrogencarbonate;
Na$_2$CO$_3$ is sodium carbonate;
NaHSO$_3$ is sodium bisulphate;
NaHSO$_4$ is sodium hydrogensulphate;
NaOH is sodium hydroxide;
Na$_2$SO$_4$ is sodium sulphate;
NH$_4$Cl is ammonium chloride;
NMP is N-Methyl-2-pyrrolidone;
Pd/C is palladium on carbon;
Pd(PPh$_3$)$_4$ is palladium tetrakis;
Pd(dppf)$_2$Cl$_2$ is [1,1'-bis(diphenylphosphino)ferrocene]dichloropalladium(II), complex with dichloromethane;
TBME is t-butyl methyl ether;
THF is tetrahydrofuran;
THP is tetrahydropyran;
TLC is thin layer chromatography;
TMAD is N,N,N'N'-tetramethylazodicarboxylate; and
WSCDI is 1-(3-dimethylaminopropyl)-3-ethylcarbodiimide hydrochloride.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; dd, doublet of doublets; t, triplet; q, quartet; m, multiplet; br, broad. The following abbreviations have been used for common solvents: CDCl$_3$, deuterochloroform; d$_6$-DMSO, deuterodimethylsulphoxide; CD$_3$OD, deuteromethanol; and Acetone-d$_6$, deuterated acetone.

Mass spectra, MS (m/z), were recorded using either electrospray ionisation (ESI) or atmospheric pressure chemical ionisation (APCI). When relevant, m/z data provided may include isotopes $^{35}$Cl, $^{37}$Cl, $^{79}$Br, $^{81}$Br and combinations there of.

Automated Preparative High Performance Liquid Chromatography (Auto-HPLC)

Certain compounds of the Examples and Preparations were purified using Automated Preparative High Performance Liquid Chromatography (HPLC). Reversed-phase HPLC conditions were either on Fraction Lynx systems or on a Trilution system.

In the case of the Fractionlynx system, samples were submitted dissolved in 1 mL of DMSO. Depending on the nature of the compounds and the results of a pre-analysis, the purification was performed under either acidic ('A-HPLC'), or basic ('B-HPLC') conditions at ambient temperature. A-HPLC was carried out on a Sunfire Prep C18 OBD column (19×100 mm, 5 µm). B-HPLC was carried out on an Xterra Prep MS C18 (19×100 mm, 5 µm), both from Waters. A flow rate of 18 mL/min was used with mobile phase A: water+ 0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 30 v Capillary: 3.20 kv
ES− Cone voltage: −30 v Capillary: −3.00 kv
Desolvation gas: 600 L/hr
Source Temp: 120° C.
Scan range 150-900 Da The fraction collection was triggered by both MS and ELSD.

Quality control (QC) analysis was performed using a LCMS method. Acidic runs were carried out on a Sunfire C18 (4.6×50 mm, 5 µm), basic runs were carried out on a Xterra C18 (4.6×50 mm, 5 µm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was ammonia. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:
ES+ Cone voltage: 25 v Capillary: 3.30 kv
ES− Cone voltage: −30 v Capillary: −2.50 kv
Desolvation gas: 800 L/hr
Source Temp: 150° C.
Scan range 160-900 Da Where the reversed-phase Trilution system was used (T-HPLC) the conditions were as follows:
Mobile phase A: 0.1% formic acid in water
Mobile phase B: 0.1% formic acid in acetonitrile
Column: Phenomenex C18 Luna 21.5 mm×15 cm with 5 micron particle size
Gradient: 95-5% A over 15 min, 15 min hold, 15 ml/min flow rate
UV: 200 nm-400 nm
Temperature: Room temperature
Liquid Chromatography Mass Spectrometry Unless carried out by Auto-HPLC (under conditions of A-HPLC or B-HPLC) as described just above, or as specifically set out in the Examples and Preparations that follow, LCMS conditions were run according to one of the conditions given below (where ratios of solvents are given, the ratios are by volume):
Acidic 2 Minute LCMS
Mobile phase A: 0.1% formic acid in water
Mobile phase B: 0.1% formic acid in 70% methanol: 30% isopropanol Column: C18 phase Phenomenex 20×4.0 mm with 3 micron particle size Gradient: 98-10% A over 1.5 min, 0.3 min hold, 0.2 re-equilibration, 2 ml/min flow rate UV: 210 nm-450 nm DAD Temperature: 75° C.

Or

Mobile phase A: 0.1% formic acid in water

Mobile phase B: 0.1% formic acid in acetonitrile

Column: C18 phase Phenomenex 20×4.0 mm with 3 micron particle size

Gradient: 70-2% A over 1.5 min, 0.3 min hold, 0.2 re-equilibration, 1.8 ml/min flow rate UV: 210 nm-450 nm DAD Temperature: 75° C.

Acidic 4.5 Minute LCMS

Mobile phase A: 0.05% formic acid in water

Mobile phase B: acetonitrile

Column: Phenomenex Gemini C18 45×45 mm with 5 micron particle size

Gradient: 80-50% A over 0.5 min, 50-2% A over 3 min, 1 min hold, 0.2 min re-equilibration, 2.0 ml/min flow rate UV: 220 nm-254 nm DAD Temperature: 40° C.

Acidic 8 Minute LCMS

Mobile phase A: 0.05% formic acid in water

Mobile phase B: acetonitrile

Column: Phenomenex Gemini C18 45×45 mm with 5 micron particle size

Gradient: 80-50% A over 0.5 min, 50-2% A over 3 min, 4.5 min hold, 0.2 min re-equilibration, 2.0 ml/min flow rate UV: 220 nm-254 nm DAD Temperature: 40° C.

Acidic 6 Minute LCMS

Mobile phase A: 0.1% formic acid in water

Mobile phase B: 0.1% formic acid in acetonitrile

Column: C18 phase Waters Sunfire 50×4.6 mm with 5 micron particle size

Gradient: 95-5% A over 3 min, 1 min hold, 2 min re-equilibration, 1.5 ml/min flow rate UV: 210 nm-450 nm DAD Temperature: 50° C.

Basic 6 Minute LCMS

Mobile phase A: 0.1% ammonium hydroxide in water

Mobile phase B: 0.1% ammonium hydroxide in acetonitrile

Column: C18 phase Fortis 50×4.6 mm with 5 micron particle size

Gradient: 95-5% A over 3 min, 1 min hold, 2 min re-equilibration, 1 ml/min flow rate UV: 210 nm-450 nm DAD Temperature: 50° C.

Acidic 30 Minute LCMS

Mobile phase A: 0.1% formic acid in water

Mobile phase B: 0.1% formic acid in acetonitrile

Column: Phenomenex C18 phase Gemini 150×4.6 mm with 5 micron particle size

Gradient: 98-2% A over 18 min, 2 min hold, 1 ml/min flow rate

UV: 210 nm-450 nm DAD

Temperature: 50° C.

Basic 30 Minute LCMS

Mobile phase A: 10 mM ammonium acetate in water

Mobile phase B: 10 mM ammonium acetate in methanol

Column: Phenomenex Phenyl Hexyl 150×4.6 mm with 5 micron particle size

Gradient: 98-2% A over 18 min, 2 min hold, 1 ml/min flow rate

UV: 210 nm-450 nm DAD

Temperature: 50° C.

In the tabulated experimental details that follow, the Examples and Preparations were prepared according to the corresponding reference method (i.e. Method A, Method B, Preparation 28, and so on). The skilled person will appreciate that, in the synthesis of any specific Example or Preparation, it may be desirable to make minor variations to the reaction conditions of the reference method (e.g. with regard to solvent, temperature and so on).

EXAMPLE 1

Illustrates Method F

5-Chloro-4-[(3,4-dichlorophenoxy)methyl]-2-fluoro-N-(methylsulfonyl)benzamide

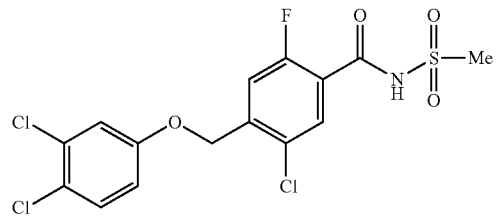 [SMILES: CS(=O)(=O)NC(=O)c1cc(Cl)c(COc2ccc(Cl)c(Cl)c2)cc1F]

A 5 mL microwave reaction vial was charged with 1-bromo-5-chloro-4-((3,4-dichlorophenoxy)methyl)-2-fluorobenzene (Preparation 1, 206 mg, 0.54 mmol), molybdenumhexacarbonyl (139 mg, 0.53 mmol), trans-bis(acetato)bis[o-(di-o-tolylphosphino)benzyl]dipalladium(II) (25.9 mg, 0.028 mmol), tri-tert-butylphosphonium tetrafluoroborate (16.8 mg, 0.058 mmol), methanesulphonamide (159 mg, 1.67 mmol) and 1,8-diazabicyclo[5.4.0]undec-7-ene (0.23 mL, 1.56 mmol) in 1,4-dioxane (1.80 mL). The vessel was sealed under air and exposed to microwave irradiation at 140° C. for 15 minutes. Once the reaction had cooled to room temperature the reaction mixture was then concentrated in vacuo to afford a brown oil. The oil was then passed through a short plug of silica eluting with 5% methanol in dichloromethane and fractions containing product were combined and concentrated in vacuo to afford an off white solid (266 mg). A portion of this material (190 mg) was purified by reverse phase column chromatography using the ISCO™ system (30 g ISCO C-18 cartridge) using a gradient of water/0.01% formic acid/acetonitrile to 0.01% formic acid/water as eluant to give the title compound (50 mg, 22%) as a white solid.

$^1$H NMR (400 MHz, CDCl$_3$): δ 3.40 (s, 3H), 5.31 (s, 2H), 7.13 (dd, 1H), 7.36 (d, 1H), 7.52 (d, 1H), 7.59 (d, 1H), 7.89 (d, 1H),

LCMS Rt=4.05 minutes MS m/z 426 [M−H]−

EXAMPLE 2

Illustrates Method D

4-{[3-Chloro-4-(trifluoromethyl)phenoxy]methyl}-2,5-difluoro-N-(methylsulfonyl)benzamide

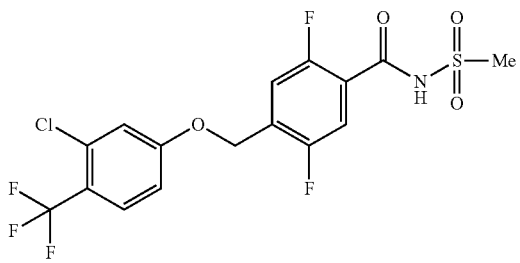 [SMILES: CS(=O)(=O)NC(=O)c1cc(F)c(COc2ccc(C(F)(F)F)c(Cl)c2)cc1F]

A solution of 3-chloro-4-(trifluoromethyl)phenol (Preparation 5, 50 mg, 0.26 mmol), 4-(bromomethyl)-2,5-difluoro-N-(methylsulfonyl)benzamide (Preparation 4, 84 mg, 0.26 mmol) and potassium carbonate (71 mg, 0.51 mmol) in dimethyl sulfoxide (5 mL) was stirred at room temperature for 16 hours. A 2M aqueous solution of hydrogen chloride was added to the reaction mixture. The resulting precipitate was filtered, washed with diethyl ether (5 mL) and dried. The material was purified by reverse phase column chromatography (12 g C-18 biotage cartridge; eluents: MeCN+0.1% formic acid, and H$_2$O+0.1% formic acid; Gradient: 30% MeCN, followed by gradient to 100% MeCN, 100% MeCN. Fractions containing product were combined and concentrated in vacuo to afford the title compound as a colourless solid (65 mg, 56%).

$^1$H NMR (400 MHz, d$_6$-DMSO): δ 3.30 (s, 3H), 5.35 (s, 2H), 7.20 (m, 1H), 7.48 (m, 1H), 7.60 (m, 2H), 7.80 (m, 1H).
LCMS Rt=4.03 minutes MS m/z 442, 444 [M−H]−

EXAMPLE 3

Illustrates Method B

4-[(3,4-Dichlorobenzyl)oxy]-Nethylsulfonyl)benzamide

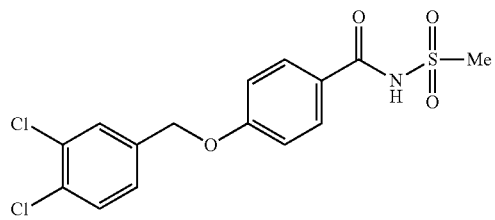 [SMILES: CS(=O)(=O)NC(=O)c1ccc(OCc2ccc(Cl)c(Cl)c2)cc1]

A solution of 4-[(3,4-dichlorobenzyl)oxy]benzoic acid (Preparation 9, 0.62 g, 2.10 mmol), 1-(3-dimethylaminopropyl)-3-ethylcarbodiimide hydrochloride (1.2 g, 6.3 mmol), 4-dimethylaminopyridine (0.77 g, 6.30 mmol) and diisopropylethylamine (2.1 mL; 12.51 mmol) in dichloromethane (10 mL) was stirred at room temperature for 15 minutes under nitrogen. Methane sulphonamide (1.0 g, 10.4 mmol) was added and the reaction mixture left to stir at room temperature under nitrogen for 36 hours. Upon completion, water (20 mL) was added and extracted into dichloromethane. The organic layer was then washed with hydrochloric acid (0.5 M, 25 mL) then brine (25 mL), dried over magnesium sulphate, filtered and evaporated. The resulting residue was triturated with dichloromethane to give the title compound (275 mg, 35%) as a white solid.

$^1$H NMR (400 MHz, MeOD-d4): δ 3.34 (s, 3H), 5.16 (s, 2H), 7.09 (m, 1H), 7.11 (m, 1H), 7.38 (m, 1H), 7.53 (m, 1H), 7.62 (m, 1H), 7.88 (m, 1H), 7.90 (m, 1H).
LCMS Rt=1.70 minutes MS m/z 375 [MH]+

EXAMPLE 4

N-(Methylsulfonyl)-4-({4-[1-methyl-3-(trifluoromethyl)-1H-pyrazol-5-yl]phenoxy}methyl)benzamide diethylamine salt

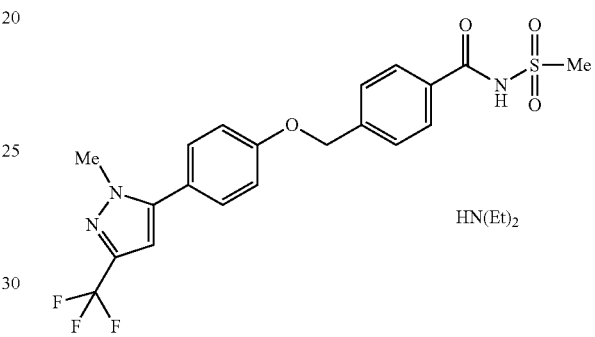

To a solution of methyl 4-(bromomethyl)benzoate (114 mg, 0.5 mmol) in anhydrous N,N-dimethylformamide (1.05 mL) in an ArQule™ vial was added potassium carbonate (138 mg, 1.0 mmol) followed by a solution of 4-[1-methyl-3-(trifluoromethyl)-1H-pyrazol-5-yl]phenol (Preparation 6, 121 mg, 0.5 mmol) in N,N-dimethylformamide (1.5 mL). The reaction vessel was sealed and heated to 60° C. with stirring for 16 hours and then cooled to room temperature. The reaction mixture was partitioned between diethyl ether (5 mL) and water (5 mL) and the organic extracts were concentrated in vacuo. The crude residue was dissolved in tetrahydrofuran (2 mL), lithium hydroxide (60 mg, 2.5 mmole) added and water (1 mL). The ArQule™ vial was sealed and the reaction mixture heated to 55° C. with stirring for 6 hours. The resulting solution was diluted with water (5 mL) and washed with diethyl ether (3 mL). The aqueous extract was then acidified with aqueous 2 M hydrogen chloride solution and extracted with ethyl acetate (5 mL). The organic extracts were separated and evaporated in vacuo. The crude residue was dissolved in dichloromethane (2.5 mL) to which 4-dimethylaminopyridine (122 mg, 1.0 mmol) and 1-(3-dimethylaminopropyl)-3-ethylcarbodiimide hydrochloride (192 mg, 1.0 mmol) were added. The reaction mixture was stirred in a sealed vessel until solubilised, then methanesulphonamide (95 mg, 1.0 mmole) was added. The reaction vessel was sealed and heated to 40° C. with stirring overnight. The reaction mixture was diluted with further dichloromethane (5 mL), and partitioned with 2 M aqueous hydrogen chloride solution (5 mL). The organic extract was passed through a phase separation cartridge, and evaporated in vacuo. The crude residue was dissolved in dimethylsulphoxide (50 mg/mL) and purified by B-HPLC to afford the title compound (50.6 mg, 22%) as the diethylamine salt.
LCMS Rt=2.45 minutes MS m/z 452, 454 [M−H]−

EXAMPLE 5

Illustrates Method H

3-Cyano-N-(methylsulfonyl)-4-(1-naphthylmethoxy)benzamide

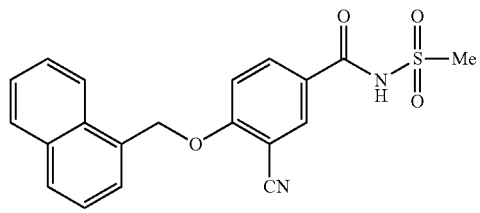 [SMILES: CS(=O)(=O)NC(=O)c1ccc(OCc2cccc3ccccc23)c(C#N)c1]

To a solution of 1-naphthylmethanol (19.8 mg, 0.13 mmol) in anhydrous tetrahydrofuran were added potassium tert butoxide (0.14 mL, 1 M solution in anhydrous tetrahydrofuran 0.14 mmol) followed by a solution of methyl 3-cyano-4-fluorobenzoate (22.4 mg, 0.13 mmol) in dimethylsulfoxide (0.1 mL). The reaction mixture was shaken at 80° C. for 16 hours, evaporated in vacuo, and water (1 mL) was added. The mixture was extracted with ethyl acetate (3×1 mL) and the combined organic extracts were dried over anhydrous sodium sulphate, filtered and evaporated in vacuo. The residue was dissolved in tetrahydrofuran (0.7 mL), an aqueous solution of lithium hydroxide (0.7 mL, 1 M, 0.70 mmol) added and the mixture was shaken at 60° C. for 2 hours. The reaction mixture was evaporated in vacuo and hydrochloric acid (0.70 mL, 1 M, 0.70 mmol) was added. The resulting mixture was extracted with ethyl acetate (3×1 mL) and the combined organic extracts were dried over anhydrous sodium sulphate, filtered and evaporated in vacuo. To the residue were added methanesulfonamide (27 mg, 0.28 mmol), a solution of 4-dimethylaminopyridine (24.4 mg, 0.20 mmol) and 1-(3-dimethylaminopropyl)-3-ethylcarbodiimide hydrochloride (38.3 mg, 0.20 mmol) in dichloromethane (1 mL). The mixture was shaken for 16 hours at 30° C. and then evaporated in vacuo. The residue was purified on an HPLC column (Grace Vydac C18 200*20 mm*5 mm column) with a gradient of acetonitrile/water (0.1% trifluoroacetic acid) to yield the title compound (4.25 mg, 9%).

LCMS Rt=3.14 minutes MS m/z=381 [MH]$^+$

LCMS Method:

| | |
|---|---|
| Column | Welch XB-C18 2.1 × 50 mm 5 µm |
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 1% B |
| Time 0.00 mins | 1% B |
| Time 0.60 mins | 5% B |
| Time 4.00 mins | 100% B |
| Time 4.30 mins | 1% B |
| Time 4.70 mins | 1% B |
| Flow rate | 0.8 ml/min |
| Injection volume | 2 µl |
| Agilent 1200 HPLC/1956 MSD/SEDEX 75 ELSD | |
| Ionization Mode | API-ES |
| Polarity | Positive |

EXAMPLE 6

3-Chloro-N-(methylsulfonyl)-4-{[2-(trifluoromethoxy)benzyl]oxy}benzamide

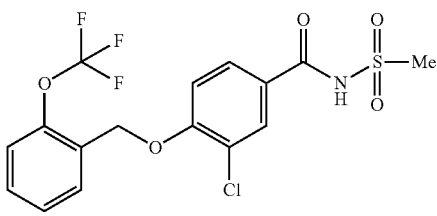 [SMILES: CS(=O)(=O)NC(=O)c1ccc(OCc2ccccc2OC(F)(F)F)c(Cl)c1]

The title compound was prepared analogous to the previous compound (example 5) using [2-(trifluoromethoxy)phenyl]methanol (24.0 mg, 0.13 mmol) and methyl 3-chloro-4-fluorobenzoate (23.6 mg, 0.13 mmol). The title compound (8.72 mg, 16%) was isolated by purification on an HPLC column (Grace Vydac C18 250*20 mm*5 µm) using a gradient of acetonitrile/water (0.1% trifluoroacetic acid).

LCMS Rt=3.23 minutes MS m/z=424 [MH]+

LCMS Method

| | |
|---|---|
| Column | Welch XB-C18 2.1 × 50 mm 5 µm |
| Temperature | 50° C. |
| Mobile Phase A | 0.0375% trifluoroacetic acid in water |
| Mobile Phase B | 0.01875% trifluoroacetic acid in acetonitrile |
| Gradient - Initial | 10% B |

EXAMPLE 7

Illustrates Method A

3-Chloro-4-[(3,4-difluorobenzyl)oxy]-Nethylsulfonyl)benzamide

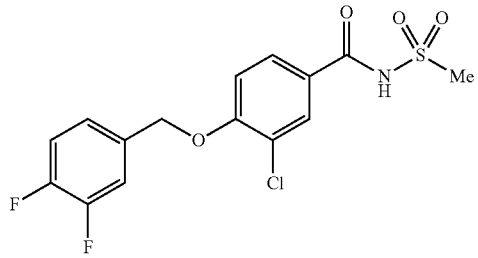 [SMILES: CS(=O)(=O)NC(=O)c1ccc(OCc2ccc(F)c(F)c2)c(Cl)c1]

3-Chloro-4-[(3,4-difluorobenzyl)oxy]benzoic acid (Preparation 11, 100 mg, 0.34 mmol) and 2-(1H-7-azabenzotriazol-1-yl)-1,1,3,3-tetramethyluronium hexafluorophosphate (148 mg, 0.37 mmol) were suspended in anhydrous DCM. N,N-diisopropylethylamine (0.19 mL, 1.08 mmol) was added and the reaction mixture was stirred at room temperature for 1 hour. To the clear solution, methanesulphonamide (98 mg, 1.01 mmol) was added and the reaction mixture was stirred at room temperature for 18 hours. The mixture was evaporated in vacuo and a portion was purified by preparative HPLC to yield the title compound.

LCMS Rt=2.78 minutes MS m/z 374 [M-H]–

EXAMPLE 8

Illustrates Method C

4-[(3-Methoxyphenoxy)methyl]-Nethylsulfonyl)benzamide diethylamine salt

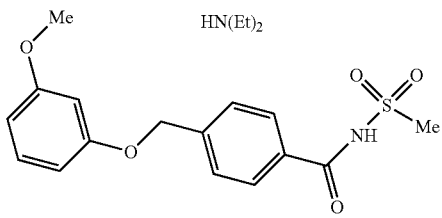 [SMILES: COc1cccc(OCc2ccc(C(=O)NS(C)(=O)=O)cc2)c1 ; "HN(Et)2"]

Into an ArQule Vial™ was added potassium carbonate (138 mg, 1 mmol), methyl 4-(bromomethyl)benzoate (114 mg, 0.5 mmol) in DMF (1.05 mL) and 3-methoxyphenol (62 mg, 0.5 mmol) in DMF (1.5 mL). The vial was sealed and heated to 65° C. with internal stirring for 6 hours, then allowed to cool to room temperature for 18 hours. The reaction mixture was partitioned with EtOAc (3 mL) and water (3 mL), the organic layer was transferred to another ArQule Vial™ and then evaporated. THF (2.5 mL) was added, followed by an aqueous solution of lithium hydroxide (0.5 mL, 60 mg, 2.5 mmol). The mixture was stirred in the sealed vial at 55° C. for 18 hours. Water (3 mL) was then added and the aqueous was then washed with diethyl ether (1 mL), acidified with an aqueous solution of hydrochloric acid (2 M, 1 mL) and extracted with EtOAc. The combined organics were concentrated in vacuo. To the crude residues (in an ArQule™ vial) were added N,N-dimethylpyridin-4-amine (122 mg, 2 mmol) in DCM (1 mL), N-[3-(dimethylamino)propyl]-N'-ethylcarbodiimide hydrochloride (192 mg, 2 mmol) in DCM (1 mL) and methanesulphonamide (95 mg, 2 mmol) in DCM (1 mL). The reaction mixture was sealed and stirred at room temperature for 18 hours, then diluted with DCM (2 mL) and partitioned with an aqueous solution of hydrochloric acid (2 M, 2 mL). The organic layer was then passed through a phase separation Cartridge™ and air dried for 18 hours. The resulting crude residue (110 mg, 66%) was dissolved in DMSO (50 mg/mL) and purified by preparative HPLC to afford the title compound (50.1 mg, 30%) as the diethylamine salt.

LCMS Rt=3.31 minutes MS m/z 336 [MH]+, 334 [M−H]−

Preparative Basic Conditions

Column: XTerra C18, 5 um 19×100 mm

Temperature: Ambient

Detection: ELSD-MS

Fractionlynx 4

Injection Volume: 1000 uL

Flow Rate: 18 mL/min

Mobile Phase: A: $H_2O$+0.1% DEA, B: MeCN+0.1% DEA

Gradient (Time/mins, % B)—(0-1, 5), (1-7, 5-98), (7-9, 98), (9-9.1, 98-5), (9.1-10, 5)

EXAMPLE 9

Illustrates Method E

4-[(3,4-Dichlorobenzyl)oxy]-2,5-difluoro-N-(methylsulfonyl)benzamide

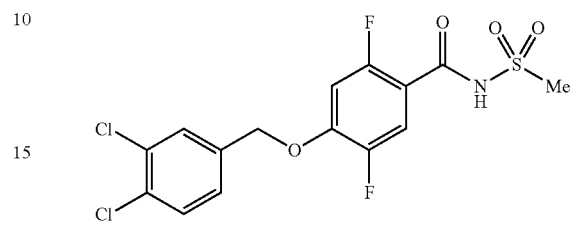

To a solution of 2,5-Difluoro-4-hydroxy-N-(methylsulfonyl)benzamide (Preparation 18 10.6 g, 42.2 mmol) in DMSO (53 mL) was added 4-(bromomethyl)-1,2-dichlorobenzene (10.63 g, 44.3 mmol) and potassium carbonate (11.66 g, 84.4 mmol) and the reaction stirred at ambient temperature for 18 hours. The reaction was quenched with aqueous hydrogen chloride solution (1 M, 100 mL) and water (100 mL). The resulting off-white precipitate was stirred at room temperature for 1 hour, filtered and washed with water (3×100 mL). The resulting pale yellow solid was suspended in acetone (106 mL) and heated at reflux for 1 hour. The suspension was then cooled to room temperature and filtered to yield the first crop of the crude title compound as a white solid (11.6 g, 67%).

An identical preparation was conducted on 4-[(3,4-dichlorobenzyl)oxy]-2,5-difluorobenzamide (18.0 g, 71.7 mmol) to furnish the second crop of the crude title compound as a white solid (14.0 g, 47.6%).

The combined white solids were suspended in acetonitrile and heated at reflux to obtain a solution. The solution was allowed to cool to room temperature and concentrated in vacuo to furnish the title compound as an off-white solid (25.6 g, 54.8%).

$^1$H NMR (400 MHz, $d_6$-DMSO): δ 3.35 (s, 3H), 5.3 (s, 2H), 7.39 (dd, 1H), 7.49 (d, 1H), 7.62 (dd, 1H), 7.70 (d, 1H), 7.78 (s, 1H).

EXAMPLE 10

4-(3-Chloro-4-(trifluoromethyl)benzyloxy)-2,5-difluoro-N-(methylsulfonyl)benzamide

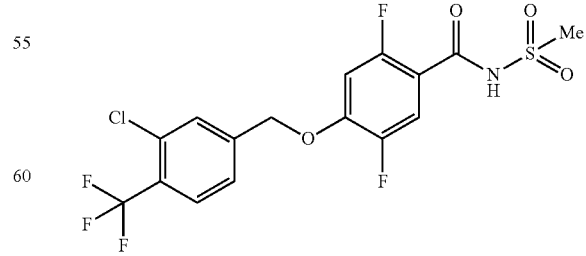

To a solution of 1-bromo-4-(3-chloro-4-(trifluoromethyl)benzyloxy)-2,5-difluorobenzene (Preparation 19, 200 mg, 0.50 mmol) in 1,4-dioxane (2.0 mL) were added molybdenumhexacarbonyl (142 mg, 0.50 mmol), trans-bis(acetate)bis [(o-(di-o-tolylphosphino)benzyl]dipalladium (II) (23 mg, 0.025 mmol), tri-tertbutylphosphonium tetrafluoroborate (14 mg, 0.050 mmol), 1,8-diazobicylco[5.4.0]undec-7-ene (223 μL, 1.49 mmol) and methanesulphonamide (142 mg, 1.49 mmol). The reaction mixture was heated in the microwave at 140° C. for 20 minutes. The solvent was then evaporated in vacuo to yield a brown oil, which was dissolved in DCM (20 mL). Potassium hydrogen sulphate (30 mL) was added and the organic layer separated. The aqueous layer was extracted with DCM (2×20 mL), then the combined organics were washed with brine (50 mL), filtered through a phase separator and reduced to dryness to give a brown solid, which was purified by silica gel chromatography eluting with 2 to 10% methanol in DCM to yield the title compound as white solid (57 mg, 26%).

$^1$H NMR (400 MHz, d$_6$-DMSO): 3.32 (s, 3H), 5.38 (s, 2H), 7.36 (dd, 1H), 7.60-7.64 (m, 2H), 7.80 (m, 1H), 7.91 (d, 1H), 12.07 (br, 1H).

LCMS Rt=3.38 minutes MS m/z 442 [M−H]−

EXAMPLE 11

Illustrates Method G 4-((3,4-Dichlorophenoxy)methyl)-2,5-difluoro-N-(methylsulfonyl)benzamide Diethylamine salt

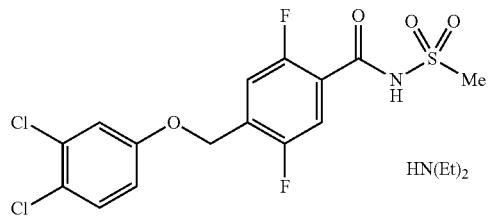 [SMILES: CS(=O)(=O)NC(=O)c1cc(F)c(COc2ccc(Cl)c(Cl)c2)cc1F ; "HN(Et)2"]

To 4-((3,4-dichlorophenoxy)methyl)-2,5-difluorobenzamide (Preparation 24, 60 mg, 0.18 mmol) in THF (2 mL) was added a THF solution of lithium hexamethyldisilazide (1 M, 0.362 mL, 0.362 mmol) over 2 minutes. After stirring for 15-20 minutes, methanesulphonyl chloride (0.028 mL, 0.362 mmol) was added and the solution was stirred for 18 hours at room temperature. The reaction mixture was then diluted with EtOAc and washed twice with water. The organic layer was dried over sodium sulphate and evaporated to yield a yellow oil (65 mg), which was purified by preparative HPLC to yield the title compound.

LCMS Rt=4.01 minutes MS m/z 408 [M−H]−

EXAMPLE 12

4-[(3,4-Dichlorobenzyl)oxy]-2-methoxy-N-(methylsulfonyl)benzamide

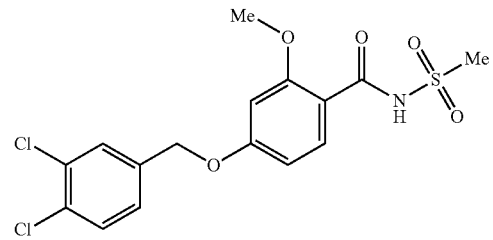 [SMILES: COc1cc(OCc2ccc(Cl)c(Cl)c2)ccc1C(=O)NS(C)(=O)=O]

To a solution of methanesulphonamide (79.6 mg, 0.837 mmol) and bis[(2,2-dimethylpropanoyl)oxy](phenyl)-lambda-3-iodane (630.0 mg, 1.553 mmol) in isopropyl acetate (6.0 mL) was added 4-[(3,4-dichlorobenzyl)oxy]-2-methoxybenzaldehyde (Preparation 25, 300.0 mg, 0.963 mmol) and 4 Å molecular sieves (500.0 mg). The reaction mixture was stirred for 5 minutes producing a thick suspension. 3,3'-(1,3-Phenylene)bis(2,2-dimethylpropanoic acid)-dirhodium(Rh—Rh) (2:1) (13 mg, 0.017 mmol) was added in one portion and the resulting mixture stirred at room temperature for 10 minutes. 1,2-dichloroethane (5 mL) was then added producing a green solution, which was stirred for further 18 hours under a nitrogen atmosphere at room temperature. The reaction mixture was then concentrated in vacuo and partitioned between DCM and aqueous solution of hydrochloric acid (2 M). The combined organics were dried through a phase separation Cartridge™ and evaporated in vacuo. The resulting residue was purified by silica gel chromatography eluting with 0 to 60% EtOAc in heptane to yield the title compound as pale yellow gum which solidified upon standing (140 mg, 41% yield):

$^1$H NMR (400 MHz, CDCl$_3$): δ 3.40 (s, 3H), 4.00 (s, 3H), 5.08 (s, 2H), 6.58 (d, 1H), 6.68 (dd, 1H), 7.26 (dd, 1H+CDCl$_3$ peak), 7.48 (d, 1H), 7.54 (d, 1H), 8.16 (d, 1H), 10.03 (br, 1H).

LCMS Rt=1.72 minutes MS m/z=402 [M−H]−

The following examples were prepared according to Method A as described for Example 7 above, using the corresponding carboxylic acid precursor.

| Ex | Name | Data |
|---|---|---|
| 13 | 2,5-Difluoro-4-((3-methoxyphenoxy)methyl)-N-(methylsulfonyl)benzamide | LCMS Rt = 3.08 min. MS m/z 372[MH]+ |
| 14 | 2,5-Difluoro-4-((2-methoxyphenoxy)methyl)-N-(methylsulfonyl)benzamide | LCMS Rt = 2.97 min. MS m/z 372 [MH]+ |
| 15 | 4-((4-Chloro-2-methoxyphenoxy)methyl)-2,5-difluoro-N-(methylsulfonyl)benzamide Diethylamine salt | LCMS Rt = 3.24 min. MS m/z 404 [M − H]− |
| 16 | 4-((3-Chlorophenoxy)methyl)-N-(methylsulfonyl)benzamide Diethylamine salt | LCMS Rt = 2.74 min. MS m/z 338 [M − H]− |
| 17 | 4-((4-Cyanophenoxy)methyl)-N-(methylsulfonyl)benzamide | LCMS Rt = 3.20 min. MS m/z 331 [M + H]+ |
| 18 | 4-((4-Chlorophenoxy)methyl)-N-(methylsulfonyl)benzamide Diethylamine salt | LCMS Rt = 2.76 min. MS m/z 338 [M − H]− |
| 19 | 4-((3,4-Dichlorophenoxy)methyl)-3-methoxy-N-(methylsulfonyl)benzamide | LCMS Rt = 3.27 min. MS m/z 403 [M − H]− |

| Ex | Name | Data |
|----|------|------|
| 20 | 4-(Benzyloxy)-N-(methylsulfonyl)benzamide Diethylamine salt | LCMS Rt = 2.85 min. MS m/z 306 [M + H]+ |
| 21 | 4-(3-Bromobenzyloxy)-N-(methylsulfonyl)benzamide | LCMS Rt = 2.16 min. MS m/z 381 [M − H]− |
| 22 | 4-(4-(2-methyl-1H-imidazol-1-yl)benzyloxy)-N-(methylsulfonyl)benzamide | LCMS Rt = 1.91 min. MS m/z 384 [M − H]− |

The following examples were prepared according to Method B as described for Example 3 above, using the corresponding carboxylic acid precursor.

| Ex | Name | Data |
|----|------|------|
| 23 | N-(sec-Butylsulfonyl)-4-((3,4-dichlorophenoxy)methyl)-2,5-difluorobenzamide | $^1$H NMR (400 MHz, d$_6$-DMSO): δ 1.1 (m, 3H), 1.4 (m, 3H), 1.6 (m, 1 H), 2.1 (m, 1H), 3.4 (m, 1H), 5.3 (m, 2H), 7.1 (m, 1H), 7.3 (m, 1H), 7.5 (m, 1H), 7.6 (m, 1H). LCMS Rt = 4.10 min. MS m/z 450 [MH]− |
| 24 | 4-((2,4-Dichlorophenoxy)methyl)-N-(methylsulfonyl)benzamide Diethylamine salt | LCMS Rt = 2.25 min. MS m/z 372 [M − H]− |
| 25 | 4-((4-Ethylphenoxy)methyl)-N-(methylsulfonyl)benzamide Diethylamine salt | LCMS Rt = 3.75 min. MS m/z 332 [M − H]− |
| 26 | N-(methylsulfonyl)-4-{[2-pyridazin-4-yl-4-(trifluoromethyl)phenoxy]methyl}benzamide | $^1$H NMR (400 MHz, d$_6$-DMSO): δ 3.35 (s, 3H), 5.37 (s, 2H), 7.45 (d, 1H), 7.52 (d, 2H), 7.84-7.90 (m, 2H), 7.90-7.95 (m, 3H), 9.28 (dd, 1H), 9.49 (dd, 1H), 12.13 (br. s, 1H). LCMS Rt = 1.29 min. MS m/z 452 [MH]+, 450 [M − H]− |
| 27 | 4-{[4-Chloro-3-(trifluoromethyl)phenoxy]methyl}-N-(methylsulfonyl)benzamide | $^1$H NMR (400 MHz, CDCl$_3$): δ 2.95 (s, 3H), 5.10 (s, 2H), 7.00 (dd, 1H), 7.23 (d, 1H), 7.36 (d, 1H), 7.49 (d, 2H), 7.89 (d, 2H). LCMS Rt = 1.74 min. MS m/z 406 [M − H]− |
| 28 | 4-[(3,4-Dichlorophenoxy)methyl]-N-(methylsulfonyl)benzamide | $^1$HNMR (400 MHz, d$_6$-DMSO): δ 3.37 (s, 3H), 5.25 (s, 2H), 7.06 (dd, 1H), 7.35 (d, 1H), 7.52-7.61 (m, 3H), 7.93-8.00 (m, 2H), 12.14 (br, 1H). LCMS Rt = 3.31 min. MS m/z 374 [MH]+ |
| 29 | 3-Chloro-4-((3,4-dichlorophenoxy)methyl)-N-(methylsulfonyl)benzamide Diethylamine salt | LCMS Rt = 2.51 min. MS m/z 408 [MH]+ |
| 30 | 4-[(3,4-Dichlorophenoxy)methyl]-2-methoxy-N-(methylsulfonyl)benzamide | $^1$H NMR (400 MHz, CDCl$_3$): δ 3.41 (s, 3H), 4.05 (s, 3H), 5.09 (s, 2H), 6.82 (dd, 1H), 7.06-7.11 (m, 2H), 7.14 (d, 1 H), 7.35 (d, 1 H), 8.21 (d, 1H), 10.15 (br, NH). LCMS Rt = 1.75 min. MS m/z 404 [MH]+, 402 [M − H]− |

The following examples were prepared according to Method C as described for Example 8 above, using the corresponding phenol and benzyl bromide precursors.

| Ex | Name | Data |
|----|------|------|
| 31 | 4-[(4-Methoxyphenoxy)methyl]-N-(methylsulfonyl)benzamide | LCMS Rt = 3.27 min. MS m/z 334[M − H]−, 336[MH]+ |
| 32 | N-(Methylsulfonyl)-4-[(2-piperidin-4-ylphenoxy)methyl]benzamide | LCMS Rt = 2.25 min. MS m/z 389[MH]+, 387[M − H]− |
| 33 | 4-[(2,3-dichlorophenoxy)methyl]-N-(methylsulfonyl)benzamide | LCMS Rt = 1.78 min. MS m/z 374[MH]+, 372[M − H]− |
| 34 | 4-[(2-Methoxyphenoxy)methyl]-N-(methylsulfonyl)benzamide | LCMS Rt = 1.93 min. MS m/z 337[MH]+, 335[M − H]− |
| 35 | N-(Methylsulfonyl)-4-[(3-piperidin-4-ylphenoxy)methyl]benzamide | LCMS Rt = 2.39 min. MS m/z 389[MH]+, 387[M − H]− |
| 36 | N-(methylsulfonyl)-4-[(4-piperidin-4-ylphenoxy)methyl]benzamide diethylamine salt | LCMS Rt = 2.14 min. MS m/z 389[MH]+, 387[M − H]− |
| 37 | 4-{[4-(1-Methyl-1H-pyrazol-5-yl)phenoxy]methyl}-N-(methylsulfonyl)benzamide diethylamine salt | LCMS Rt = 2.67 min. MS m/z 386[MH]+, 384[M − H]− |

-continued

| Ex | Name | Data |
|---|---|---|
| 38 | 4-{[4-Chloro-2-(1-methyl-1H-pyrazol-5-yl)phenoxy]methyl}-N-(methylsulfonyl)benzamide diethylamine salt | LCMS Rt = 2.30 min. MS m/z 420[MH]+, 418[M − H]− |
| 39 | 3-Chloro-4-[(4-ethylphenoxy)methyl]-N-(methylsulfonyl)benzamide diethylamine salt | LCMS Rt = 3.96 min. MS m/z 368[MH]+, 366[M − H]− |
| 40 | 4-[(4-Ethylphenoxy)methyl]-2-fluoro-N-(methylsulfonyl)benzamide diethylamine salt | LCMS Rt = 3.60 min. MS m/z 352[MH]+, 350[M − H]− |
| 41 | 4-[(4-Ethylphenoxy)methyl]-2-methoxy-N-(methylsulfonyl)benzamide diethylamine salt | LCMS Rt = 3.72 min. MS m/z 365[MH]+, 363[M − H]− |
| 42 | 4-[(4-Ethylphenoxy)methyl]-3-methoxy-N-(methylsulfonyl)benzamide diethylamine salt | LCMS Rt = 2.30 min. MS m/z 365[MH]+, 363[M − H]− |
| 43 | 4-[(4-Ethylphenoxy)methyl]-2-methyl-N-(methylsulfonyl)benzamide diethylamine salt | LCMS Rt = 3.69 min. MS m/z 348[MH]+, 346[M − H]− |

The following examples were prepared according to Method D, as described for Example 2 above, using the corresponding phenol and benzyl bromide precursors.

| Ex | Name | Data |
|---|---|---|
| 44 | 4-[(2-Chloro-4-cyanophenoxy)methyl]-2,5-difluoro-N-(methylsulfonyl)benzamide | $^1$H NMR (400 MHz, d$_6$-DMSO): δ 3.38 (s, 3H), 5.40 (s, 2H), 7.44 (m, 1H), 7.56 (m, 1H), 7.62 (m, 1 H), 7.83 (m, 1H), 8.07 (s, 1H). LCMS Rt = 1.62 min. MS m/z 399 [M − H]− |
| 45 | 4-[(3-Chloro-4-cyanophenoxy)methyl]-2,5-difluoro-N-(methylsulfonyl)benzamide | $^1$H NMR (400 MHz, d$_6$-DMSO): δ 3.39 (s, 3H), 5.36 (s, 2H), 7.22 (m, 1H), 7.54 (s, 1H), 7.60 (m, 2H), 7.92 (m, 1H). LCMS Rt = 1.63 min. MS m/z 399 [M − H]− |
| 46 | 4-[(3-Chloro-4-fluorophenoxy)methyl]-2,5-difluoro-N-(methylsulfonyl)benzamide | $^1$H NMR (400 MHz, d$_6$-DMSO): δ 3.39 (s, 3H), 5.20 (s, 2H), 7.04 (m, 1H), 7.37 (m, 2H), 7.59 (m, 2H). LCMS Rt = 1.75 min. MS m/z 392 [M − H]− |
| 47 | 4-[(4-Chloro-3-cyanophenoxy)methyl]-2,5-difluoro-N-(methylsulfonyl)benzamide | $^1$H NMR (400 MHz, d$_6$-DMSO): δ 3.36 (s, 3H), 5.24 (s, 2H), 7.41 (m, 1H), 7.60 (m, 2H), 7.64 (m, 1H), 7.77 (m, 1H). LCMS Rt = 1.71 min. MS m/z 399 [M − H]− |
| 48 | 4-[(3,4-Difluorophenoxy)methyl]-2,5-difluoro-N-(methylsulfonyl)benzamide | $^1$H NMR (400 MHz, d$_6$-DMSO): δ 3.37 (s, 3H), 5.18 (s, 2H), 6.90 (s, 1H), 7.22 (m, 1H0, 7.37 (m, 1H), 7.58 (m, 2H). LCMS Rt = 1.67 min. MS m/z 376 [M − H]− |
| 49 | 4-[(4-Chloro-3-fluorophenoxy)methyl]-2,5-difluoro-N-(methylsulfonyl)benzamide | $^1$H NMR (400 MHz, d$_6$-DMSO): δ 3.38 (s, CH3), 5.20 (s, 2H), 6.96 (m, 1H), 7.21 (m, 1H), 7.50 (m, 1H), 7.59 (m, 2H). LCMS Rt = 1.77 min. MS m/z 392 [MH]− |
| 50 | 4-{[4-chloro-3-(difluoromethoxy)phenoxy]methyl}-2,5-difluoro-N-(methylsulfonyl)benzamide | $^1$H NMR (400 MHz, d$_6$-DMSO): δ 3.40 (s, 3H), 5.20 (s, 2H), 7.00 (m, 1H), 7.10 (m, 1H), 7.30 (t, 1H), 7.55 (m, 1H), 7.60 (m, 2H). LCMS Rt = 1.45 min. MS m/z 440 [MH]− |
| 51 | 4-((4-Chloro-3-(trifluoromethoxy)phenoxy)methyl)-2,5-difluoro-N-(methylsulfonyl)benzamide | $^1$H NMR (400 MHz, CDCl$_3$): δ 3.44 (s, 3H), 5.16 (s, 2H), 6.88 (m, 1H), 6.98 (m, 1H), 7.41 (m, 1H), 7.43 (m, 1H), 7.85 (m, 1H), 8.81 (s, 1H). LCMS Rt = 3.58 min. MS m/z 458 [MH]− |
| 52 | 4-{[3-Chloro-4-(difluoromethoxy)phenoxy]methyl}-2,5-difluoro-N-(methylsulfonyl)benzamide | $^1$H NMR (400 MHz, d$_6$-DMSO): δ 3.40 (s, 3H), 5.20 (s, 2H), 7.15 (t, 1H), 7.10 (m, 1H), 7.35 (m, 2H), 7.60 (m, 2H). LCMS Rt = 1.44 min. MS m/z 440 [MH]− |
| 53 | 4-((3-Chloro-4-(trifluoromethoxy)phenoxy)methyl)-2,5-difluoro-N-(methylsulfonyl)benzamide | $^1$H NMR (400 MHz, CD$_3$OD): δ 3.15 (s, 3H), 5.18 (s, 2H), 7.05 (m, 1H), 7.20-7.35 (m, 2H), 7.40 (m, 1H), 7.55 (m, 1H). LCMS Rt = 3.62 min. MS m/z 458 [MH]− |
| 54 | 4-((4-Chloro-3-(trifluoromethyl)phenoxy)methyl)-2,5-difluoro-N-(methylsulfonyl)benzamide | $^1$H NMR (400 MHz, d$_6$-DMSO): δ 3.30 (s, 3H), 5.25 (s, 2H), 7.38 (m, 1H), 7.49 (m, 1H), 7.60 (m, 3H). LCMS Rt = 4.43 min. MS m/z 442 [MH]− |
| 55 | 4-[(2,5-Difluorophenoxy)methyl]-2,5-difluoro-N-(methylsulfonyl)benzamide | $^1$H NMR (400 MHz, d$_6$-DMSO): δ 3.36 (s, 3H), 5.27 (s, 2H), 6.78-6.85 (m, 1H), 7.24-7.32 (m, 2H), 7.52-7.57 (m, 1 H), 7.62 (dd, 1H). LCMS Rt = 2.87 min. MS m/z 376 [M − H]− |
| 56 | 4-[(3-Trifluoromethoxy)methyl]-2,5-difluoro-N-(methylsulfonyl)benzamide | $^1$H NMR (400 MHz, d$_6$-DMSO): δ 3.35 (s, 3H), 5.23 (s, 2H), 6.94-7.00 (m, 1 H), 7.07-7.12 (m, 2H), 7.43 (t, 1H), 7.55-7.63 (m, 2H). LCMS Rt = 1.63 min. MS m/z 424 [M − H]− |

-continued

| Ex | Name | Data |
|---|---|---|
| 57 | 2,5-Difluoro-N-(methylsulfonyl)-4-[(2,4,5-trifluorophenoxy)methyl]benzamide | $^1$H NMR (400 MHz, d$_6$-DMSO): δ 3.35 (s, 3H), 5.25 (d, 2H), 7.51-7.57 (m, 1H), 7.57-7.67 (m, 3H). LCMS Rt = 1.60 min. MS m/z 396 [MH]+, 394 [M − H]− |
| 58 | 5-Chloro-4-(3-chloro-4-(trifluoromethyl)benzyloxy)-2-fluoro-N-(methylsulfonyl)benzamide | $^1$H NMR (400 MHz, d$_6$-DMSO): δ 3.38 (s, 3H), 5.35 (s, 2H), 7.22 (m, 1H), 7.50 (m, 1H), 7.65 (m, 1H), 7.81 (m, 1H), 7.85 (m, 1H), 12.40 (br, 1H). LCMS Rt = 3.49 min. MS m/z 458[M − H]− |
| 59 | 5-Chloro-4-(4-chloro-3-(trifluoromethyl)benzyloxy)-2-fluoro-N-(methylsulfonyl)benzamide | $^1$H NMR (400 MHz, d$_6$-DMSO): δ 3.37 (s, 3H), 5.29 (s, 2H), 7.40 (m, 1H), 7.57 (m, 1H), 7.67 (m, 2H), 7.82 (m, 1H), 12.40 (br, 1H). LCMS Rt = 3.49 min. MS m/z 458[M − H]−, |
| 60 | 5-Chloro-4-((3-chloro-4-(trifluoromethoxy)phenyl)methyl)-2-fluoro-N-(methylsulfonyl)benzamide | $^1$H NMR (400 MHz, CDCl$_3$): δ 3.09 (s, 3H), 4.82 s, 2H), 6.72 (d, 1H), 6.93 (s, 1H), 7.01-7.17 (m, 2H), 7.81 (s, 1H). LCMS Rt = 3.49 min. MS m/z 476[MH]+, |
| 61 | 5-Chloro-4-{[3-chloro-4-(difluoromethoxy)phenoxy]methyl}-2-fluoro-N-(methylsulfonyl)benzamide | $^1$H NMR(400 MHz, d$_6$-DMSO): δ 3.40 (s, 3H), 5.20 (s, 2H), 7.15 (t, 1H), 7.10 (m, 1H), 7.35 (m, 2H), 7.60 (m, 1H), 7.85 (m, 1H). LCMS Rt = 1.42 min. MS m/z 456 [M − H]− |
| 62 | 5-Chloro-4-{[4-chloro-3-(difluoromethoxy)phenoxy]methyl}-2-fluoro-N-(methylsulfonyl)benzamide | $^1$H NMR (400 MHz, d$_6$-DMSO): δ 3.40 (s, 3H), 5.20 (s, 2H), 7.00 (m, 1H), 7.15 (m, 1H), 7.30 (t, 1H), 7.55 (m, 1H), 7.60 (m, 1H), 7.85 (m, 1H). LCMS Rt = 1.48 min. MS m/z 456 M[−H]− |
| 63 | 5-Chloro-4-{[4-chloro-3-(trifluoromethoxy)phenoxy]methyl}-2-fluoro-N-(methylsulfonyl)benzamide | $^1$H NMR (400 MHz, d$_6$-DMSO): δ 3.40 (s, 3H), 5.25 (s, 2H), 7.20 (m, 1H), 7.35 (m, 1H), 7.65 (m, 2H), 7.85 (m, 1H). LCMS Rt = 3.76 min. MS m/z 474 [MH]− |
| 64 | 4-[(4-Chloro-2-methoxyphenoxy)methyl]-N-(methylsulfonyl)benzamide | $^1$H NMR (400 MHz, CDCl$_3$): δ 3.42 (s, 3H), 3.88 (s, 3H), 5.20 (s, 2H), 6.78 (d, 1H), 6.82 (m, 1H), 6.85 (s, 1H), 7.56 (m, 2H), 7.81 (m, 2H), 8.50 (br, 1H). LCMS Rt = 1.54 min. MS m/z 369 [MH]−, 371 [MH]− |
| 65 | 4-{[3-Chloro-4-(trifluoromethyl)phenoxy]methyl}-N-(methylsulfonyl)benzamide | $^1$H NMR (400 MHz, CD$_3$OD): δ 3.34 (s, 3H), 5.27 (s, 2H), 7.09 (dd, 1H), 7.26 (d, 1H), 7.60 (d, 2H), 7.68 (d, 1H), 7.94 (d, 2H) LCMS Rt = 2.95 min. MS m/z 406 [MH]− |

The following examples were prepared according to Method E, as described for Example 9 above, from the corresponding phenol and benzyl bromide.

| Ex | Name | Data |
|---|---|---|
| 66 | 4-(4-Chloro-3-methoxybenzyloxy)-2,5-difluoro-N-(methylsulfonyl)benzamide | LCMS Rt = 2.82 min. MS m/z 404 [MH]− |
| 67 | 4-(4-Chloro-3-cyanobenzyloxy)-2,5-difluoro-N-(methylsulfonyl)benzamide Diethylamine salt | LCMS Rt = 2.64 min. m/z 399 [MH]− |
| 68 | 4-(3-Chloro-4-methoxybenzyloxy)-2,5-difluoro-N-(methylsulfonyl)benzamide | LCMS Rt = 2.70 min. MS m/z 404 [MH]− |

The following example was prepared according to Method F, as described for Example 1 above, using 5-bromo-2-[(3,4-dichlorophenoxy)methyl]benzonitrile (Preparation 60).

| Ex | Name | Data |
|---|---|---|
| 69 | 5-Cyano-4-((3,4-dichlorophenoxy)methyl)-N-(methylsulfonyl)benzamide Diethylamine salt | LCMS Rt = 3.82 min. MS m/z 397 [MH]− |

The following example was prepared according to Method G, as described for Example 11 above, using 2,5-difluoro-4-[4-chloro-3-(trifluoromethyl)phenylmethoxy]-benzamide (Preparation 62).

| Ex | Name | Data |
|---|---|---|
| 70 | 4-(4-Chloro-3-(trifluoromethyl)benzyloxy)-2,5-difluoro-N-(methylsulfonyl) benzamide | $^1$H NMR (400 MHz, CD$_3$OD): δ 3.15 (3H, s), 5.05 (2H, s), 6.95 (1H, dd), 7.35 (1H, dd), 7.42(1H, m), 7.48 (1H, m), 7.74 (1H, brs). LCMS Rt = 3.66 min. MS m/z 444[MH]+, 442[MH]− |

The following Examples were prepared according to the process described in Example 5 above, using the corresponding methanol and benzoate precursors. All mass spectra, MS (m/z), are [MH]+ unless otherwise stated.

| Ex | NAME | MS (m/z) |
|---|---|---|
| 71 | 5-chloro-2-fluoro-4-[(4-methoxybenzyl)oxy]-N-(methylsulfonyl)benzamide | 388 |
| 72 | 5-chloro-2-fluoro-N-(methylsulfonyl)-4-{[4-(trifluoromethoxy)benzyl]oxy}benzamide | 442 |
| 73 | 3-chloro-4-[(4-chlorobenzyl)oxy]-N-(methylsulfonyl)benzamide | 374 |
| 74 | 4-[(3-chlorobenzyl)oxy]-3-cyano-N-(methylsulfonyl)benzamide | 365 |
| 75 | 3-chloro-N-(methylsulfonyl)-4-{[2-(trifluoromethyl)benzyl]oxy}benzamide | 408 |
| 76 | 3-cyano-N-(methylsulfonyl)-4-{[2-(trifluoromethoxy)benzyl]oxy}benzamide | 415 |
| 77 | 4-[(4-chlorobenzyl)oxy]-3-cyano-N-(methylsulfonyl)benzamide | 365 |
| 78 | 5-chloro-4-[(2-chlorobenzyl)oxy]-2-fluoro-N-(methylsulfonyl)benzamide | 392 |
|  | No Example 79 |  |
| 80 | 3-chloro-4-[(3-cyanobenzyl)oxy]-N-(methylsulfonyl)benzamide | 365 |
|  | No Example 81 |  |
| 82 | 4-[(3-methoxybenzyl)oxy]-N-(methylsulfonyl)benzamide | 336 |
| 83 | 4-(biphenyl-4-ylmethoxy)-5-chloro-2-fluoro-N-(methylsulfonyl)benzamide | 434 |
| 84 | 5-chloro-4-[(4-chlorobenzyl)oxy]-2-fluoro-N-(methylsulfonyl)benzamide | 392 |
| 85 | 4-(biphenyl-4-ylmethoxy)-N-(methylsulfonyl)benzamide | 382 |
| 86 | 5-chloro-4-[(3-chlorobenzyl)oxy]-2-fluoro-N-(methylsulfonyl)benzamide | 392 |
| 87 | 4-(biphenyl-2-ylmethoxy)-5-chloro-2-fluoro-N-(methylsulfonyl)benzamide | 434 |
| 88 | 4-[(4-chlorobenzyl)oxy]-N-(methylsulfonyl)benzamide | 340 |
| 89 | 4-[(4-methoxybenzyl)oxy]-N-(methylsulfonyl)benzamide | 336 |
| 90 | 3-chloro-N-(methylsulfonyl)-4-{[4-(1H-pyrazol-1-yl)benzyl]oxy}benzamide | 406 |
| 91 | 4-[(3-chlorobenzyl)oxy]-N-(methylsulfonyl)benzamide | 340 |
| 92 | N-(methylsulfonyl)-4-{[3-(trifluoromethoxy)benzyl]oxy}benzamide | 390 |
| 93 | 4-(biphenyl-2-ylmethoxy)-3-cyano-N-(methylsulfonyl)benzamide | 407 |
| 94 | 4-(biphenyl-2-ylmethoxy)-N-(methylsulfonyl)benzamide | 382 |

The following Examples were prepared according to Method D, as described for Example 2 above, using the corresponding phenol and benzyl bromide precursors. All mass spectra, MS (m/z), are [MH]− unless otherwise stated.

| Ex | NAME | MS (m/z) |
|---|---|---|
|  | No Example 95 |  |
|  | No Example 96 |  |
| 97 | 2,5-difluoro-4-[(3-fluoro-4-methoxyphenoxy)methyl]-N-(methylsulfonyl)benzamide | 388 |
| 98 | 4-[(3-chloro-5-methoxyphenoxy)methyl]-2,5-difluoro-N-(methylsulfonyl)benzamide | 404 |
| 99 | 4-{[(6-cyano-2-naphthyl)oxy]methyl}-2,5-difluoro-N-(methylsulfonyl)benzamide | 415 |
| 100 | 4-[(5-chloro-2-methylphenoxy)methyl]-2,5-difluoro-N-(methylsulfonyl)benzamide | 388 |
| 101 | 4-{[4-cyano-3-(trifluoromethyl)phenoxy]methyl}-2,5-difluoro-N-(methylsulfonyl)benzamide | 433 |
| 102 | 2,5-difluoro-4-{[2-methyl-3-(1H-pyrazol-1-yl)phenoxy]methyl}-N-(methylsulfonyl)benzamide | 420 |
| 103 | 4-[(3,4-dicyanophenoxy)methyl]-2,5-difluoro-N-(methylsulfonyl)benzamide | 390 |
| 104 | 4-[(4-cyano-2-fluorophenoxy)methyl]-2,5-difluoro-N-(methylsulfonyl)benzamide | 383 |
| 105 | 4-[(3-chloro-5-methylphenoxy)methyl]-2,5-difluoro-N-(methylsulfonyl)benzamide | 388 |
| 106 | 2,5-difluoro-4-{[3-(1-methylpiperidin-4-yl)phenoxy]methyl}-N-(methylsulfonyl)benzamide | 439 [MH]+ |
| 107 | 2,5-difluoro-4-[(3-isopropylphenoxy)methyl]-N-(methylsulfonyl)benzamide | 382 |
| 108 | 2,5-difluoro-4-{[3-fluoro-5-(trifluoromethyl)phenoxy]methyl}-N-(methylsulfonyl)benzamide | 426 |
| 109 | 2,5-difluoro-N-(methylsulfonyl)-4-{[3-(trifluoromethyl)phenoxy]methyl}benzamide | 408 |

| Ex | NAME | MS (m/z) |
|---|---|---|
| 110 | 2,5-difluoro-4-[(2-fluorophenoxy)methyl]-N-(methylsulfonyl)benzamide | 358 |
| 111 | 4-[(2,3-difluorophenoxy)methyl]-2,5-difluoro-N-(methylsulfonyl)benzamide | 376 |
| 112 | 4-[(2-ethylphenoxy)methyl]-2,5-difluoro-N-(methylsulfonyl)benzamide | 368 |
| 113 | 2,5-difluoro-4-{[3-(4-methylpiperazin-1-yl)phenoxy]methyl}-N-(methylsulfonyl)benzamide | 438 |
| | No Example 114 | |
| 115 | 2,5-difluoro-4-[(4-methylphenoxy)methyl]-N-(methylsulfonyl)benzamide | 354 |
| 116 | 2,5-difluoro-4-[(3-fluorophenoxy)methyl]-N-(methylsulfonyl)benzamide | 358 |
| 117 | 2,5-difluoro-N-(methylsulfonyl)-4-{[2-(trifluoromethoxy)phenoxy]methyl}benzamide | 424 |
| 118 | 4-[(3,5-difluorophenoxy)methyl]-2,5-difluoro-N-(methylsulfonyl)benzamide | 376 |
| 119 | 4-[(3,5-dimethylphenoxy)methyl]-2,5-difluoro-N-(methylsulfonyl)benzamide | 368 |
| 120 | 4-[(3,4-dimethylphenoxy)methyl]-2,5-difluoro-N-(methylsulfonyl)benzamide | 368 |
| 121 | 4-[(3-chloro-4-ethoxyphenoxy)methyl]-2,5-difluoro-N-(methylsulfonyl)benzamide | 418 |
| 122 | 4-[(2-chloro-5-methoxyphenoxy)methyl]-2,5-difluoro-N-(methylsulfonyl)benzamide | 406 [MH]+ |
| 123 | 2,5-difluoro-4-{[2-fluoro-5-(trifluoromethyl)phenoxy]methyl}-N-(methylsulfonyl)benzamide | 426 |
| 124 | 4-[(3-chloro-5-fluorophenoxy)methyl]-2,5-difluoro-N-(methylsulfonyl)benzamide | 392 |
| 125 | 4-[(3-cyano-4-fluorophenoxy)methyl]-2,5-difluoro-N-(methylsulfonyl)benzamide | 383 |
| 126 | 4-[(2,6-difluorophenoxy)methyl]-2,5-difluoro-N-(methylsulfonyl)benzamide | 378 |
| 127 | 4-[(4-cyano-3-fluorophenoxy)methyl]-2,5-difluoro-N-(methylsulfonyl)benzamide | 383 |
| 128 | 2,5-difluoro-4-[(3-fluoro-5-methoxyphenoxy)methyl]-N-(methylsulfonyl)benzamide | 388 |
| 129 | 4-[(2-chloro-3,4-difluorophenoxy)methyl]-2,5-difluoro-N-(methylsulfonyl)benzamide | 410 |
| 130 | 2,5-difluoro-N-(methylsulfonyl)-4-[(2-naphthyloxy)methyl]benzamide | 390 |
| 131 | 4-[(2-chloro-5-cyano-4-methylphenoxy)methyl]-2,5-difluoro-N-(methylsulfonyl)benzamide | 413 |
| 132 | 4-[(4-cyano-2-methoxyphenoxy)methyl]-2,5-difluoro-N-(methylsulfonyl)benzamide | 395 |
| 133 | 4-[(4-chloro-2-fluorophenoxy)methyl]-2,5-difluoro-N-(methylsulfonyl)benzamide | 392 |
| 134 | 4-[(2,5-dichlorophenoxy)methyl]-2,5-difluoro-N-(methylsulfonyl)benzamide | 408 |
| 135 | 4-[(4-chloro-2-cyanophenoxy)methyl]-2,5-difluoro-N-(methylsulfonyl)benzamide | 399 |
| 136 | 2,5-difluoro-N-(methylsulfonyl)-4-[(3-morpholin-4-ylphenoxy)methyl]benzamide | 425 |
| 137 | 4-[(2-cyanophenoxy)methyl]-2,5-difluoro-N-(methylsulfonyl)benzamide | 365 |
| 138 | 2,5-difluoro-N-(methylsulfonyl)-4-{[4-(1,3-oxazol-4-yl)phenoxy]methyl}benzamide | 407 |
| 139 | 2,5-difluoro-4-{[3-methoxy-4-(1H-pyrazol-1-yl)phenoxy]methyl}-N-(methylsulfonyl)benzamide | 436 |
| 140 | 2,5-difluoro-N-(methylsulfonyl)-4-[(2,3,6-trifluorophenoxy)methyl]benzamide | 394 |
| 141 | 2,5-difluoro-N-(methylsulfonyl)-4-{[4-(trifluoromethyl)phenoxy]methyl}benzamide | 408 |
| 142 | 2,5-difluoro-4-{[4-fluoro-3-(trifluoromethyl)phenoxy]methyl}-N-(methylsulfonyl)benzamide | 426 |
| 143 | 2,5-difluoro-4-[(5-fluoro-2-isopropoxyphenoxy)methyl]-N-(methylsulfonyl)benzamide | 416 |
| 144 | 2,5-difluoro-N-(methylsulfonyl)-4-{[4-(trifluoromethoxy)phenoxy]methyl}benzamide | 424 |
| 145 | 4-[(2-cyclopropyl-4-fluorophenoxy)methyl]-2,5-difluoro-N-(methylsulfonyl)benzamide | 398 |
| 146 | 4-[(2-cyano-4-methoxyphenoxy)methyl]-2,5-difluoro-N-(methylsulfonyl)benzamide | 395 |
| 147 | 2,5-difluoro-4-[(4-isopropylphenoxy)methyl]-N-(methylsulfonyl)benzamide | 382 |
| 148 | 4-[(4-chloro-2-isoxazol-5-ylphenoxy)methyl]-2,5-difluoro-N-(methylsulfonyl)benzamide | 441 |

| Ex | NAME | MS (m/z) |
|---|---|---|
| 149 | 4-[(2-chloro-6-fluorophenoxy)methyl]-2,5-difluoro-N-(methylsulfonyl)benzamide | 394 [MH]+ |
| 150 | 2,5-difluoro-4-[(3-methoxy-5-methylphenoxy)methyl]-N-(methylsulfonyl)benzamide | 384 |
| 151 | 4-[(3-chloro-4-methylphenoxy)methyl]-2,5-difluoro-N-(methylsulfonyl)benzamide | 388 |
| 152 | 4-[(2-chloro-3-cyano-4-fluorophenoxy)methyl]-2,5-difluoro-N-(methylsulfonyl)benzamide | 417 |
| 153 | 4-[(2-cyano-4-fluorophenoxy)methyl]-2,5-difluoro-N-(methylsulfonyl)benzamide | 383 |
| 154 | 4-[(3-cyanophenoxy)methyl]-2,5-difluoro-N-(methylsulfonyl)benzamide | 365 |
| 155 | 4-[(2,3-difluoro-4-methoxyphenoxy)methyl]-2,5-difluoro-N-(methylsulfonyl)benzamide | 406 |
| 156 | 2,5-difluoro-4-{[(7-methoxy-1-naphthyl)oxy]methyl}-N-(methylsulfonyl)benzamide | 420 |
| 157 | 4-[(2-chloro-4-methoxyphenoxy)methyl]-2,5-difluoro-N-(methylsulfonyl)benzamide | 404 |
| 158 | 2,5-difluoro-4-[(4-fluorophenoxy)methyl]-N-(methylsulfonyl)benzamide | 358 |
| 159 | 4-[(4-chloro-3-methylphenoxy)methyl]-2,5-difluoro-N-(methylsulfonyl)benzamide | 388 |
| 160 | 2,5-difluoro-4-{[(4-methoxy-1-naphthyl)oxy]methyl}-N-(methylsulfonyl)benzamide | 420 |
| 161 | 4-[(3-ethoxyphenoxy)methyl]-2,5-difluoro-N-(methylsulfonyl)benzamide | 384 |
| 162 | 4-[(4-cyano-3,5-dimethylphenoxy)methyl]-2,5-difluoro-N-(methylsulfonyl)benzamide | 393 |
| 163 | 4-[(3-chloro-2-cyano-4-fluorophenoxy)methyl]-2,5-difluoro-N-(methylsulfonyl)benzamide | 417 |
| 164 | 2,5-difluoro-4-[(4-methoxyphenoxy)methyl]-N-(methylsulfonyl)benzamide | 370 |
| 165 | 2,5-difluoro-N-(methylsulfonyl)-4-[(1-naphthyloxy)methyl]benzamide | 390 |
| 166 | 2,5-difluoro-4-{[3-(5-methyl-1,2,4-oxadiazol-3-yl)phenoxy]methyl}-N-(methylsulfonyl)benzamide | 422 |
| 167 | 4-[(3,4-difluoro-2-methylphenoxy)methyl]-2,5-difluoro-N-(methylsulfonyl)benzamide | 390 |
| 168 | 2,5-difluoro-N-(methylsulfonyl)-4-[(3-piperidin-1-ylphenoxy)methyl]benzamide | 423 |

The Examples in the table that follows were prepared according to the following three step process.

Step 1:

The phenol template—either (a) methyl-4-hydroxy-benzoate or (b) methyl-2,5-difluoro-4-hydroxy-benzoate—(0.15 mmol) and appropriate alcohol monomer (0.13 mmol) were dissolved in $CH_2Cl_2$. Polymer-supported triphenylphosphine (125 mg, 3.0 mmol/g, 0.375 mmol) was added followed by N,N,N'N'-Tetramethylazodicarboxylate (43 mg, 0.25 mmol). The resulting mixture was stirred at 30° C. for 16 hours. The reaction mixture was filtered then citric acid (1.0 mL, 2.5% aqueous) added to the filtrate. The mixture was then extracted with $CH_2Cl_2$ (3×1.0 mL) and the combined organics concentrated under reduced pressure to yield the crude benzoate. The material was taken on to the next step without further purification.

Step 2:

Saponification was carried out according to Preparation 9 using the benzoate from Step 1 with lithium hydroxide (0.63 mL, 2M, 1.25 mmol), THF (0.63 mL) and shaken at 50° C. for 16 hours. The benzoic acid was taken on to the next step without further purification.

Step 3:

Acyl sulfonamide formation was carried out according to Example 3, Method B, using the benzoic acid from Step 2 with methylsulfonamide (12 mg, 0.13 mmol), EDCl (72 mg, 0.38 mmol) and DMAP (23 mg, 0.19 mmol). The reaction mixture was shaken at 30° C. for 16 hours.

All mass spectra, MS (m/z), are [MH]+ unless otherwise stated.

| Ex | NAME | MS (m/z) |
|---|---|---|
| 169 | 4-[(2-methoxybenzyl)oxy]-N-(methylsulfonyl)benzamide | 336 |
| 170 | 4-[(2,3-difluorobenzyl)oxy]-N-(methylsulfonyl)benzamide | 342 |
| 171 | 4-[(2-chloro-4-fluorobenzyl)oxy]-N-(methylsulfonyl)benzamide | 358 |
| 172 | 4-[(4-cyanobenzyl)oxy]-N-(methylsulfonyl)benzamide | 331 |
| 173 | 4-[(3,5-dichlorobenzyl)oxy]-N-(methylsulfonyl)benzamide | 374 |
| 174 | 4-(cyclohexylmethoxy)-N-(methylsulfonyl)benzamide | 312 |
| 175 | 4-[(2,5-dichlorobenzyl)oxy]-N-(methylsulfonyl)benzamide | 374 |
| 176 | 4-[(4-fluorobenzyl)oxy]-N-(methylsulfonyl)benzamide | 324 |
| 177 | 4-[(3,4-difluorobenzyl)oxy]-N-(methylsulfonyl)benzamide | 342 |
| 178 | 4-[(4-chloro-3-fluorobenzyl)oxy]-N-(methylsulfonyl)benzamide | 358 |
| 179 | N-(methylsulfonyl)-4-{[3-(trifluoromethyl)benzyl]oxy}benzamide | 374 |

-continued

| Ex | NAME | MS (m/z) |
|---|---|---|
| 180 | 4-[(2-fluorobenzyl)oxy]-N-(methylsulfonyl)benzamide | 324 |
| 181 | N-(methylsulfonyl)-4-{[4-(trifluoromethoxy)benzyl]oxy}benzamide | 390 |
| 182 | 4-[(2-chloro-6-fluorobenzyl)oxy]-N-(methylsulfonyl)benzamide | 358 |
| 183 | N-(methylsulfonyl)-4-{[2-(trifluoromethyl)benzyl]oxy}benzamide | 374 |
| 184 | 4-[(2,6-dichlorobenzyl)oxy]-N-(methylsulfonyl)benzamide | 374 |
| 185 | 4-[(4-fluoro-3-methoxybenzyl)oxy]-N-(methylsulfonyl)benzamide | 354 |
| 186 | 4-[(2-chlorobenzyl)oxy]-N-(methylsulfonyl)benzamide | 340 |
| 187 | 4-[(3,5-difluorobenzyl)oxy]-N-(methylsulfonyl)benzamide | 342 |
| 188 | 4-[(2-fluoro-5-methoxybenzyl)oxy]-N-(methylsulfonyl)benzamide | 354 |
| 189 | 4-[(2,3-dichlorobenzyl)oxy]-N-(methylsulfonyl)benzamide | 374 |
| 190 | 4-[(2,4-dichlorobenzyl)oxy]-N-(methylsulfonyl)benzamide | 374 |
| 191 | 4-(cyclopentylmethoxy)-N-(methylsulfonyl)benzamide | 298 |
| 192 | 2,5-difluoro-N-(methylsulfonyl)-4-{[3-(trifluoromethyl)benzyl]oxy}benzamide | 410 |
| 193 | 2,5-difluoro-N-(methylsulfonyl)-4-{[4-(trifluoromethyl)benzyl]oxy}benzamide | 410 |
| 194 | 2,5-difluoro-N-(methylsulfonyl)-4-(1-naphthylmethoxy)benzamide | 392 |
| 195 | 2,5-difluoro-4-[(3-fluorobenzyl)oxy]-N-(methylsulfonyl)benzamide | 360 |
| 196 | 2,5-difluoro-4-[(4-methylbenzyl)oxy]-N-(methylsulfonyl)benzamide | 356 |
| 197 | 4-(cyclobutylmethoxy)-2,5-difluoro-N-(methylsulfonyl)benzamide | 320 |
| 198 | 2,5-difluoro-4-[(4-methoxybenzyl)oxy]-N-(methylsulfonyl)benzamide | 372 |
| 199 | 2,5-difluoro-4-[(2-fluorobenzyl)oxy]-N-(methylsulfonyl)benzamide | 360 |
| 200 | 2,5-difluoro-4-[(2-methoxy-4-methylbenzyl)oxy]-N-(methylsulfonyl)benzamide | 386 |
| 201 | 4-[(3,5-dimethoxybenzyl)oxy]-2,5-difluoro-N-(methylsulfonyl)benzamide | 402 |
| 202 | 4-[(2,5-dimethoxybenzyl)oxy]-2,5-difluoro-N-(methylsulfonyl)benzamide | 402 |
| 203 | 4-[(3,4-dimethylbenzyl)oxy]-2,5-difluoro-N-(methylsulfonyl)benzamide | 370 |
| 204 | 4-[(2,4-difluorobenzyl)oxy]-N-(methylsulfonyl)benzamide | 342 |
| 205 | 2,5-difluoro-4-[(2-fluoro-5-methoxybenzyl)oxy]-N-(methylsulfonyl)benzamide | 390 |
| 206 | 4-[(2,3-dimethoxybenzyl)oxy]-2,5-difluoro-N-(methylsulfonyl)benzamide | 402 |
| 207 | 4-[(3-chlorobenzyl)oxy]-2,5-difluoro-N-(methylsulfonyl)benzamide | 376 |
| 208 | 4-[(2,5-difluorobenzyl)oxy]-N-(methylsulfonyl)benzamide | 342 |
| 209 | 2,5-difluoro-4-[(2-methylbenzyl)oxy]-N-(methylsulfonyl)benzamide | 356 |
| 210 | 4-[(2-methoxy-5-methylbenzyl)oxy]-N-(methylsulfonyl)benzamide | 350 |
| 211 | 4-{[4-(difluoromethoxy)benzyl]oxy}-2,5-difluoro-N-(methylsulfonyl)benzamide | 408 |
| 212 | 2,5-difluoro-N-(methylsulfonyl)-4-{[4-(trifluoromethoxy)benzyl]oxy}benzamide | 426 |
| 213 | 4-[(4-chloro-2-fluorobenzyl)oxy]-N-(methylsulfonyl)benzamide | 358 |
| 214 | 4-[(2,3-dichlorobenzyl)oxy]-2,5-difluoro-N-(methylsulfonyl)benzamide | 410 |
| 215 | 2,5-difluoro-4-[(4-fluoro-2-methoxybenzyl)oxy]-N-(methylsulfonyl)benzamide | 390 |
| 216 | 2,5-difluoro-4-[(4-fluorobenzyl)oxy]-N-(methylsulfonyl)benzamide | 360 |
| 217 | 2,5-difluoro-4-[(3-methylbenzyl)oxy]-N-(methylsulfonyl)benzamide | 356 |
| 218 | 4-{[2-(difluoromethoxy)benzyl]oxy}-2,5-difluoro-N-(methylsulfonyl)benzamide | 408 |
| 219 | 2,5-difluoro-4-[(2-methoxy-5-methylbenzyl)oxy]-N-(methylsulfonyl)benzamide | 386 |
| 220 | 2,5-difluoro-N-(methylsulfonyl)-4-{[2-(trifluoromethyl)benzyl]oxy}benzamide | 410 |
| 221 | 4-[(2-chlorobenzyl)oxy]-2,5-difluoro-N-(methylsulfonyl)benzamide | 376 |
| 222 | 2,5-difluoro-4-[(3-methoxy-4-methylbenzyl)oxy]-N-(methylsulfonyl)benzamide | 386 |
| 223 | 4-[(5-chloro-2-methoxybenzyl)oxy]-N-(methylsulfonyl)benzamide | 370 |
| 224 | 4-{[3-(difluoromethoxy)benzyl]oxy}-2,5-difluoro-N-(methylsulfonyl)benzamide | 408 |
| 225 | 4-[(4-chlorobenzyl)oxy]-2,5-difluoro-N-(methylsulfonyl)benzamide | 376 |
| 226 | 4-[(2-ethoxybenzyl)oxy]-2,5-difluoro-N-(methylsulfonyl)benzamide | 386 |
| 227 | 2,5-difluoro-N-(methylsulfonyl)-4-(2-naphthylmethoxy)benzamide | 392 |
| 228 | 4-[(3-chloro-4-methylbenzyl)oxy]-2,5-difluoro-N-(methylsulfonyl)benzamide | 390 |
| 229 | 4-[(2,5-difluorobenzyl)oxy]-2,5-difluoro-N-(methylsulfonyl)benzamide | 378 |
| 230 | 4-[(5-chloro-2-methoxybenzyl)oxy]-2,5-difluoro-N-(methylsulfonyl)benzamide | 406 |

-continued

| Ex | NAME | MS (m/z) |
|---|---|---|
| 231 | 4-[(4-chloro-2-fluorobenzyl)oxy]-2,5-difluoro-N-(methylsulfonyl)benzamide | 394 |
| 232 | 4-[(2-chloro-4-fluorobenzyl)oxy]-2,5-difluoro-N-(methylsulfonyl)benzamide | 394 |
| 233 | 2,5-difluoro-4-[(2-methoxybenzyl)oxy]-N-(methylsulfonyl)benzamide | 372 |

The skilled person will appreciate that where in the above Examples the compound of formula (I) was prepared in the form of a salt, the same may be converted into the corresponding free base or free acid under conventional conditions (or, in the case of a salt arising from purification by the Auto-HPLC conditions described above in the preamble to the Examples, by use of appropriate alternative preparative HPLC conditions).

In particular, the following compounds of formula (I) may be prepared:

N-(methylsulfonyl)-4-({4-[1-methyl-3-(trifluoromethyl)-1H-pyrazol-5-yl]phenoxy}methyl)benzamide;

4-[(3-methoxyphenoxy)methyl]-Nethylsulfonyl)benzamide;

4-((3,4-dichlorophenoxy)methyl)-2,5-difluoro-N-(methylsulfonyl)benzamide;

4-((4-chloro-2-methoxyphenoxy)methyl)-2,5-difluoro-N-(methylsulfonyl)benzamide;

4-((3-chlorophenoxy)methyl)-N-(methylsulfonyl)benzamide;

4-((4-chlorophenoxy)methyl)-N-(methylsulfonyl)benzamide;

4-(benzyloxy)-N-(methylsulfonyl)benzamide;

4-((2,4-dichlorophenoxy)methyl)-N-(methylsulfonyl)benzamide;

4-((4-ethylphenoxy)methyl)-N-(methylsulfonyl)benzamide;

3-chloro-4-((3,4-dichlorophenoxy)methyl)-N-(methylsulfonyl)benzamide;

N-(methylsulfonyl)-4-[(4-piperidin-4-ylphenoxy)methyl]benzamide;

4-{[4-(1-methyl-1H-pyrazol-5-yl)phenoxy]methyl}-N-(methylsulfonyl)benzamide;

4-{[4-chloro-2-(1-methyl-1H-pyrazol-5-yl)phenoxy]methyl}-N-(methylsulfonyl)benzamide;

3-chloro-4-[(4-ethylphenoxy)methyl]-Nethylsulfonyl)benzamide;

4-[(4-ethylphenoxy)methyl]-2-fluoro-N-(methylsulfonyl)benzamide;

4-[(4-ethylphenoxy)methyl]-2-methoxy-N-(methylsulfonyl)benzamide;

4-[(4-ethylphenoxy)methyl]-3-methoxy-N-(methylsulfonyl)benzamide;

4-[(4-ethylphenoxy)methyl]-2-methyl-N-(methylsulfonyl)benzamide;

4-(4-chloro-3-cyanobenzyloxy)-2,5-difluoro-N-(methylsulfonyl)benzamide; and 5-cyano-4-((3,4-dichlorophenoxy)methyl)-N-(methylsulfonyl)benzamide.

Preparation 1

1-Bromo-5-chloro-4-[(3,4-dichlorophenoxy)methyl]-2-fluorobenzene

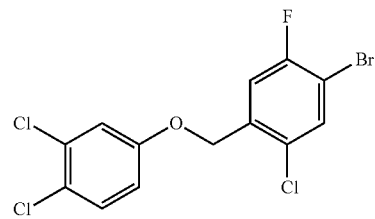 [SMILES: Fc1cc(COc2ccc(Cl)c(Cl)c2)c(Cl)cc1Br]

A mixture of 3,4 dichlorophenol (730 mg, 4.48 mmol), 1-bromo-4-(bromomethyl)-5-chloro-2-fluorobenzene (Preparation 2, 1.35 g, 4.48 mmol), and potassium carbonate (1.87 g, 13.5 mmol) in acetone (56 mL) was stirred for 72 hours at room temperature under a nitrogen atmosphere. The reaction mixture was diluted with ethyl acetate (100 mL) and filtered through Arbocel™. The Arbocel™ was washed with ethyl acetate (2×50 mL) and the combined organic extracts were concentrated in vacuo to afford a pale yellow solid. The solid was then dissolved in ethyl acetate (150 mL) and washed successively with aqueous sodium hydroxide solution (0.5 M, 100 mL), brine (3×100 mL), dried over sodium sulphate, filtered and concentrated in vacuo to afford an off white solid (1.90 g). Recrystallisation from hot heptane afforded the title compound (920 mg, 53%) as a white solid.

$^1$H NMR (400 MHz, CDCl$_3$): δ 5.06 (s, 2H), 6.84 (dd, 1H), 7.10 (d, 1H), 7.34 (d, 1H), 7.37 (d, 1H), 7.63 (d, 1H).

LCMS Rt=4.25 minutes MS m/z 382 [MH]+

Preparation 2

1-Bromo-4-(bromomethyl)-5-chloro-2-fluorobenzene

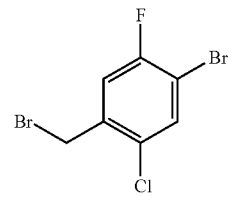

A solution of 4-bromo-2-chloro-5-fluorotoluene (997 mg, 4.46 mmol), N-bromosuccinimide (837 mg, 4.70 mmol) and benzoyl peroxide (35 mg, 0.14 mmol) in carbon tetrachloride (20 mL) was heated to reflux at 85° C. for 18.5 hours under nitrogen. The reaction mixture was concentrated in vacuo to afford a cream solid residue. The residue was suspended in heptane (40 mL), filtered and the filtrate then concentrated in vacuo to afford the title compound a clear oil (1.35 g, 100%). The compound was used without further purification in the next step.

$^1$H NMR (400 MHz, CDCl$_3$): δ 4.50 (s, 2H), 7.24 (d, 1H), 7.62 (d, 1H).

Preparation 3

2,5-Difluoro-4-methyl-N-(methylsulfonyl)benzamide

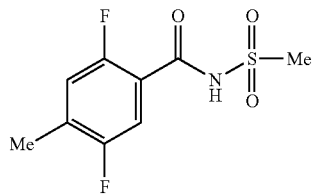 [SMILES: Cc1cc(F)c(C(=O)NS(C)(=O)=O)cc1F]

A mixture of 2-5-difluoro-4-methylbenzoic acid (6.0 g, 34.9 mmol), diisopropylethylamine (13.5 g, 105.0 mmol), propanephosphonic acid cyclic anhydride (50 mL, 50% w/w solution in ethyl acetate, 84.0 mmol) and methyl sulphonamide (6.6 g, 69.7 mmol) in tetrahydrofuran (200 mL) was heated under reflux with stirring under N$_2$ for 18 hours. After cooling, the solution was evaporated in vacuo and the residue suspended in water. The mixture was extracted with ethyl acetate (300 mL) and the organic extract then washed with brine (2×80 mL). The organic solution was then dried over sodium sulphate and evaporated in vacuo to give a solid. Trituration with hexane gave the title compound (7.6 g, 87%) as an off white solid after drying.

$^1$H NMR (400 MHz, d$_6$-DMSO): δ 2.26 (s, 3H), 3.34 (s, 3H), 7.33 (m, 1H), 7.44 (m, 1H).

LCMS Rt=1.24 minutes MS m/z 248 [M−H]−

Preparation 4

4-(Bromomethyl)-2,5-difluoro-N-(methylsulfonyl)benzamide

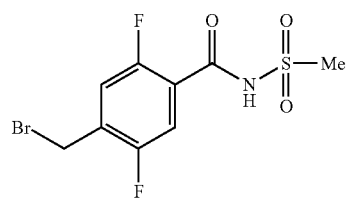

A stirred mixture of 2,5-difluoro-4-methyl-N-(methylsulfonyl)benzamide (Preparation 3, 5.07 g, 20.3 mmol), N-bromosuccinimide (freshly recrystallised and dried, 4.71 g, 26.4 mmol) and azobisisobutyronitrile (0.05 g, 0.30 mmol) in 1,2-dichloroethane (100 mL) was heated at reflux under nitrogen whilst being irradiated with light from a lamp. After 2 hours, additional azobisisobutyronitrile (0.05 g, 0.30 mmol) was added and the reaction heated under reflux for a further 2 hours. The reaction mixture was cooled to room temperature and evaporated in vacuo. The residue was partitioned between brine (200 mL) and ethyl acetate (2×150 mL). The combine extracts were dried over magnesium sulphate and evaporated in vacuo to give a pale yellow oil which solidified on standing (7.88 g). Purification by flash column chromatography using the ISCO™ system (120 g cartridge), loading in dichloromethane (20 mL) with an eluant of heptane to 20% ethylacetate/heptane to 30% ethylacetate/heptane gave the title compound (3.71 g, 56%) as a white solid.

$^1$H NMR (400 MHz, d$_6$-DMSO): δ 3.34 (s, 3H), 4.69 (s, 2H), 7.58 (m, 2H).

LCMS Rt=1.37 minutes MS m/z 328 [M−H]−

Preparation 5

3-Chloro-4-(trifluoromethyl)phenol

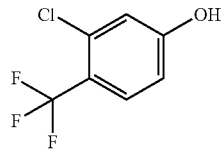

To a stirred solution of 2-chloro-4-fluorobenzotrifluoride (500 mg, 2.52 mmol) in anhydrous N,N-dimethylformamide (10 mL) was added 2-(trimethylsilyl)ethanol (0.40 mL, 2.77 mmol) and the reaction mixture was cooled to 0° C. Sodium hydride (302 mg, 60% w/w dispersion in oil, 7.55 mmol) was then added portionwise. After 5 minutes a thick white suspension had formed. The reaction mixture was warmed to room temperature slowly and then stirred for a further 16 hours. The reaction mixture was then quenched with ice water (50 mL) and washed with diethyl ether (50 mL). The aqueous extracts were acidified with aqueous 2 M hydrogen chloride solution and extracted with diethyl ether (2×50 mL). The organic extracts were dried over anhydrous magnesium sulphate and evaporated in vacuo for 16 hours to afford the title compound as a yellow oil (356 mg, 72%).

$^1$H NMR (400 MHz, CDCl$_3$): δ 6.75 (dd, 1H), 6.95 (d, 1H), 7.51 (d, 1H).

LCMS Rt=1.23 minutes MS m/z 195 [M−H]−

Preparation 6

4-[1-Methyl-3-(trifluoromethyl)-1H-pyrazol-5-yl]phenol

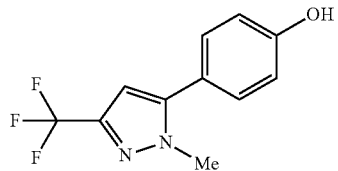 [SMILES: Cn1nc(C(F)(F)F)cc1-c1ccc(O)cc1]

To a solution of 4-iodophenol (75 mg, 0.34 mmol) in a mixture of water (1 mL) and 1,4-dioxane (2 mL) was added [1-methyl-3-(trifluoromethyl)-1H-pyrazol-5-yl]boronic acid (Preparation 7, 90 mg, 0.46 mmol), dichlorobis(triphenylphosphine)palladium(II) (18.3 mg, 0.03 mmol) and cesium carbonate (240 mg, 0.74 mmol). The resulting mixture was heated at 90° C. in a Reactivial™ for 4 hours. The reaction mixture was cooled to room temperature and partitioned between ethyl acetate (10 mL) and brine (2×10 mL). The organic extract was dried over anhydrous sodium sulfate and evaporated in vacuo. The crude material was purified by flash column chromatography using the ISCO™ system (12 g column), eluting with 70:30 heptane/ethyl acetate. Fractions containing product were combined and concentrated in vacuo to afford the title compound as a white solid (61 mg, 73%).

$^1$H NMR (400 MHz, d$_6$-DMSO): δ 4.90 (s, 3H), 6.75 (s, 1H), 6.90 (d, 2H), 7.40 (d, 2H), 9.80 (s, 1H).

LCMS: Rt=1.41 minutes MS m/z 242 [MH]+

Preparation 7

[1-Methyl-3-(trifluoromethyl)-1H-pyrazol-5-yl]boronic acid

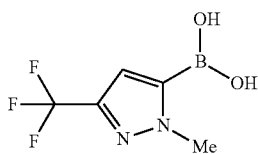 [SMILES: Cn1nc(C(F)(F)F)cc1B(O)O]

To a stirred solution of 1-methyl-3-(trifluoromethyl)-1H-pyrazole (1.89 g, 12.6 mmol) in anhydrous tetrahydrofuran (20 mL) under nitrogen cooled to −78° C. was added n-butyllithium (8.3 mL, 1.6 M solution in hexanes, 13.2 mmol) slowly over 5 minutes. The resulting yellow solution was stirred at −78° C. for 1 hour and trimethyl borate (1.56 mL, 13.9 mmol) was then added slowly. The reaction flask was covered in foil and allowed to warm to room temperature for 16 hours. The white solution was quenched with aqueous 1 M hydrogen chloride solution (10 mL) and stirred at room temperature for 1.5 hours. The mixture was extracted with ethyl acetate (2×30 mL), dried with anhydrous magnesium sulphate and evaporated in vacuo to give an off-white foam (2.11 g). The foam was triturated with dichloromethane, filtered and dried in vacuo to afford the title compound as a white solid (1.57 g, 64%).

$^1$H NMR (400 MHz, MeOH-d4): δ 4.04 (s, 3H), 6.89 (s, 1H).

LCMS Rt=1.11 minutes MS m/z 194 [MH]+ 192 [M−H]−,

Preparation 8

Methyl 4-[(3,4-dichlorobenzyl)oxy]benzoate

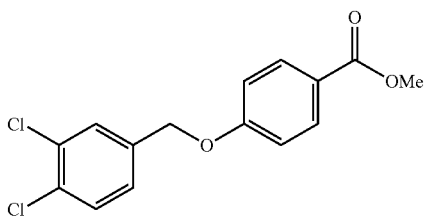 [SMILES: COC(=O)c1ccc(OCc2ccc(Cl)c(Cl)c2)cc1]

To a suspension of methyl 4-hydroxybenzoate (366 mg, 2.41 mmol) and sodium hydride (116 mg, 60% w/w dispersion in oil, 2.65 mmol) in tetrahydrofuran (12 mL) was added 3,4-dichlorobenzyl bromide (578 mg, 2.41 mmol) and the reaction mixture was stirred at room temperature for 48 hours. The reaction was quenched by addition of methanol (15 mL) and was then evaporated to dryness. The resulting residue was purified by flash column chromatography using ethyl acetate/heptane as eluant. The title compound was isolated as a white solid (750 mg, 100%).

$^1$H NMR (400 MHz, acetone-d$_6$): δ 3.84 (s, 3H), 5.26 (s, 2H), 7.12 (m, 1H), 7.14 (m, 1H), 7.48-7.51 (m, 1H), 7.62 (d, 1H), 7.73 (m, 1H), 7.97 (m, 1H), 7.99 (m, 1H).

LCMS Rt=1.90 minutes MS m/z 267 [M−CO2]+

Preparation 9

4-[(3,4-Dichlorobenzyl)oxy]benzoic acid

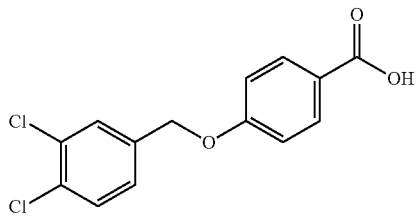 [SMILES: O=C(O)c1ccc(OCc2ccc(Cl)c(Cl)c2)cc1]

To a solution of methyl 4-[(3,4-dichlorobenzyl)oxy]benzoate (Preparation 8, 750 mg; 2.41 mmol) in tetrahydrofuran (12 mL) was added an aqueous solution of lithium hydroxide (2 M, 6 mL, 12 mmol) and the reaction stirred at reflux for 4 hours. Upon consumption of starting material the reaction mixture cooled to room temperature and solvent removed in vacuo. The resulting residue was dissolved in water (15 mL) and acidified with 2M hydrochloric acid solution. The aqueous phase was then extracted with dichloromethane (3×25 mL). The combined organic extracts were dried over magnesium sulphate, filtered and evaporated in vacuo to give the title compound (620 mg, 87%) as a white solid.

$^1$H NMR (400 MHz, d$_6$-DMSO): δ 5.16 (s, 2H), 6.98 (m, 1H), 7.00 (m, 1H), 7.44 (m, 1H), 7.64 (m, 1H), 7.71 (m, 1H), 7.83 (m, 1H), 7.86 (m, 1H).

LCMS Rt=1.75 minutes MS m/z 294 [M−H]−

Preparation 10

Methyl-3-chloro-4-[(3,4-difluorobenzyl)oxy]benzoate

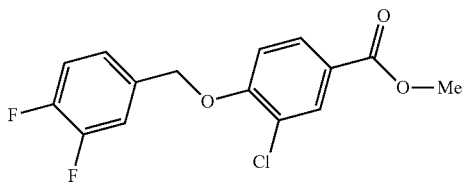 [SMILES: COC(=O)c1ccc(OCc2ccc(F)c(F)c2)c(Cl)c1]

To a stirred solution of methyl 3-chloro-4-hydroxybenzoate (comm, 6.48 g, 34.73 mmol) in acetonitrile was added cesium carbonate (28.29 g, 86.82 mmol) followed by 4-(bromomethyl)-1,2-difluorobenzene (comm, 10.78 g, 52.09 mmol). The reaction mixture was stirred at room temperature for 18 hours. A sodium hydroxide solution (0.5 M, 210 mL) was then added and the resulting white solid was collected by filtration to yield the title compound, which was used in the next step without further purification.

$^1$H NMR (400 MHz, $d_6$-DMSO): δ 3.77 (s, 3H), 5.22 (s, 2H), 7.16 (d, 1H), 7.26-7.32 (m, 1H), 7.39-7.53 (m, 2H), 7.77 (dd, 1H), 7.85 (d, 1H).

Preparation 11

3-chloro-4-[(3,4-difluorobenzyl)oxy]benzoic acid

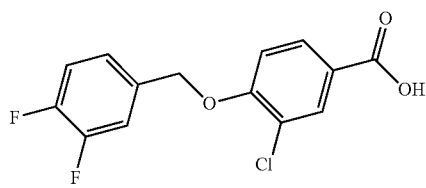 [SMILES: O=C(O)c1ccc(OCc2ccc(F)c(F)c2)c(Cl)c1]

To a stirred solution of methyl 3-chloro-4-[(3,4-difluorobenzyl)oxy]benzoate (Preparation 10, 10.86 g, 34.7 mmol) in methanol (700 mL) and water (150 mL) was added sodium hydroxide (6.946 g, 173.7 mmol) and the resulting reaction mixture was stirred at room temperature for 18 hours. The reaction mixture was concentrated in vacuo, diluted with water (285 mL), adjusted to pH 3 with hydrochloric acid and the resulting precipitate collected by filtration, washed with water and the azeotroped with toluene in vacuo twice to yield the title compound as a solid (6.5 g, 62% over 2 steps).

$^1$H NMR (400 MHz, $d_6$-DMSO): δ 5.18 (s, 2H), 7.16 (d, 1H), 7.25-7.32 (m, 1H), 7.39-7.53 (m, 2H), 7.78 (dd, 1H), 7.85 (d, 1H).

Preparation 12

Methyl 5-chloro-2-fluoro-4-methyl benzoate

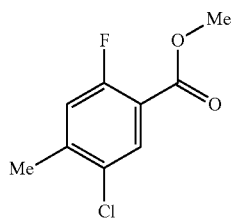 [SMILES: COC(=O)c1cc(Cl)c(C)cc1F]

To a solution of 1-bromo-5-chloro-2-fluoro-4-methylbenzene (Comm, 10 g, 44.7 mmol) in methanol (200 mL) was added 1,1'-binaphthalene-2,2'-diylbis(diphenylphosphine)-dichloropalladium (1:1) (358 mg, 0.447 mmol) and N,N-diethylethanamine (8.11 mL, 58.2 mmol). The resulting mixture was placed in a bomb and pressurized with carbon monoxide to 80 psi and heated at 80° C. for 18 hours. The reaction mixture was then concentrated in vacuo to yield a semi-solid, which was dissolved in EtOAc (300 mL) and washed with water (200 mL). The organic layer was separated, dried over magnesium sulphate, filtered and concentrated in vacuo to yield an orange oil, which solidified on standing (9.87 g). The solid was purified by silica gel chromatography eluting with 0 to 20% EtOAc in heptane to afford the title compound as a crystalline white solid (8.47 g, 93%).

$^1$H NMR (400 MHz, $CDCl_3$): δ 2.40 (s, 3H), 3.92 (s, 3H), 7.03 (d, 1H), 7.91 (d, 1H)

LCMS Rt=1.64 minutes Molecular ion not observed

Preparation 13

5-Chloro-2-fluoro-4-methylbenzoic acid

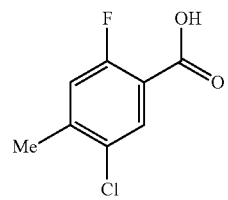

To a stirred solution of methyl 5-chloro-2-fluoro-4-methylbenzoate (Preparation 12, 340 mg, 1.68 mmol) in dioxane/water (5:1, 12 mL) was added a sodium hydroxide solution (5 M, 1.63 mL, 8.39 mmol). The reaction mixture was stirred at room temperature for 18 hours and then evaporated in vacuo. The resulting residue was suspended in water and extracted with diethyl ether (3×20 mL). The aqueous layer was separated, cooled in an ice bath, acidified with aqueous hydrochloric acid (6 M) and then extracted with EtOAc (30 mL). The combined organics were washed with brine (2×20 mL), dried over sodium sulphate, filtered and evaporated in vacuo to yield the title compound as a white solid (266 mg, 84%).

$^1$H NMR (400 MHz, $d_6$-DMSO): δ 2.36 (s, 3H), 7.38 (dd, 1H), 7.80 (d, 1H).

LCMS Rt=1.39 minutes MS m/z 187 [M−H]−

Preparation 14

5-Chloro-2-fluoro-4-methyl-N-(methylsulfonyl)benzamide

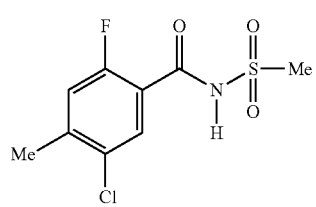 [SMILES: Cc1cc(F)c(C(=O)NS(C)(=O)=O)cc1Cl]

To 5-chloro-2-fluoro-4-methylbenzoic acid (Preparation 13, 200 g, 1.06 mol) in DCM (1.4 L) was added methanesulphonamide (152 g, 1.6 mol), 4-(dimethylamino)pyridine (183 g 1.6 mol) and N-(3-dimethylaminopropyl)-N'-ethylcarbodiimide hydrochloride (306 g, 1.6 mol). The reaction mixture spontaneously heated at 30° C. over 30 minutes, then it was stirred at room temperature for 18 hours under a nitrogen atmosphere. The reaction was washed with aqueous hydrochloric acid (4 M, 0.8 L). The organic layer was separated, washed with water (500 mL), dried over sodium sulphate and concentrated in vacuo to yield a tan solid, which was recrystallised from hot EtOAc (0.9 L) by addition of n-heptane (100 mL) and cooling to yield the title compound (118 g, 45%).

$^1$H NMR (400 MHz, $CDCl_3$): δ 2.42 (s, 3H), 3.42 (s, 3H), 7.10 (d, 1H), 8.05 (d, 1H), 8.78 (br, 1H).

Preparation 15

4-(Bromomethyl)-5-chloro-2-fluoro-N-(methylsulfonyl)benzamide

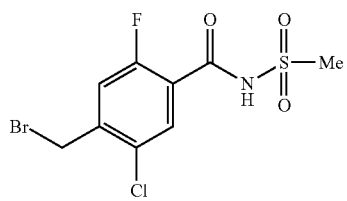 [SMILES: CS(=O)(=O)NC(=O)c1cc(Cl)c(CBr)cc1F]

To a suspension of 5-chloro-2-fluoro-4-methyl-N-(methylsulfonyl)benzamide (Preparation 14, 118 g, 0.45 mol) in 1,2-dichloroethane (1.25 L) was added N-bromosuccinimide (91 g, 0.51 mol) and benzoyl peroxide (5 g, 20 mmol) and the mixture heated to reflux for 18 hours. N-bromosuccinimide (30 g, 0.17 mol) was then added and the solution heated 24 hours more. A further portion of N-bromosuccinimide (20 g, 0.11 mol) was added and the solution heated for 3 hours, then cooled and washed with water (1 L) containing aqueous sodium thiosulphate solution (200 mL, 0.5 M). The organic layer was washed with water (500 mL), dried over sodium sulphate and concentrated in vacuo to yield a crude solid. To a solution of this crude solid in EtOAc (1 L) was added diisopropylethylamine (130 mL, 0.75 mol) and diethyl phosphite (27.6 g, 0.2 mol) and the mixture stirred for 5 hours under nitrogen, then washed with aqueous hydrochloric acid (1 L, 2 M), dried over magnesium sulphate and evaporated to yield a dark solid. Trituration with diethyl ether (200 mL) gave the first crop of title compound as a tan solid (68 g). The filtrate was purified by silica gel chromatography eluting with 10% EtOAc in DCM containing acetic acid (1%), followed by crystallization from acetonitrile (130 mL) to yield the second crop of the title compound (30 g).

$^1$H NMR (400 MHz, CDCl$_3$): δ 3.41 (s, 3H), 4.54 (s, 2H), 7.38 (d, 1H), 8.14 (d, 1H), 8.78 (br, 1H).

Preparation 16

2,4,5-Trifluoro-N-(methylsulfonyl)benzamide

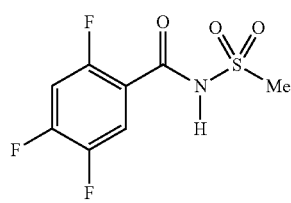 [SMILES: CS(=O)(=O)NC(=O)c1cc(F)c(F)cc1F]

2,4,5-Trifluorobenzoic acid (3.00 g, 17.0 mmol), N-ethyl-N-isopropylpropan-2-amine (8.9 mL, 6.6 g, 51.1 mmol), 2,4,6-tripropyl-1,3,5,2,4,6-trioxatriphosphorinane-2,4,6-trioxide 50% solution in EtOAc/DMF (12.7 mL, 13.6 g, 42.6 mmol) and methanesulfonamide (3.24 g, 34.1 mmol) were suspended in THF (40 mL) and stirred under a nitrogen atmosphere at reflux for 18 hours. The reaction mixture was cooled, concentrated in vacuo and the residue suspended in water (pH=4). The mixture was acidified to pH=2 with an aqueous solution of potassium hydrogen sulfate (0.5 M). The mixture was extracted with EtOAc (1×100 mL). The organic layer was washed with brine (2×50 mL), dried over sodium sulfate, filtered and evaporated to yield the crude solid. The crude solid was triturated with hexane to yield the title compound as an off-white crystalline solid (3.08 g).

$^1$H NMR (400 MHz, CDCl$_3$): δ 3.45 (s, 3H), 7.10-7.13 (m, 1H), 7.97-8.02 (m, 1H), 8.74 (brs, 1H).
$^{19}$FNMR (400 MHz, CDCl$_3$): δ −112.4, −121.9, −138.5.

Preparation 17

4-tert-Butoxy-2,5-difluoro-N-(methylsulfonyl)benzamide

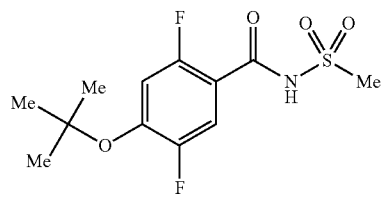 [SMILES: CC(C)(C)Oc1cc(F)c(C(=O)NS(C)(=O)=O)cc1F]

To a solution of 2,4,5-trifluoro-N-(methylsulfonyl)benzamide (Preparation 16, 1.50 g, 5.92 mmol) in DMSO (10 mL) at room temperature was added potassium t-butoxide (1.46 g, 13.0 mmol). After 18 hours the reaction mixture was diluted with EtOAc (30 mL) and 10% aqueous citric acid solution (15 mL). The pH of the aqueous layer was checked to ensure it was acidic. The organic layer was separated and washed with 10% aqueous citric acid solution (15 mL) and brine (15 mL), dried over magnesium sulphate, filtered and evaporated to yield the title compound as a cream solid (1.76 g, 97%).

$^1$H NMR (400 MHz, CDCl$_3$): δ 1.45 (s, 9H), 3.42 (s, 3H), 6.88-6.93 (m, 1H), 7.80-7.87 (m, 1H), 8.70-8.85 (br, 1H).

LCMS Rt=2.54 minutes MS m/z 306 [M−H]−

Preparation 18

2,5-Difluoro-4-hydroxy-N-(methylsulfonyl)benzamide

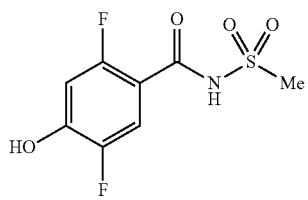 [SMILES: CS(=O)(=O)NC(=O)c1cc(F)c(O)cc1F]

4-tert-Butoxy-2,5-difluoro-N-(methylsulfonyl)benzamide (Preparation 17, 1.76 g, 5.73 mmol) was added to hydrochloric acid solution in dioxane (4 M, 30 mL) at room temperature and stirred for 3 hours. The solvent was then evaporated and the resulting residue dissolved in DCM. The solvent was evaporated again to yield the title compound as a white solid (1.4 g, 100%), which was used in the next stage without further purification.

$^1$H NMR (400 MHz, CDCl$_3$): δ 3.25 (s, 3H), 6.60-6.68 (m, 1H), 7.45-7.55 (m, 1H), 9.80-9.95 (brs, 1H), 10.50-10.65 (brs, 1H).

LCMS Rt=0.71 minutes MS m/z 252 [MH]+

Preparation 19

1-Bromo-4-(3-chloro-4-(trifluoromethyl)benzyloxy)-2,5-difluorobenzene

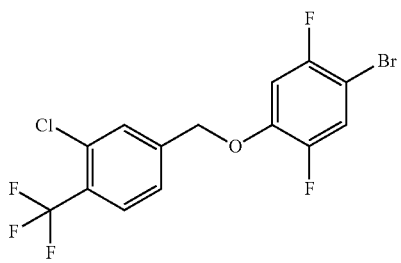 [SMILES: Fc1cc(OCc2ccc(C(F)(F)F)c(Cl)c2)c(F)cc1Br]

To solution of 3-chloro-4-(trifluoromethyl)benzyl bromide (300 mg, 1.097 mmol) in acetone (15 mL) was added 4-bromo-2,5-difluorophenol (1.097 mmol) followed by potassium carbonate (303 mg, 2.194 mmol). The reaction mixture was heated at reflux for 3.5 hours and then allowed to cool to room temperature. The solvent was removed under reduced pressure to yield a white solid, which was partitioned with water/EtOAc mixture (1:1, 50 mL). The organic layer was separated and the aqueous was extracted with EtOAc (3×30 mL). The combined organics were washed with brine (50 mL), dried over sodium sulphate, filtered and concentrated in vacuo to give the title compound as a white solid (434 mg, 99%).

$^1$H NMR (400 MHz, CDCl$_3$): δ 5.12 (s, 2H), 6.79 (dd, 1H), 7.32 dd, 1H), 7.41-7.43 (m, 1H), 7.59 (s, 1H), 7.72 (d, 1H).

LCMS Rt=4.08 minutes Molecular ion not observed

Preparation 20

2,5-Difluoro-4-formylbenzonitrile

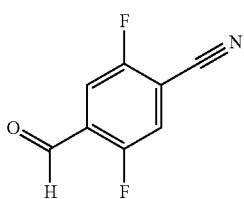 [SMILES: N#Cc1cc(F)c(C=O)cc1F]

n-Butyllithium solution (1.6 M in hexanes, 8.75 mL, 14 mmol) was added dropwise to a solution of methyl methylthiomethyl sulfoxide (1.58 g, 12.7 mmol) in THF (25 mL) at −78° C. After 30 minutes at −78° C., 2,4,5-trifluorobenzonitrile (commercial, 1 g, 6.35 mmol) was added dropwise. The solution was then allowed to warm to room temperature, and stirred for 18 hours under a nitrogen atmosphere. The deep red reaction mixture was poured into water (75 mL), and extracted with EtOAc (2×75 mL). The combined organics were dried over magnesium sulphate and evaporated to yield a brown oil. The oil was redissolved in THF (15 mL) and concentrated sulphuric acid (4.1 mL, 77.2 mmol) and water (4 mL) were added. After stirring for 5 hours the reaction was quenched with saturated aqueous sodium bicarbonate (30 mL) and extracted with EtOAc (2×50 mL). The combined organic extracts were dried over magnesium sulphate, and evaporated to yield a brown oil, which was purified by silica gel chromatography eluting with 50% heptane in DCM to afford the title compound as a yellow oil (280 mg, 26%).

$^1$H NMR (400 MHz, CDCl$_3$): δ 7.53 (dd, 1H), 7.70 (dd, 1H), 10.35 (s, 1H).

LCMS Rt=2.71 minutes MS m/z 262 [M+H]$^+$

Preparation 21

2,5-Difluoro-4-(hydroxymethyl)benzonitrile

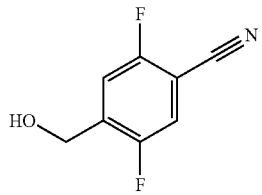 [SMILES: N#Cc1cc(F)c(CO)cc1F]

A solution of 2,5-difluoro-4-formylbenzonitrile (Preparation 20, 280 mg, 1.68 mmol) in ethanol (8 mL) was cooled to 0° C. in an ice/water bath. Sodium borohydride (63.4 mg, 1.68 mmol) was added and the reaction stirred at 0-5° C. for 5 hours. The mixture was quenched with aqueous hydrochloric acid (2 N, 20 mL) and extracted with EtOAc (25 mL). The organic layer was washed with saturated aqueous sodium bicarbonate (25 mL), dried over sodium sulphate, and concentrated in vacuo to afford the title compound as a yellow oil, which crystallised on standing (182 mg, 64%).

$^1$H NMR (400 MHz, CDCl$_3$): δ 4.83 (s, 2H), 7.28 (dd, 1H), 7.43 (dd, 1H).

LCMS Rt=1.57 minutes MS m/z 167 [MH]$^+$

Preparation 22

2,5-Difluoro-4-(bromomethyl)benzonitrile

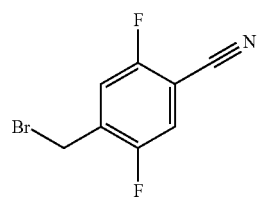 [SMILES: N#Cc1cc(F)c(CBr)cc1F]

To a stirred solution of 2,5-difluoro-4-(hydroxymethyl) benzonitrile (Preparation 21, 390 mg, 2.30 mmol) in DCM (12 mL) was added phosphorus tribromide (0.238 mL, 2.53 mmol). The mixture was stirred at room temperature for 18 hours. The reaction mixture was then diluted with DCM to 30 mL and washed with saturated aqueous sodium bicarbonate (30 mL). The organic layer was dried over sodium sulphate, and evaporated to afford the title compound as a yellow oil, which was used in the next step without further purification (530 mg, 99%).

$^1$H NMR (400 MHz, CDCl$_3$): δ 4.40 (s, 2H), 7.30 (dd, 1H), 7.34 (dd, 1H).

Preparation 23

4-((3,4-Dichlorophenoxy)methyl)-2,5-difluorobenzonitrile

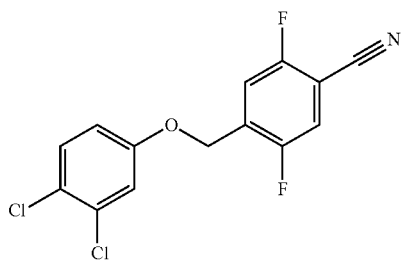 [SMILES: N#Cc1cc(F)c(COc2ccc(Cl)c(Cl)c2)cc1F]

To a stirred solution of 2,5-difluoro-4-(bromomethyl)benzonitrile (Preparation 22, 530 mg, 2.30 mmol) and 3,4-dichlorophenol (375 mg, 2.30 mmol) in acetone (12 mL) was added potassium carbonate (954 mg, 6.90 mmol). The mixture was stirred at room temperature for 36 hours. The reaction mixture was then poured into water (25 mL) and extracted with EtOAc (3×25 mL). The combined organics were dried over sodium sulphate and evaporated to yield the crude product as a yellow oil, which was purified by silica gel chromatography eluting with 50% heptanes in DCM to afford the title compound as a white solid (153 mg, 22%).

$^1$H NMR (400 MHz, CDCl$_3$): δ 5.10 (s, 2H), 6.83 (dd, 1H), 7.10 (d, 1H), 7.30 (dd, 1H), 7.35-7.40 (m, 1H), 7.43 (dd, 1H).

LCMS Rt=1.57 minutes MS m/z 314 [M+H]$^+$

Preparation 24

4-((3,4-Dichlorophenoxy)methyl)-2,5-difluorobenzamide

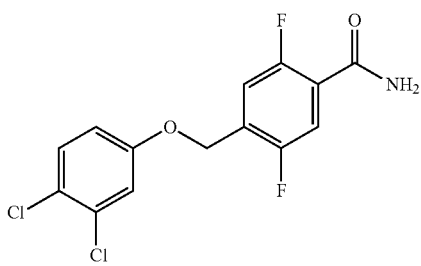 [SMILES: NC(=O)c1cc(F)c(COc2ccc(Cl)c(Cl)c2)cc1F]

To a stirred solution of 4-((3,4-dichlorophenoxy)methyl)-2,5-difluorobenzonitrile (Preparation 23, 153 mg, 0.481 mmol) in DMSO (5 mL) was added potassium carbonate (133 mg, 0.962 mmol), followed by dropwise addition of 30% aqueous hydrogen peroxide solution (0.29 mL, 2.90 mmol). After 3 hours, the reaction was quenched with saturated aqueous potassium bisulphate solution (10 mL), and extracted with DCM (3×10 mL). The combined organics were washed with brine (2×10 mL), dried over magnesium sulphate, and concentrated in vacuo to afford the title compound as a white solid (60 mg, 38%).

$^1$H NMR (400 MHz, CDCl$_3$): δ 5.20 (s, 2H), 6.82 (dd, 1H), 7.10 (d, 1H), 7.33 (dd, 1H), 7.38 (d, 1H), 7.87 (dd, 1H).

LCMS Rt=2.91 minutes MS m/z 330 [M−H]$^-$

Preparation 25

4-[(3,4-Dichlorobenzyl)oxy]-2-methoxybenzaldehyde

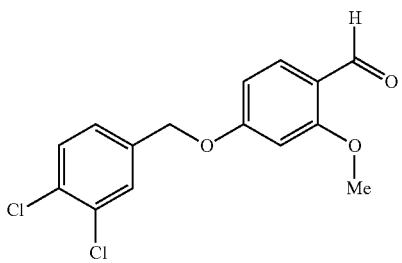 [SMILES: COc1cc(OCc2ccc(Cl)c(Cl)c2)ccc1C=O]

A solution of 4-hydroxy-2-methoxybenzaldehyde (300 mg, 1.97 mmol) in DMSO (7.5 mL) was added potassium carbonate (545 mg, 3.94 mmol) the resulting suspension was stirred under nitrogen at room temperature for 10 minutes. 4-(Bromomethyl)-1,2-dichlorobenzene was then added (commercial, 473 mg, 1.32 mmol) and the reaction mixture heated to 90° C. for 3 hours. The reaction mixture was cooled to room temperature and partitioned between EtOAc (50 mL) and water (40 mL). The organic layer was washed with water (2×40 mL), dried over magnesium sulphate and evaporated in vacuo to yield the title compound as a solid (530 mg, 86%):

$^1$H NMR (400 MHz, CDCl$_3$): δ 3.90 (s, 3H), 5.08 (s, 2H), 6.53 (d, 1H), 6.58 (dd, 1H), 7.26 (dd, 1H+CDCl$_3$ peak), 7.48 (d, 1H), 7.55 (d, 1H), 7.82 (d, 1H), 10.30 (s, 1H).

LCMS Rt=1.80 minutes MS m/z 311 [MH]+

Preparation 26

Methyl 2,5-difluoro-4-methylbenzoate

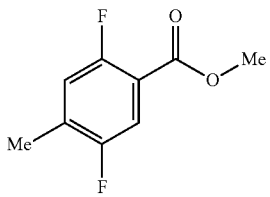 [SMILES: COC(=O)c1cc(F)c(C)cc1F]

To a suspension of 4-methyl-2,5-difluorobenzoic acid (comm, 52 g, 0.3 mol) in methanol (1.0 L) was added concentrated sulphuric acid (3 mL) with stirring and the reaction heated to reflux under nitrogen for 18 hours. The reaction was quenched with aqueous sodium bicarbonate solution (10%, 150 mL), concentrated in vacuo and the resulting residue partitioned between EtOAc (800 mL) and water (400 mL). The organic layer was washed with water (250 mL) and brine (100 mL), dried with sodium sulphate and concentrated in vacuo to yield the title compound as a clear oil that solidified on standing (54.7 g, 98%).

$^1$H NMR (400 MHz, CDCl$_3$): δ 2.33 (s, 3H), 3.92 (s, 3H), 6.98 (m, 1H), 7.58 (m, 1H).

Preparation 27

Methyl 4-(bromomethyl)-2,5-difluorobenzoate

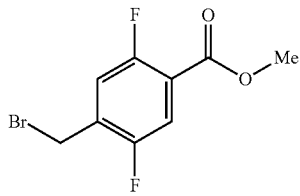 [SMILES: COC(=O)c1cc(F)c(CBr)cc1F]

To methyl 2,5-difluoro-4-methylbenzoate (Preparation 26, 55 g, 0.29 mol) in carbon tetrachloride (0.4 L) was added N-bromosuccinimide (52.6 g, 0.29 mol) and dibenzoyl peroxide (1 g, 3.5 mmol) and heated at 88° C. for 5 hours under a nitrogen atmosphere. The reaction mixture was cooled to room temperature and allowed to stand for 18 hours, then washed with water (400 mL), brine (100 mL), dried over sodium sulphate and concentrated in vacuo. The resulting solid was triturated with n-heptane (120 mL) and recrystallised from hot n-heptane (50 mL) to yield the title compound as a pale yellow solid (28.5 g, 36%).

$^1$H NMR (400 MHz, CDCl$_3$): δ 3.94 (s, 3H), 4.44 (s, 2H), 7.18 (m, 1H), 7.64 (m, 1H).

Preparation 28

Methyl 2,5-difluoro-4-[(3-methoxyphenoxy)methyl]benzoate

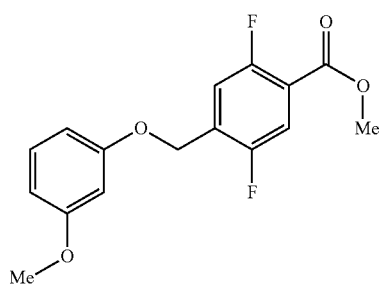 [SMILES: COC(=O)c1cc(F)c(COc2cccc(OC)c2)cc1F]

To a solution of 3-methoxyphenol (221 mg, 1.8 mmol) in DMSO (5 mL) was added methyl 4-(bromomethyl)-2,5-difluorobenzoate (Preparation 27, 491 mg, 1.8 mmol) followed by potassium carbonate (491 mg, 3.5 mmol) and the reaction mixture was stirred at room temperature under nitrogen for 18 hours. The mixture was poured into water and extracted with EtOAc (3×20 mL), washed with 1 M aqueous NaOH and water, dried over magnesium sulphate and the solvent removed under reduced pressure to yield the title compound as a solid, which was taken to the next step without further purification (441 mg, 81%).

LCMS Rt=3.31 minutes MS m/z 309 [MH]$^+$

Preparation 29

2,5-Difluoro-4-[(3-methoxyphenoxy)methyl]benzoic acid

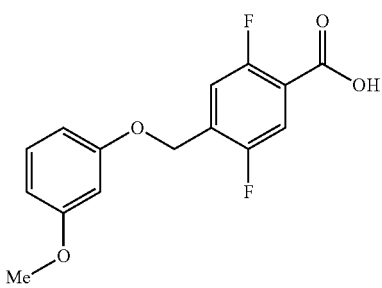 [SMILES: COc1cccc(OCc2cc(F)c(C(=O)O)cc2F)c1]

To a solution of methyl 2,5-difluoro-4-[(3-methoxyphenoxy)methyl]benzoate (Preparation 28, 441 mg, 1.4 mmol) in THF (10 mL) was added aqueous lithium hydroxide (1 M, 1.6 mL) and the reaction mixture stirred under nitrogen at room temperature. After 5 hours, the reaction was evaporated in vacuo and the residue suspended in a water/EtOAc mixture (20 mL), acidified with a few drops of aqueous 1 M hydrochloric acid. The layers were separated and the aqueous layer further extracted with EtOAc (10 mL). The combined organics were dried over magnesium sulphate and concentrated in vacuo to yield the title compound as an off white solid which was used in the next step without further purification (371 mg, 88%):

LCMS Rt=2.75 minutes MS m/z 295 [MH]$^+$

Preparation 30

Ethyl 4-{[4-(2-methyl-1H-imidazol-1-yl)benzyl]oxy}benzoate

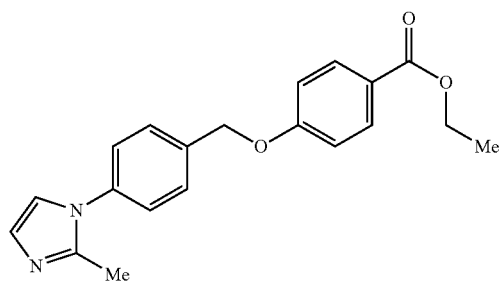 [SMILES: CCOC(=O)c1ccc(OCc2ccc(-n3ccnc3C)cc2)cc1]

To a mixture of ethyl 4-hydroxybenzoate (864 mg, 5.2 mmol) and 4-(2-methylimidazoyl)benzyl chloride (1.03 g, 5.0 mmol) in DMF (10 mL) was added potassium carbonate (3.45 g, 25 mmol) and the mixture was stirred for 5 hours at room temperature and 1 hour at 50° C. The reaction mixture was concentrated in vacuo and the residue diluted with water (50 mL) and extracted with EtOAc (100 mL). The organic layer was washed with water, brine, dried over magnesium sulphate and concentrated in vacuo. The resulting residue was purified by silica gel chromatography eluting with 10%

EtOAc in heptane to yield the title compound as a solid (1.42 g), which was taken on to the next step (without further purification).

Preparation 31

4-{[4-(2-Methyl-1H-imidazol-1-yl)benzyl]oxy}benzoic acid

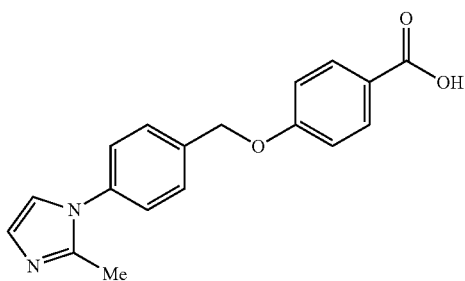 [SMILES: Cc1nccn1-c1ccc(COc2ccc(C(=O)O)cc2)cc1]

To a solution of ethyl 4-{[4-(2-methyl-1H-imidazol-1-yl)benzyl]oxy}benzoate (Preparation 30, 507 mg, 1.9 mmol) in THF/MeOH/Water (3:3:1, 7 mL) was added lithium hydroxide monohydrate (198 mg, 4.9 mmol) the resulting reaction mixture was heated under reflux for 72 hours. Lithium hydroxide monohydrate (100 mg, 2.5 mmol) was added and the reaction mixture heated at reflux for further 3 hours. The solvent was reduced in vacuo and the residue diluted with water. The resulting aqueous mixture was acidified with 0.2 M aqueous hydrochloric acid to pH 6.5 and the solid precipitate was collected, washed with water and diethyl ether and dried under reduced pressure at 50° C. to yield the title compound as a white solid, which was carried through to the next step without further purification.

The following preparations were prepared according to the method described for Preparation 28, using the corresponding benzyl bromide and phenol precursors.

| Prep | Name | Data |
|---|---|---|
| 32 | Methyl 4-((3-chlorophenoxy)methyl)benzoate | $^1$H NMR (400 MHz, CDCl$_3$): δ 3.93 (s, 3 H), 5.09 (s, 2 H), 6.85 (m, 1 H), 6.94-7.00 (m, 2 H), 7.20 (dd, 1 H), 7.46-7.51 (m, 2 H), 8.07 (d, 2 H). LCMS Rt = 3.59 min. MS m/z 277 [M + H]+, |
| 33 | Methyl 3-chloro-4-((3,4-dichlorophenoxy)methyl)benzoate | $^1$H NMR (400 MHz, d$_6$-DMSO): δ 3.88 (s, 3H), 5.28 (s, 2H), 7.09 (dd, 1H) 7.41 (d, 1H), 7.56 (d, 1H), 7.76 (d, 1H) 7.95-8.00 (m, 2H). LCMS Rt = 4.02 min. Molecular ion not visible. |
| 34 | Methyl 4-((3,4-dichlorophenoxy)methyl)-2,5-difluorobenzoate | $^1$H NMR (400 MHz, CDCl$_3$): δ 3.95 (s, 3H); 5.05 (s, 2H); 6.80 (d, 2H); 7.05 (d, 1H); 7.25-7.30 (m, 2H); 7.65 (m, 1H) LCMS Rt = 3.88 min. Molecular ion not visible. |
| 35 | Methyl 2,5-difluoro-4-((2-methoxyphenoxy)methyl)benzoate | LCMS Rt = 3.15 min. MS m/z 309 [MH]+ |
| 36 | Methyl 4-((4-chloro-2-methoxyphenoxy)methyl)-2,5-difluorobenzoate | LCMS Rt = 3.59 min. MS m/z 343 [M + H]+, |
| 37 | Methyl 4-[(3,4-dichlorophenoxy)methyl]-2-methoxybenzoate | $^1$H NMR (400 MHz, CDCl$_3$): δ 3.89 (s, 3H), 3.92 (s, 3H), 6.81 (dd, 1H), 6.97-7.03 (m, 2H), 7.07 (d, 1H), 7.33 (d, 1H), 7.82 (d, 1H). LCMS Rt = 1.86 min. MS m/z 341 [MH]+ |
| 38 | Methyl 4-{[2-pyridazin-4-yl-4-(trifluoromethyl)phenoxy]methyl}benzoate | $^1$H NMR (400 MHz, CDCl$_3$): δ 3.92 (s, 3H), 5.26 (s, 2H), 7.14 (d, 1H), 7.38 (d, 2H), 7.64-7.67 (m, 2H), 7.67-7.71 (m, 1H), 8.04 (d, 2H), 9.25 (dd, 1H), 9.44 (dd, 1H). LCMS Rt = 1.37 min. MS m/z 389 [MH]+ |
| 39 | Ethyl 4-{[4-chloro-3-(trifluoromethyl)phenoxy]methyl}benzoate | $^1$H NMR (400 MHz, CDCl$_3$): δ 1.40 (t, 3H), 4.39 (q, 2H), 5.14 (s, 2H), 7.04 (dd, 1H), 7.29 (d, 1H), 7.39 (d, 1H), 7.48 (d, 2H), 8.08 (d, 2H). LCMS Rt = 2.01 min. MS m/z 359 [MH]+ |
| 40 | Methyl 4-((3,4-dichlorophenoxy)methyl)-3-methoxybenzoate | $^1$H NMR (400 MHz, CDCl$_3$): δ 3.93 (s, 6H), 5.11 (s, 2H), 6.83 (dd, 1H), 7.32 (d, 1H), 7.49 (d, 1H), 7.57 (s, 1H), 7.67 (d, 1H). LCMS Rt = 3.53 min. MS m/z 342 [M + H]+, |

No Preparations 41-45

The following preparations were prepared according to the method described for Preparation 29, using the corresponding benzoate precursor.

| Prep | Name | Data |
|---|---|---|
| 46 | 4-((3-Chlorophenoxy)methyl)benzoic acid | LCMS Rt = 3.12 min. MS m/z 262 [MH]– |
| 47 | 3-Chloro-4-((3,4-dichlorophenoxy)methyl)benzoic acid | $^1$H NMR (400 MHz, d$_6$-DMSO): δ 5.27 (s, 2H), 7.08 (dd, 1H), 7.41 (d, 1H), 7.56 (d, 1H), 7.73 (d, 1H) 7.92-7.97 (m, 2H), 13.38 (brs, 1H). LCMS Rt = 3.60 min. MS m/z 330 [M – H]– |
| 48 | 4-((3,4-Dichlorophenoxy)methyl)-2,5-difluorobenzoic acid | $^1$H NMR (400 MHz, d$_6$-DMSO): δ 5.20 (s, 2H); 7.00 (m, 1H); 7.40 (s, 1H); 7.55 (m, 2H); 7.65 (m, 1H); 13.5 (brs, 1H). LCMS Rt = 3.89 min. MS m/z 332 [M – H]– |
| 49 | 2,5-Difluoro-4-((2-methoxyphenoxy)methyl)benzoic acid | LCMS Rt = 2.57 min. MS m/z 295 [MH]+ |
| 50 | 4-((4-Chloro-2-methoxyphenoxy)methyl)-2,5-difluorobenzoic acid | LCMS Rt = 3.06 min. MS m/z 329 [M – H]– |
| 51 | 4-[(3,4-Dichlorophenoxy)methyl]-2-methoxybenzoic acid | $^1$H NMR (400 MHz, d$_6$-DMSO): δ 3.81(s, 3H), 5.17(s, 2H), 7.01-7.06(m, 2H), 7.18 (d, 1H), 7.34 (d, 1H), 7.53 (d, 1H), 7.63 (d, 1H), 12.56-12.64 (br, 1H). MS m/z 327 [MH]+, 325 [M – H]– |
| 52 | 4-{[2-Pyridazin-4-yl-4-(trifluoromethyl)phenoxy]methyl}benzoic acid | $^1$H NMR (400 MHz, d$_6$-DMSO): δ 5.38 (s, 2H), 7.46 (d, 1H), 7.50 (d, 2H) 7.83-7.95 (m, 4H), 7.97 (dd, 1H), 9.31 (dd, 1H), 9.51 (dd, 1H). LCMS Rt = 1.51 min. MS m/z 375 [MH]+, 373 [M – H]– |
| 53 | 4-{[4-Chloro-3-(trifluoromethyl)phenoxy]methyl}benzoic acid | $^1$H NMR (400 MHz, CDCl$_3$): δ 4.99 (s, 2H), 6.92 (dd, 1H), 7.13 (d, 1H), 7.24 (s, 1H), 7.32 (d, 2H), 7.91 (d, 2H). LCMS Rt = 1.76 min. MS m/z 329 [M – H]– |
| 54 | 4-((3,4-Dichlorophenoxy)methyl)-3-methoxybenzoic acid | $^1$H NMR (400 MHz, d$_6$-DMSO): δ 3.90 (s, 3H), 5.10 (s, 2H), 7.02 (dd, 1H), 7.32 (d, 1H), 7.48-7.57 (m, 4H), 13.00 (br, 1H). LCMS Rt = 2.50 min. m/z 325 [M – H]$^-$ |

Preparation 55

4-Methyl-N-(methylsulfonyl)benzamide

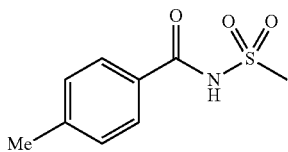

To a solution of 4-methylbenzoic acid (1.07 g, 7.82 mmol), N-[3-(dimethylamino)propyl]-N'-ethylcarbodiimide hydrochloride (3.00 g, 15.6 mmol) and N,N-dimethylpyridin-4-amine (2.01 g, 15.6 mmol) in DCM (50 mL) was added methanesulphonamide (1.53 g, 15.6 mmol) and the resulting mixture stirred for 18 hours at room temperature under nitrogen. The reaction mixture was poured into water (100 mL) and extracted with DCM (2×75 mL). The combined organics were dried over magnesium sulphate and evaporated in vacuo, azeotroping with toluene (2×20 mL) to yield a crude solid (2.14 g). The solid was dissolved in DCM (100 mL) and washed with aqueous hydrochloric acid solution (2 M, 2×50 mL). The organic layer was extracted with saturated solution of sodium carbonate (2×50 mL) and the aqueous washed with DCM (50 mL). The basic aqueous layer was acidified to pH 2 with 2 M aqueous hydrochloric acid and extracted with DCM (2×50 mL). The combined organic extracts were washed with water (20 mL), dried over magnesium sulphate and evaporated in vacuo to yield the first crop of the title compound as a white solid (368 mg). All aqueous layers from the extraction process were then evaporated in vacuo to yield a white solid which was triturated with DCM (50 mL). The organics were dried over magnesium sulphate and evaporated in vacuo to yield a white solid, which was redissolved in DCM (50 mL), washed with hydrochloric acid (2 M, 20 mL) dried over magnesium sulphate and evaporated in vacuo to yield a second crop of the title compound as a white crystalline solid (578 mg, combined yield of 56%).

$^1$H NMR (400 MHz, CDCl$_3$): δ 2.45 (s, 3H), 3.44 (s, 3H), 7.30 (d, 2H), 7.74 (d, 2H), 8.56 (br, 1H).

LCMS Rt=1.13 minutes MS m/z 214 [MH]$^+$, 212 [M–H]$^-$

Preparation 56

4-(Bromomethyl)-N-(methylsulfonyl)benzamide

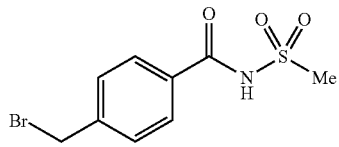 [SMILES: CS(=O)(=O)NC(=O)c1ccc(CBr)cc1]

To a solution of 4-methyl-N-(methylsulfonyl)benzamide (Preparation 55, 550 mg, 2.58 mmol) in tetrachloromethane (10 mL) was added N-bromosuccinimide (459 mg, 2.58 mmol) and diphenylperoxyanhydride (62.5 mg, 0.258 mmol) and the mixture was heated at reflux under nitrogen for 4 hours. The reaction mixture was cooled to room temperature, poured into water (100 mL) and extracted with DCM (50 mL). The organic layer was dried over magnesium sulphate and evaporated in vacuo to yield a cream solid. The solid was re-dissolved in trichloromethane (10 mL), diphenylperoxyanhydride (62 mg, 0.25 mmol) and N-bromosuccinimide (300 mg, 1.69 mmol) were added and the mixture heated at reflux for 6 hours then cooled to room temperature and evaporated in vacuo. The resulting residue was partitioned between DCM (50 mL) and water (50 mL), the aqueous further extracted with DCM (50 mL) and the combined organics dried over magnesium sulphate and concentrated in vacuo to yield a cream solid (625 mg). A portion of this material was purified by silica gel chromatography eluting with 0 to 30% EtOAc in heptane to yield the title compound as a white solid (25 mg).

LCMS Rt=1.27 minutes MS m/z 290 [M−H]$^{−1}$ $^1$H NMR (400 MHz, d$_6$-DMSO): δ 3.35 (s, 3H), 4.74 (s, 2H), 7.57 (d, 2H), 7.90 (d, 2H), 12.16 (br, 1H).

Preparation 57

4-(Bromomethyl)-1-chloro-2-methoxybenzene

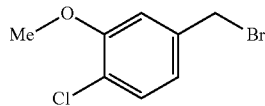 [SMILES: COc1cc(CBr)ccc1Cl]

To a solution of 4-chloro-3-methoxytoluene (200 mg, 1.28 mmol) in carbon tetrachloride (12 mL) was added N-bromosuccinimide (228 mg, 1.28 mmol) and benzoyl peroxide (31 mg, 0.128 mmol). The mixture was heated at reflux for 2 hours. The reaction mixture was allowed to cool to room temperature and the solvent removed in vacuo. The resulting residue was partitioned between DCM and water. The organic layer was separated, dried over sodium sulphate and evaporated to yield an orange oil. The oil was purified by silica gel chromatography eluting with 30% heptanes in DCM to afford the title compound (45 mg) as a 3.5:1:1 mixture with 4-chloro-3-methoxytoluene and 1-chloro-4-(dibromomethyl)-2-methoxybenzene respectively, which was used in the next step without further purification.

$^1$H NMR (400 MHz, CDCl$_3$): δ 3.95 (s, 3H), 4.45 (s, 2H), 6.75 (s, 1H), 6.95 (d, 1H), 7.33 (d, 1H).

LCMS Rt=3.17 minutes Molecular ion not observed

Preparation 58

5-(Bromomethyl)-2-chlorobenzonitrile

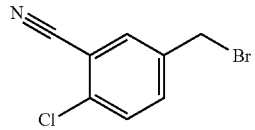 [SMILES: N#Cc1cc(CBr)ccc1Cl]

To a solution of 5-methyl-2-chlorobenzonitrile (200 mg, 1.32 mmol) in carbon tetrachloride (12 mL) was added N-bromosuccinimide (235 mg, 1.32 mmol) and benzoyl peroxide (32 mg, 0.132 mmol). The mixture was heated at reflux for 2 hours. The reaction was allowed to cool to room temperature and the solvent removed in vacuo. The resulting residue was partitioned between DCM and water. The organic layer was separated, dried over sodium sulphate and evaporated to give an orange oil. The oil was purified by silica gel chromatography eluting with 50% heptanes in DCM to afford the title compound (192 mg) as a 2:1:1 mixture with 5-methyl-2-chlorobenzonitrile and 2-chloro-5-(dibromomethyl)benzonitrile respectively, which was used in the next step without further purification.

$^1$H NMR (400 MHz, CDCl$_3$): δ 4.50 (s, 2H), 6.78 (s, 1H), 6.95 (d, 1H), 7.35 (d, 1H).

LCMS Rt=3.12 minutes Molecular ion not observed

Preparation 59

4-(Bromomethyl)-2-chloro-1-methoxybenzene

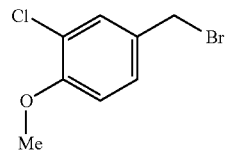 [SMILES: COc1ccc(CBr)cc1Cl]

To a solution of 2-chloro-1-methoxy-4-methylbenzene (300 mg, 1.92 mmol) in carbon tetrachloride (10.0 mL) was added N-bromosuccinimide (445 mg, 2.50 mmol) and benzoylperoxide (4.6 mg, 0.0192 mmol) and the reaction heated to reflux for 4.5 hours.

The reaction mixture was allowed to cool to room temperature, diluted with DCM (20.0 mL) and partitioned with a saturated aqueous solution of sodium hydrogen peroxide (30.0 mL). The organic layer was separated and the aqueous extracted with DCM (30 mL). The combined organics were washed with brine (50.0 mL), filtered through a phase separator cartridge and the solvent removed in vacuo to yield a yellow oil, which was purified by silica gel chromatography eluting with 50% heptane in DCM to yield the title compound (263 mg, 58%).

$^1$H NMR (400 MHz, CDCl$_3$): δ 3.90 (s, 3H), 4.44 (s, 2H), 7.25 (dd, 1H), 7.41 (d, 1H), 8.88 (d, 1H).

LCMS Rt=3.29 minutes Molecular ion not observed

Preparation 60

5-Bromo-2-[(3,4-dichlorophenoxy)methyl]benzonitrile

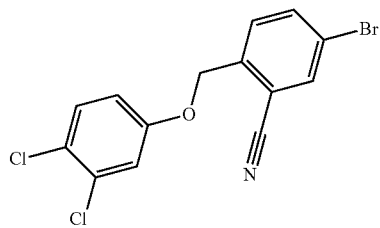 [SMILES: N#Cc1cc(Br)ccc1COc1ccc(Cl)c(Cl)c1]

A mixture of 3,4-dichlorophenol (267.1 mg, 1.639 mmol), 5-bromo-2-(bromomethyl)benzonitrile (447.3 mg, 1.627 mmol), and potassium carbonate (674.1 mg, 4.877 mmol) in acetone (20 mL) was heated to 75° C. under nitrogen for 18 hours. The reaction mixture was cooled to room temperature, diluted with EtOAc (20 mL) and filtered through arbocel. The arbocel was then washed with EtOAc (2×20 mL), and the combined organics were washed with brine (3×20 mL), dried over sodium sulphate, filtered and concentrated in vacuo to afford the title compound as a white solid (549.9 mg, 95%).

$^1$H NMR (400 MHz, CDCl$_3$): δ 5.18 (s, 2H), 6.86 (dd, 1H), 7.11 (d, 1H), 7.38 (d, 1H), 7.53 (d, 1H), 7.78 (dd, 1H), 7.86 (d, 1H).

LCMS Rt=3.86 minutes MS m/z 356 [MH]+

Preparation 61

2,5-Difluoro-4-[4-chloro-3-(trifluoromethyl)phenyl-methoxy]-benzonitrile

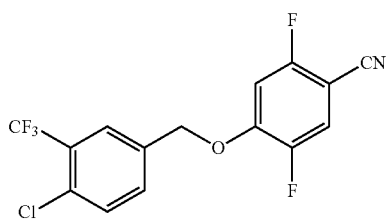 [SMILES: N#Cc1cc(F)c(OCc2ccc(Cl)c(C(F)(F)F)c2)cc1F]

To a solution of 4-chloro-3-(trifluoromethyl)-benzylalcohol (0.27 g, 1.28 mmol) and 2,4,5-trifluorobenzonitrile (0.2 g, 1.28 mmol) in DMSO (5 mL) was added potassium carbonate (0.33 g, 0.25 mmol). The resulting mixture was stirred at room temperature for 18 hours. The reaction mixture was partitioned between water (15 mL) and EtOAc (20 mL). The organic layer was separated, dried over magnesium sulphate, filtered and evaporated to yield the title compound (0.43 g, 97%).

$^1$H NMR (CD$_3$OD, 400 MHz): δ 5.28 (s, 2H), 7.30-7.38 (m, 1H), 7.55-7.75 (m, 3H), 7.90 (s, 1H).

Molecular ion not observed

Preparation 62

2,5-Difluoro-4-[4-chloro-3-(trifluoromethyl)phenyl-methoxy]-benzamide

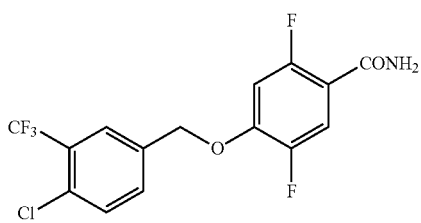 [SMILES: NC(=O)c1cc(F)c(OCc2ccc(Cl)c(C(F)(F)F)c2)cc1F]

To a suspension of 2,5-difluoro-4-[4-chloro-3-(trifluoromethyl)phenylmethoxy]-benzonitrile (Preparation 61, 0.2 g, 0.5 mmol) and potassium carbonate (0.39 g, 2.5 mmol) in DMSO (3 mL), was added hydrogen peroxide (30% solution in water, 0.6 mL, 5 mmol) at room temperature. The resulting mixture was stirred for 3 hours at room temperature. Water (30 mL) was then added and the precipitate formed was filtered. The filtrate was extracted twice with EtOAc and combined with the solid. The resulting organic solution was dried over magnesium sulphate, filtered and evaporated to afford the title compound as a white solid (160 mg, 76%).

$^1$H NMR (CD$_3$OD, 400 MHz): δ 5.20 (s, 2H), 7.00-7.08 (m, 1H), 7.50-7.65 (m, 3H), 7.80 (s, 1H).

Molecular ion not visible

Preparation 63 tert-Butyl 4-(3-hydroxyphenyl)piperidine-1-carboxylate

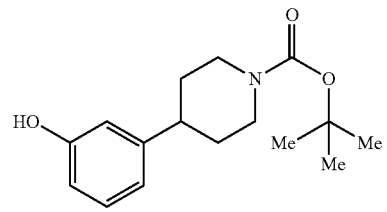 [SMILES: CC(C)(C)OC(=O)N1CCC(c2cccc(O)c2)CC1]

Di-t-butyl dicarbonate (3.66 g, 16.7 mmol) was added in one portion to a suspension of 4-(3-Hydroxyphenyl)piperidine (commercial, 2.97 g, 16.7 mmol) in DCM (20 mL) and stirred at room temperature for 1 hour. The reaction mixture was concentrated in vacuo to yield an oil, which crystallized upon standing. The solid was redissolved in EtOAc and washed with an aqueous solution of sodium hydrogencarbonate, dried over sodium sulphate and concentrated in vacuo to yield the title compound as a solid (4.36 g, 94%).

MS m/z 278 [MH]+, 276 [M–H]–

Preparation 64

4-chloro-2-(1-methyl-1H-pyrazol-5-yl)phenol

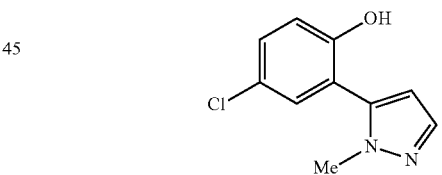

To a suspension of 6-chlorochromone (2.00 g, 0.011 mol) in ethanol (35 mL) was added methylhydrazine sulfate (1.85 g, 0.013 mol) and triethylamine (2.0 mL, 0.014 mol) and the mixture was heated at reflux for 18 hours. After cooling to room temperature, the reaction mixture was concentrated in vacuo and the resulting residue purified by silica gel chromatography eluting with 0 to 100% EtOAc in hexane to yield two regioisomeric products in a 1:4 ratio, the title compound being the minor regiosiomer.

LCMS Rt=1.43 minutes MS m/z 209 [MH]+

$^1$H NMR (400 MHz, CDCl$_3$): δ 2.96 (s, 3H), 5.52 (m, 1H), 6.40 (d, 1H), 6.99 (d, 1H), 7.22 (d, 1H), 7.34 (dd, 1H), 7.65 (d, 1H).

Preparation 65

Methyl 4-(bromomethyl)-2-methylbenzoate (CAS)

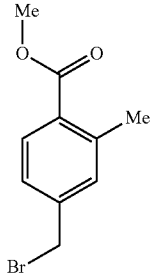

Prepared according to EP6735A1, page 68, description 46. May also be prepared according to the Journal of the Chemical Society Transactions, 1925, 127, pp 2275-97.

No Preparation 66

Preparation 67

2-Pyridazin-4-yl-4-(trifluoromethyl)phenol

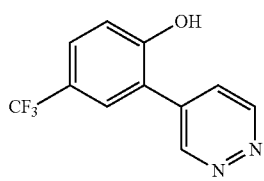 [SMILES: Oc1ccc(C(F)(F)F)cc1-c1ccnnc1]

Acetonitrile (9 L) was sparged with nitrogen for 2 hours. To the solvent was added cesium fluoride (335.8 g, 2.21 mol), 4-(tributylstannyl)pyridazine (408 g, 1.11 mol), 4-trifluoromethyl-6-iodophenol (318.3 g, 1.11 moles), palladium tetrakis 25 triphenylphosphine (61.31 g, 53.05 mmol) and copper (I) iodide (40 g, 210 mmol) at 20° C. The resulting orange suspension was heated to 45-50° C. for 2 hours. The reaction was cooled and partitioned between TBME (2×5 L) and aqueous hydrochloric acid solution (2 N, 2×5 L). The resulting biphasic solution was filtered and the layers separated. The aqueous phases were combined and basified with a sodium hydroxide solution (4 M, 6 L) to obtain a pH=4-5. The resulting suspension was extracted with EtOAc (10 L) and the organic layer concentrated in vacuo to afford the title compound as an orange solid (60%).

LCMS Rt=1.44 minutes MS m/z 241 [MH]+

$^1$H NMR (400 MHz, d$_6$-DMSO): δ 7.20 (d, 1H), 7.65 (dd, 1H), 7.80 (s, 1H), 7.90 (m, 1H), 9.25 (d, 1H), 9.50 (s, 1H), 11.10 (s, 1H).

Preparation 68

4-Chloro-3-(difluoromethoxy)phenol

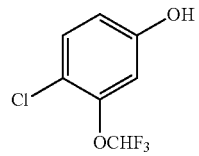

Prepared according to Preparation 69 using 4-bromo-2-(difluoromethoxy)chlorobenzene (Preparation 71, 1.5 g, 5.9 mmol).

$^1$H NMR (400 MHz, CDCl$_3$): δ 6.52 (t, 1H), 6.68 (d, 1H), 6.78 (dd, 1H), 7.29 (d, 1H).

LCMS Rt=1.27 minutes MS m/z 193 [M−H]$^-$

Preparation 69

3-Chloro-4-(difluoromethoxy)phenol

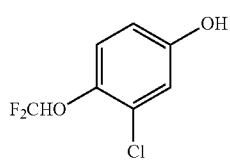

To a solution of 4-bromo-2-chloro-1-(difluoromethoxy) benzene (Preparation 70, 0.83 g, 3.2 mmol) in THF (16 mL) was added 4,4,4',4',5,5,5',5'-octamethyl-2,2'-bi-1,3,2-dioxaborolane (0.90 g, 3.6 mmol), Pd(dppf)Cl$_2$ (0.12 g, 0.16 mmol), and potassium acetate (0.98 g, 9.7 mmol) under a nitrogen atmosphere and the mixture heated at reflux for 2 hours. The reaction mixture was then concentrated in vacuo, the resulting residue filtered through silica gel pad with arbocel and washed EtOAc. The filtrate was concentrated in vacuo to yield a crude product of 2-[3-chloro-4-(difluoromethoxy)phenyl]-4,4,5,5-tetramethyl-1,3,2-dioxaborolane. A solution of crude 2-[3-chloro-4-(difluoromethoxy) phenyl]-4,4,5,5-tetramethyl-1,3,2-dioxaborolane (1.0 g, 3.3 mmol) in acetone (10 mL) was added to an aqueous oxone solution (2.6 g, 3.9 mmol, 10 mL) dropwise with stirring at 0° C. for 1 hour. The reaction mixture was partitioned between water (20 mL) and EtOAc (20 mL) and the organic layer was washed with brine, dried over sodium sulphate, filtered, and concentrated in vacuo. The resulting crude was purified by silica gel chromatography eluting with 0 to 40% EtOAc in heptane to afford the title compound as a pale brown oil (0.53 g, 82%):

$^1$H NMR (400 MHz, CDCl$_3$): δ 6.45 (m, 1H), 6.73 (d, 1H), 6.95 (d, 1H), 7.13 (dd, 1H).

LCMS Rt=1.33 minutes MS m/z 193 [M−H]$^-$

Preparation 70

4-Bromo-2-chloro-(difluoromethoxy)benzene

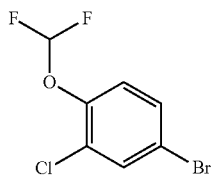 [SMILES: FC(F)Oc1ccc(Br)cc1Cl]

4-Bromo-2-chlorophenol (1.0 g, 4.8 mmol) was dissolved in DMF (35 mL) and water (5 mL) was added followed by sodium chloro(difluoro)acetate (2.0 g, 12 mmol) and cesium carbonate (3.1 g, 9.6 mmol). The mixture was stirred for 15 minutes at room temperature and then heated to 100° C. for 2 hours under nitrogen. The mixture was partitioned between water (50 mL) and TBME (50 mL). The organic phase was separated, washed brine, dried over sodium sulphate, filtered, and concentrated in vacuo. The resulting crude product was purified by silica gel chromatography eluting with 0 to 30% EtOAc in heptane to afford the title compound as colourless oil (0.83 g, 67%).

$^1$H NMR (400 MHz, CDCl$_3$): δ 6.52 (t, 1H), 7.14 (dd, 1H), 7.40 (d, 1H), 7.62 (d, 1H).

LCMS Rt=1.66 minutes Molecular ion not visible

Preparation 71

4-Bromo-2-(difluoromethoxy)chlorobenzene

Prepared according to Preparation 70 using 5-bromo-2-chlorophenol (1.5 g, 7.2 mmol).

$^1$H NMR (400 MHz, CDCl$_3$): δ 6.54 (t, 1H), 7.32 (d, 2H), 7.41 (m, 1H).

LCMS Rt=1.70 minutes Molecular ion not visible

The ability of the compounds of formula (I) to block the Nav1.7 (or SCN9A) channel were measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 µg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 µg/ml G-418 in an incubator at 37° C. with a humidified atmosphere of 10% CO$_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM CaCl$_2$, 5.4 mM KCl, 1 mM MgCl$_2$, 10 mM glucose, and 10 mM HEPES, pH 7.4, with NaOH. Pipettes were filled with an intracellular solution of the following composition: 135 mM CsF, 5 mM CsCl, 2 mM MgCl$_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" (EIC$_{50}$) values were calculated from single point electrophysiology data by the following equation, (tested concentration, uM)×(100-% inhibition/% inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of 1×10$^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays may also be conducted using the Ionworks Quattro automated electrophysiological platform (Molecular Devices Corp). Intracellular and extracellular solutions were as described above with the following changes, 100 μg/ml amphotericin was added to the intracellular solution to perforate the membrane and allow electrical access to the cells. hSCN9A cells were grown and harvested as for PatchXpress and cells were resuspended in extracellular solution at a concentration of $3\text{-}4\times10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Unless otherwise stated, compounds of the Examples were tested in the assay described above using the PatchXpress platform and found to have the Nav1.7 $EIC_{50}$ (uM) values specified in the table below.

| Ex. | $EIC_{50}$ |
|---|---|
| 1 | 0.0095 |
| 2 | 0.064 |
| 3 | 0.29 |
| 4 | 1.2 |
| 5 | 1.7 |
| 6 | 1.3 |
| 7 | 3.0 |
| 8 | 6.9 |
| 9 | 0.67 |
| 10 | 1.5 |
| 11 | 0.11 |
| 12 | 12 |
| 13 | NT |
| 14 | 8.1 |
| 15 | 1.7 |
| 16 | 0.76 |
| 17 | 8.4 |
| 18 | 0.93 |
| 19 | 0.058 |
| 20 | 2.4 |
| 21 | 0.71 |
| 22 | >3 |
| 23 | 0.38 |
| 24 | 0.78 |
| 25 | 0.72 |
| 26 | 0.078 |
| 27 | 0.38 |
| 28 | 0.058 |
| 29 | 0.086 |
| 30 | 1.9 |
| 31 | 22 (IW) |
| 32 | NT |
| 33 | NT |
| 34 | 8.5 |
| 35 | >3 |
| 36 | >3 |
| 37 | >3 |
| 38 | >3 |
| 39 | NT |
| 40 | 0.56 |
| 41 | 3.7 |
| 42 | 0.25 |
| 43 | 4.2 |
| 44 | 2.0 |
| 45 | NT |
| 46 | NT |
| 47 | 1.4 |
| 48 | 1.1 |
| 49 | 0.16 |
| 50 | 0.22 |
| 51 | 0.012 |
| 52 | 0.13 |
| 53 | 0.013 |
| 54 | 0.13 |
| 55 | 0.57 |
| 56 | 0.088 |
| 57 | 1.1 |
| 58 | 0.021 |
| 59 | 0.014 |
| 60 | 0.029 |
| 61 | <0.3 |
| 62 | <3 |
| 63 | 0.035 |
| 64 | >3 |
| 65 | 0.080 |
| 66 | >1 |
| 67 | 9.2 |
| 68 | 9.8 |
| 69 | 0.24 |
| 70 | 0.16 |
| 71 | 3.9 |
| 72 | 0.30 |
| 73 | 6.4 |
| 74 | 9.7 |
| 75 | 1.0 |
| 76 | 10 |
| 77 | >3 |
| 78 | 0.39 |
| No Ex | |
| 80 | >3 |
| No Ex | |
| 82 | 5.5 |
| 83 | 0.62 |
| 84 | 6.5 |
| 85 | 0.45 |
| 86 | 0.58 |
| 87 | 0.64 |
| 88 | 6.1 |
| 89 | >3 |
| 90 | >3 |
| 91 | 3.5 |
| 92 | 0.59 |
| 93 | >3 |
| 94 | 4.3 |
| No Ex | |
| No Ex | |
| 97 | 1.5 |
| 98 | 0.14 |
| 99 | 0.82 |
| 100 | 0.39 |
| 101 | 1.9 |
| 102 | >3 |
| 103 | 6.1 |
| 104 | 5.1 |
| 105 | 0.10 |
| 106 | 9.2 |
| 107 | 0.33 |
| 108 | 0.087 |
| 109 | 0.14 |
| 110 | 2.2 |
| 111 | >1 |
| 112 | 1.4 |
| 113 | 11 |
| No Ex | |
| 115 | 0.62 |
| 116 | 0.57 |
| 117 | 2.2 |
| 118 | >1 |
| 119 | 0.38 |
| 120 | 0.70 |
| 121 | 0.30 |
| 122 | 2.2 |

-continued

| Ex. | EIC$_{50}$ |
|---|---|
| 123 | 0.85 |
| 124 | 0.18 |
| 125 | 1.4 |
| 126 | >3 |
| 127 | 2.6 |
| 128 | 2.9 |
| 129 | 1.9 |
| 130 | 0.24 |
| 131 | >1 |
| 132 | >3 |
| 133 | >1 |
| 134 | 0.47 |
| 135 | >3 |
| 136 | >3 |
| 137 | >3 |
| 138 | 4.2 |
| 139 | >3 |
| 140 | 2.2 |
| 141 | 0.33 |
| 142 | 0.60 |
| 143 | 9.7 |
| 144 | 0.15 |
| 145 | 2.3 |
| 146 | >1 |
| 147 | 0.17 |
| 148 | >1 |
| 149 | 4.0 |
| 150 | 0.50 |
| 151 | 0.065 |
| 152 | 3.0 |
| 153 | 12 |
| 154 | 11 |
| 155 | 3.2 |
| 156 | 2.3 |
| 157 | 2.1 |
| 158 | 1.5 |
| 159 | 0.13 |
| 160 | 0.76 |
| 161 | NT |
| 162 | 0.73 |
| 163 | >1 |
| 164 | >3 |
| 165 | 0.74 |
| 166 | 1.3 |
| 167 | 2.6 |
| 168 | 3.1 |
| 169 | >3 |
| 170 | >3 |
| 171 | 2.9 |
| 172 | >3 |
| 173 | 0.25 |
| 174 | 1.3 |
| 175 | 2.1 |
| 176 | >1 |
| 177 | 2.1 |
| 178 | 0.81 |
| 179 | >1 |
| 180 | >3 |
| 181 | 0.57 |
| 182 | >1 |
| 183 | 4.3 |
| 184 | 2.6 |
| 185 | >1 |
| 186 | 7.3 |
| 187 | 4.2 |
| 188 | 2.5 |
| 189 | 1.5 |
| 190 | 0.62 |
| 191 | 7.6 |
| 192 | 3.1 |
| 193 | 4.7 |
| 194 | 1.7 |
| 195 | >3 |
| 196 | >1 |
| 197 | >1 |
| 198 | >1 |
| 199 | 2.4 |

-continued

| Ex. | EIC$_{50}$ |
|---|---|
| 200 | 5.0 |
| 201 | >1 |
| 202 | 11 |
| 203 | 1.7 |
| 204 | 3.6 |
| 205 | >3 |
| 206 | >1 |
| 207 | >0.3 |
| 208 | 2.6 |
| 209 | 3.0 |
| 210 | >1 |
| 211 | 2.6 |
| 212 | >0.3 |
| 213 | >0.3 |
| 214 | 3.8 |
| 215 | >1 |
| 216 | 3.8 |
| 217 | >1 |
| 218 | 3.4 |
| 219 | >1 |
| 220 | 1.7 |
| 221 | 1.8 |
| 222 | 3.6 |
| 223 | >0.3 |
| 224 | >0.3 |
| 225 | >0.3 |
| 226 | >1 |
| 227 | 0.94 |
| 228 | 1.2 |
| 229 | >1 |
| 230 | 2.2 |
| 231 | 1.4 |
| 232 | 2.1 |
| 233 | >1 |

NT—indicates that the compound was not tested.
IW—indicates assay by the Ionworks Quattro automated electrophysiological platform.

The ability of compounds of formula (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the EIC$_{50}$ value at the Nav1.7 channel to determine the selectivity of a given compound for Nav1.7 vs Nav1.5.

The invention claimed is:
1. A compound of formula (I):

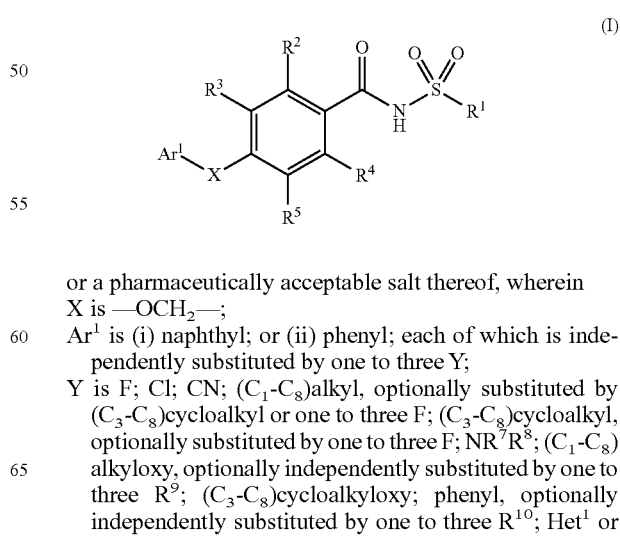

or a pharmaceutically acceptable salt thereof, wherein
X is —OCH$_2$—;
Ar$^1$ is (i) naphthyl; or (ii) phenyl; each of which is independently substituted by one to three Y;
Y is F; Cl; CN; (C$_1$-C$_8$)alkyl, optionally substituted by (C$_3$-C$_8$)cycloalkyl or one to three F; (C$_3$-C$_8$)cycloalkyl, optionally substituted by one to three F; NR$^7$R$^8$; (C$_1$-C$_8$) alkyloxy, optionally independently substituted by one to three R$^9$; (C$_3$-C$_8$)cycloalkyloxy; phenyl, optionally independently substituted by one to three R$^{10}$; Het$^1$ or Het²; wherein (C₃-C₈)cycloalkyloxy may be optionally fused to a phenyl ring or may be independently substituted by one to three R¹⁰;
R¹ is (C₁-C₆)alkyl or (C₃-C₈)cycloalkyl, each of which is optionally substituted by one to three F;
R², R³, R⁴ are independently H, F, Cl or —OCH₃;
R⁵ is H, CN, F, Cl or R⁶;
R⁶ is a group selected from (C₁-C₆)alkyl and (C₁-C₆)alkyloxy, wherein each group is optionally substituted, valency permitting, by one to five F;
R⁷ and R⁸ are independently H; (C₁-C₈)alkyl, optionally independently substituted by one to three R¹¹; (C₃-C₈)cycloalkyl; or 'C-linked' Het¹; wherein (C₃-C₈)cycloalkyl may be optionally fused to a phenyl ring or may be independently substituted by one to three R¹⁰; or
R⁷ and R⁸, taken together with the nitrogen atom to which they are attached, form a saturated, bridged, 7 to 9-membered ring;
R⁹ is F; (C₁-C₆)alkyloxy; (C₃-C₈)cycloalkyl, optionally substituted by one to three F; Het¹; or phenyl, optionally independently substituted by one to three R⁶;
R¹⁰ is F, Cl or R⁶;
R¹¹ is F; (C₁-C₆)alkyloxy; (C₃-C₈)cycloalkyl, optionally substituted by one to three F; 'C-linked' Het¹; or phenyl, optionally independently substituted by one to three R⁶;
Het¹ is a 3- to 8-membered saturated monoheterocycloalkyl comprising one or two ring members selected from —NR¹²— and —O—, said monoheterocycloalkyl being optionally substituted on a ring carbon atom by one to three substituents independently selected from F, (C₁-C₆)alkyl, (C₁-C₄)alkyloxy(C₀-C₄)alkylene and (C₃-C₈)cycloalkyl;
Het² is a 5- or 6-membered heteroaryl comprising one to three nitrogen atoms, said heteroaryl being optionally substituted by one to three substituents selected from F, Cl, CN and R⁶; and
R¹² is H, (C₁-C₆)alkyl or (C₃-C₈)cycloalkyl, wherein (C₁-C₆)alkyl and (C₃-C₈)cycloalkyl are optionally substituted by one to three F; or, when Het¹ is 'N-linked', is absent.

2. A compound according to claim 1 wherein Ar¹ is phenyl independently substituted by one to three Y.

3. A compound according to claim 1 wherein Ar¹ is phenyl independently substituted by one or two Y.

4. A compound according to claim 1 wherein Ar¹ is phenyl meta-substituted by Y, para-substituted by Y, or is meta- and para-substituted each independently by Y.

5. A compound according to claim 1 wherein Y is F; Cl; CN; (C₁-C₈)alkyl, optionally substituted by (C₃-C₈)cycloalkyl or one to three F; (C₃-C₈)cycloalkyl, optionally substituted by one to three F; (C₁-C₆)alkyloxy, optionally substituted by one to three F; or (C₃-C₈)cycloalkyloxy.

6. A compound according to claim 1 wherein R¹ is (C₁-C₄)alkyl or (C₃-C₆)cycloalkyl.

7. A compound according to claim 1 wherein R¹ is (C₁-C₃)alkyl or (C₃-C₄)cycloalkyl.

8. A compound according to claim 1 wherein R², R³ and R⁴ are independently H, F or Cl.

9. A compound according to claim 1 wherein R⁵ is H; CN; F; Cl; (C₁-C₄)alkyl, optionally substituted by one to three F; or (C₁-C₄)alkyloxy, optionally substituted by one to three F.

10. A pharmaceutical composition comprising a compound of formula (I) or a pharmaceutically acceptable salt thereof together, as defined in claim 1, with one or more pharmaceutically acceptable excipients.

11. A pharmaceutical composition according to claim 10 including one or more additional therapeutic agents.

12. A method for treating pain in a mammal comprising administering to to a mammal in need thereof an effective amount of a compound of the formula:

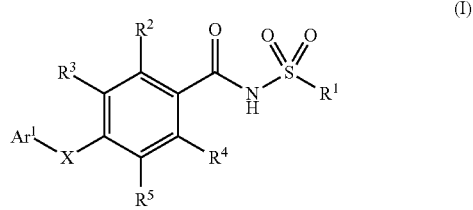

or a pharmaceutically acceptable salt thereof, wherein
X is —OCH₂— or —CH₂O—;
Ar¹ is (i) naphthyl; or (ii) phenyl; each of which is independently substituted by one to three Y;
Y is F; Cl; CN; (C₁-C₈)alkyl, optionally substituted by (C₃-C₈)cycloalkyl or one to three F; (C₃-C₈)cycloalkyl, optionally substituted by one to three F; NR⁷R⁸; (C₁-C₈)alkyloxy, optionally independently substituted by one to three R⁹; (C₃-C₈)cycloalkyloxy; phenyl, optionally independently substituted by one to three R¹⁰; Het¹ or Het²; wherein (C₃-C₈)cycloalkyloxy may be optionally fused to a phenyl ring or may be independently substituted by one to three R¹⁰;
R¹ is (C₁-C₆)alkyl or (C₃-C₈)cycloalkyl, each of which is optionally substituted by one to three F;
R², R³, R⁴ are independently H, F, Cl or —OCH₃;
R⁵ is H, CN, F, Cl or R⁶;
R⁶ is a group selected from (C₁-C₆)alkyl and (C₁-C₆)alkyloxy, wherein each group is optionally substituted, valency permitting, by one to five F;
R⁷ and R⁸ are independently H; (C₁-C₈)alkyl, optionally independently substituted by one to three R¹¹; (C₃-C₈)cycloalkyl; or 'C-linked' Het¹; wherein (C₃-C₈)cycloalkyl may be optionally fused to a phenyl ring or may be independently substituted by one to three R¹⁰; or
R⁷ and R⁸, taken together with the nitrogen atom to which they are attached, form a saturated, bridged, 7 to 9-membered ring;
R⁹ is F; (C₁-C₆)alkyloxy; (C₃-C₈)cycloalkyl, optionally substituted by one to three F; Het¹; or phenyl, optionally independently substituted by one to three R⁶;
R¹⁰ is F, Cl or R⁶;
R¹¹ is F; (C₁-C₆)alkyloxy; (C₃-C₈)cycloalkyl, optionally substituted by one to three F; 'C-linked' Het¹; or phenyl, optionally independently substituted by one to three R⁶;
Het¹ is a 3- to 8-membered saturated monoheterocycloalkyl comprising one or two ring members selected from —NR¹²— and —O—, said monoheterocycloalkyl being optionally substituted on a ring carbon atom by one to three substituents independently selected from F, (C₁-C₆)alkyl, (C₁-C₄)alkyloxy(C₀-C₄)alkylene and (C₃-C₈)cycloalkyl;
Het² is a 5- or 6-membered heteroaryl comprising one to three nitrogen atoms, said heteroaryl being optionally substituted by one to three substituents selected from F, Cl, CN and R⁶; and
R¹² is H, (C₁-C₆)alkyl or (C₃-C₈)cycloalkyl, wherein (C₁-C₆)alkyl and (C₃-C₈)cycloalkyl are optionally substituted by one to three F; or, when Het¹ is 'N-linked', is absent.

13. A method according to claim 12 in which said pain is selected from the group consisting of neuropathic, nociceptive and inflammatory pain.

\* \* \* \* \*